US008921097B2

(12) United States Patent
Neville, Jr. et al.

(10) Patent No.: US 8,921,097 B2
(45) Date of Patent: Dec. 30, 2014

(54) METHODS FOR EXPRESSION AND PURIFICATION OF IMMUNOTOXINS

(75) Inventors: David M. Neville, Jr., Bethesda, MD (US); Jung-Hee Woo, Temple, TX (US); Yuan-Yi Liu, Potomac, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 1037 days.

(21) Appl. No.: 12/957,165

(22) Filed: Nov. 30, 2010

(65) Prior Publication Data

US 2013/0217861 A1    Aug. 22, 2013

Related U.S. Application Data

(62) Division of application No. 10/566,886, filed as application No. PCT/US2004/024786 on Aug. 2, 2004, now Pat. No. 7,892,786.

(60) Provisional application No. 60/491,923, filed on Aug. 1, 2003.

(51) Int. Cl.
| | |
|---|---|
| C07K 1/00 | (2006.01) |
| C07K 16/46 | (2006.01) |
| C07K 1/18 | (2006.01) |
| C07K 1/20 | (2006.01) |
| C07K 1/22 | (2006.01) |
| C12N 1/19 | (2006.01) |

(52) U.S. Cl.
USPC .............. 435/288.6; 435/254.3; 435/483; 435/69.1; 435/69.7; 530/387.3; 530/416

(58) Field of Classification Search
None
See application file for complete search history.

(56) References Cited

U.S. PATENT DOCUMENTS

| | | | |
|---|---|---|---|
| 6,171,828 B1 | 1/2001 | Magota et al. | |
| 6,723,536 B2 | 4/2004 | Madsen et al. | |
| 6,992,172 B1 | 1/2006 | Chang et al. | |
| 2002/0142000 A1* | 10/2002 | Digan et al. | 424/183.1 |

FOREIGN PATENT DOCUMENTS

WO    01/87982 A2    11/2001

OTHER PUBLICATIONS

Varro et al, Hydrophobic interaction of extracellular protein A from *Staphylococcus aureus* with octyl-sepharose CL-4B, Abstract for Ann Immunol Hung. 1979;19:79-84.*
Gelsen, K.R., Use of Pichia Classic to produce small antibody-like protein scaffolds, Pichia Technology, 2013, pp. 1-2.*
Thermo Scientific, Product Manual IONPAC® AG4A Guard Column (4 x 50 mm, P/N 037042) IONPAC® AS4A Analytical Column (4 x 250 mm, P/N 037041), 2002, pp. 1-29.*
Thompson et al, Improved binding of a bivalent single-chain immunotoxin results in increased efficacy for in vivo T cell depletion, Protein Engineering, 2001, pp. 1035-1041.*
M. Jahic et al., "Temperature limited fed-batch technique for control of proteolysis in *Pichia pastoris* bioreactor cultures", Microbial Cell Factories, vol. 2, p. 11 (2003).
M. Jahic et al., "Analysis and control of proteolysis of a fusion protein in *Pichia pastoris* fed-batch processes", Journal of Biotechnology, 102(1), pp. 45-53 (2003).
Z. Li et al., "Low-temperature increases the yield of biologically active herring antifreeze protein in *Pichia pastoris*", Protein Expression and Purification, 21(3), pp. 438-445 (2001).
Y. Liu et al., "Targeted introduction of a diphtheria toxin resistant mutation into the chromosomal EF-2 locus of *Pichia pastoris* and expression of immunotoxin in the EF-2 mutants", Protein Expression and Purification, 30(2), pp. 262-274 (2003).
V. Sarramegna et al., "Optimizing Functional versus Total Expression of the Human mu-Opioid Receptor in *Pichia pastoris*", Protein Expression and Purification, 24(2), p. 212 (2002).
J.H. Woo et al., "Gene Optimization is necessary to express a bivalent anti-human anti-T cell immunotoxin in *Pichia pastoris*", Protein Expression and Purification, 25(2), pp. 270-282 (2002).
J.H. Woo et al., "Increasing secretion of a bivalent anti-T-cell immunotoxin by *Pichia pastoris*", Applied and Environmental Microbiology, 70(6), pp. 3370-3376 (2004).
McGrew et al., "Expression of trimeric CD40 ligand in *Pichia pastoris*: use of a rapid method to detect high-level expressing transformants", Gene, 187(2), pp. 193-200 (1997).

* cited by examiner

*Primary Examiner* — Maria Marvich
(74) *Attorney, Agent, or Firm* — Edwards Wildman Palmer LLP; Peter F. Corless

(57) ABSTRACT

The present invention relates to a method of expressing an immunotoxin in *Pichia pastoris* strain mutated to toxin resistance comprising a) growing the *Pichia pastoris* in a growth medium comprising an enzymatic digest of protein and yeast extract and maintaining a dissolved oxygen concentration at 40% and above; and b) performing methanol induction with a limited methanol feed of 0.5-0.75 ml/min/IO L of initial volume during induction along with a continuous infusion of yeast extract at a temperature below 17.5° C., antifoaming agent supplied up to 0.07%, agitation reduced to 400 RPM, and the induction phase extended out to 163 h.

10 Claims, 33 Drawing Sheets

| | | | |
|---|---|---|---|
| *H. sapiens*(66%) | ...706 | DVTLHADAIHRGGGQIIPTARR...858 | SEQ.ID NO:1 |
| *M. musculus*(3'mRNA) | ...... | DVTLHADAIHRGGGQIIPTARR... | SEQ ID NO:2 |
| *R. norvegicus*(66%) | ...706 | DVTLHADAIHRGGGQIIPTARR...858 | SEQ ID NO:3 |
| *C. griseus*(CHO, 67%) | ...706 | DVTLHADAIHR<u>G</u>GGQIIPTARR...858 | SEQ ID NO:4 |
| *D. melanogaster*(67%) | ...692 | DVTLHADAIHRGGGQIIPTTRR...848 | SEQ ID NO:5 |
| *C. elegans* (67%) | ...700 | DVTLHADAIHRGGGQIIPTARR...852 | SEQ ID NO:6 |
| *S. pombe* (79%) | ...690 | DVVLHADAIHRGGGQIIPTARR...842 | SEQ ID NO:7 |
| *P. pastoris* (88%) | ...690 | DVTLHADAIHRGGGQVIPTMKR...842 | SEQ ID NO:8 |
| *S. cerevisiae* | ...690 | DVTLHADAI<u>HR</u>GGGQIIPTMRR...842 | SEQ ID NO:9 |

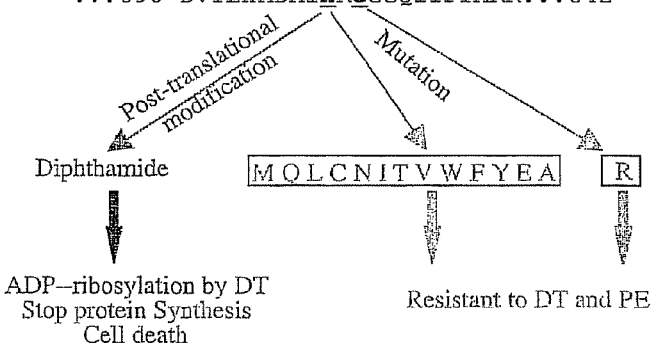

Diphthamide

ADP–ribosylation by DT
Stop protein Synthesis
Cell death

Resistant to DT and PE

```
2070        2079        2088        2097       2106        2115        2124        2133
                                                 R
                                              cGc cGc GGA
GAT GTT ACC CTG CAC GCC GAT GCT ATC CAC AGA GGT GGA GGA CAA GTC ATT CCA ACC ATG AAG AGA
 D   V   T   L   H   A   D   A   I   H   R   G   G   G   Q   V   I   P   T   M   K   R
690                                     700                                     710
                              SEQ ID NO:10
```

FIG. 1

```
mRNA  -54  ACTTTGAAGTTCTTAATTTTGTTCCTCGTAGAAAGAACGCATAGATAATT  -5
           ||||||||||||||||||||||||||||||||||||||||||||||||||
gDNA       ACTTTGAAGTTCTTAATTTTGTTCCTCGTAGAAAGAACGCATAGATAATT

-4   CAAAAATGG.........................................   4
           |||||||||
           CAAAAATGGGTATGTGTTTTTTTATAGTTCATGTGCCGAACAACTACCGTT
                    ‾‾‾‾‾
                     5'ss

5   .............................TTAACTTCACTGTCG  19
                                        |||||||||||||||
           TCAAGATGGGAGCCAGCCACTAACATCTCCTCTAGTTAACTTCACTGTCG
                              ‾‾‾‾‾‾‾‾‾‾‾   ‾‾‾
                              branch site    3'ss 20   ATCAGATGCGATCCCCTTATGGACAAGGTGTCCAACGTCCGTAACATGTCG  69
           ||||||||||||||||||||||||||||||||||||||||||||||||||
           ATCAGATGCGATCCCCTTATGGACAAGGTGACCAACGTCCGTAACATGTCG 70   GTTATTGCCCACGTTGATCACGGTAAGTCCACTTTAACTGACTCCCTGGT  119
           ||||||||||||||||||||||||||||||||||||||||||||||||||
           GTTATTGCCCACGTTGATCACGGTAAGTCCACTTTAACTGACTCCCTGGT
```

FIG. 2

```
                    -51         -41         -31         -21         -11          -1
            GATACTT TGAAGTTCTT AATTTTGTTC CTCGTAGAAA GAACGCATAG ATAATTCAAA 9              18              27              36              45              54
    ATG GTT AAC TTC ACT GTC GAT CAG ATG CGA TCC CTT ATG GAC AAG GTG ACC AAC
     M   V   N   F   T   V   D   Q   M   R   S   L   M   D   K   V   T   N 63              72              81              90              99             108
    GTC CGT AAC ATG TCG GTT ATT GCC CAC GTT GAT CAC GGT AAG TCC ACT TTA ACT
     V   R   N   M   S   V   I   A   H   V   D   H   G   K   S   T   L   T 117             126             135             144             153             162
    GAC TCC CTG GTG CAA CGT GCC GGT ATT ATT TCT GCT GCC AAG GCT GGT GAG GCC
     D   S   L   V   Q   R   A   G   I   I   S   A   A   K   A   G   E   A 171             180             189             198             207             216
    CGT TTC ACT GAT ACT AGA AAG GAC GAG CAA GAG AGA GGT ATC ACC ATC AAG TCT
     R   F  (T)  D   T   R   K   D   E   Q   E   R   G   I   T   I   K   S 225             234             243             252             261             270
    ACC GCC ATT TCT TTG TAC TCT GAG ATG GGT GAC GAC GAT GTC AAG GAG ATC AAG
     T   A   I   S   L   Y   S   E   M   G   D   D   D   V   K   E   I   K 279             288             297             306             315             324
    CAG AAG ACT GAA GGT AAC AGT TTC CTT ATC AAC TTA ATT GAC TCC CCA GGT CAC
     Q   K   T   E   G   N   S   F   L   I   N   L   I   D   S   P   G   H 333             342             351             360             369             378
    GTT GAC TTC TCT TCT GAG GTC ACT GCT GCT CTG CGT GTT ACT GAC GGT GCT TTG
     V   D   F   S   S   E   V   T   A   A   L   R   V   T   D   G   A   L 387             396             405             414             423             432
    GTC GTC GTT GAC TGT GTT GAA GGT GTC TGT GTT CAA ACT GAG ACC GTT TTG CGT
     V   V   V   D   C   V   E   G   V   C   V   Q   T   E   T   V   L   R 441             450             459             468             477             486
    CAA GCT TTG GGT GAA AGA ATC AAG CCA GTT GTT GTC ATT AAC AAG GTC GAC CGT
     Q   A   L   G   E   R   I   K   P   V   V   V   I   N   K   V   D   R 495             504             513             522             531             540
    GCT CTT TTG GAG TTG CAA GTT ACC AAG GAG GAC CTG TAC CAG TCT TTC GCT AGA
     A   L   L   E   L   Q   V   T   K   E   D   L   Y   Q   S   F   A   R 549             558             567             576             585             594
    ACC GTC GAG TCC GTA AAC GTC GTT ATC GCT ACT TAC ACT GAC AAG ACC ATT GGT
     T   V   E   S   V   N   V   V   I   A   T   Y   T   D   K   T   I   G 603             612             621             630             639             648
    GAC AAC CAA GTC TAC CCA GAA CAG GGT ACC GTC GCT TTC GGT TCA GGT CTG CAC
     D   N   Q   V   Y   P   E   Q   G   T   V   A   F   G   S   G   L   H 657             666             675             684             693             702
    GGA TGG GCT TTC ACC GTT AGA CAG TTC GCC ACT AGA TAC TCC AAG AAG TTC GGT
     G   W   A   F   T   V   R   Q   F   A   T   R   Y   S   K   K   F   G
```

FIG. 3A

```
      711             720             729             738             747             756
GTT GAC AGA ATC AAG ATG ATG GAG CGT CTG TGG GGA GAC TCT TAC TTC AAC CCA
--- --- --- --- --- --- --- --- --- --- --- --- --- --- --- --- --- ---
 V   D   R   I   K   M   M   E   R   L   W   G   D   S   Y   F   N   P 765             774             783             792             801             810
AAG ACC AAG AAA TGG ACC AAC AAG GAC AAG GAC GCC GCT GGA AAG CCT TTG GAG
--- --- --- --- --- --- --- --- --- --- --- --- --- --- --- --- --- ---
 K   T   K   K   W   T   N   K   D   K   D   A   A   G   K   P   L   E 819             828             837             846             855             864
CGT GCC TTC AAC ATG TTC GTT TTG GAC CCT ATC TTC CGT CTG TTT GCT GCC ATC
--- --- --- --- --- --- --- --- --- --- --- --- --- --- --- --- --- ---
 R   A   F   N   M   F   V   L   D   P   I   F   R   L   F   A   A   I 873             882             891             900             909             918
ATG AAC TTC AAG AAG GAT GAA ATT CCA GTT CTG TTG GAG AAA TTG GAG ATC AAC
--- --- --- --- --- --- --- --- --- --- --- --- --- --- --- --- --- ---
 M   N   F   K   K   D   E   I   P   V   L   L   E   K   L   E   I   N 927             936             945             954             963             972
CTG AAG CGT GAG GAG AAG GAG TTG GAG GGT AAG GCT CTT TTG AAG GTT GTC ATG
--- --- --- --- --- --- --- --- --- --- --- --- --- --- --- --- --- ---
 L   K   R   E   E   K   E   L   E   G   K   A   L   L   K   V   V   M 981             990             999             1008            1017            1026
AGA AAG TTC TTG CCA GCT GCC GAC GCT TTG TTG GAG ATG ATT GTT CTT CAC CTG
--- --- --- --- --- --- --- --- --- --- --- --- --- --- --- --- --- ---
 R   K   F   L   P   A   A   D   A   L   L   E   M   I   V   L   H   L 1035            1044            1053            1062            1071            1080
CCA TCT CCA GTC ACC GCT CAA GCT TAC AGA GCC GAG ACT TTG TAC GAA GGT CCA
--- --- --- --- --- --- --- --- --- --- --- --- --- --- --- --- --- ---
 P   S   P   V   T   A   Q   A   Y   R   A   E   T   L   Y   E   G   P 1089            1098            1107            1116            1125            1134
TCT GAT GAC CAA TTC TGC ATT GGT ATC AGA GAG TGT GAC CCT AAG GCT GAG CTG
--- --- --- --- --- --- --- --- --- --- --- --- --- --- --- --- --- ---
 S   D   D   Q   F   C   I   G   I   R   E   C   D   P   K   A   E   L 1143            1152            1161            1170            1179            1188
ATG GTT TAC ATT TCC AAG ATG GTG CCA ACC TCC GAC AAA GGT AGA TTC TAC GCC
--- --- --- --- --- --- --- --- --- --- --- --- --- --- --- --- --- ---
 M   V   Y   I   S   K   M   V   P   T   S   D   K   G   R   F   Y   A 1197            1206            1215            1224            1233            1242
TTC GGT CGT GTT TTC TCC GGT ACT GTT AAG TCC GGT CAA AAG GTC AGA ATC CAA
--- --- --- --- --- --- --- --- --- --- --- --- --- --- --- --- --- ---
 F   G   R   V   F   S   G   T   V   K   S   G   Q   K   V   R   I   Q 1251            1260            1269            1278            1287            1296
GGT CCT AAC TAC GTT CCA GGT AAG AAG GAG GAC TTG TTC ATC AAG GCT GTT CAA
--- --- --- --- --- --- --- --- --- --- --- --- --- --- --- --- --- ---
 G   P   N   Y   V   P   G   K   K   E   D   L   F   I   K   A   V   Q 1305            1314            1323            1332            1341            1350
AGA ACT GTT TTG ATG ATG GGA AGA ACC GTC GAG CCT ATT GAC GAT GTC CCA GCT
--- --- --- --- --- --- --- --- --- --- --- --- --- --- --- --- --- ---
 R   T   V   L   M   M   G   R   T   V   E   P   I   D   D   V   P   A 1359            1368            1377            1386            1395            1404
GGT AAC ATT CTG GGT ATT GTG GGT ATC GAC CAG TTC TTG CTG AAG TCT GGT ACT
--- --- --- --- --- --- --- --- --- --- --- --- --- --- --- --- --- ---
 G   N   I   L   G   I   V   G   I   D   Q   F   L   L   K   S   G   T

┌►Δ5'EF-2
      1413            1422    |      1431            1440            1449            1458
CTT ACT ACC AAC GAA GCC GCT CAC AAC ATG AAG GTG ATG AAA TTC TCT GTC TCT
--- --- --- --- --- --- --- --- --- --- --- --- --- --- --- --- --- ---
 L   T   T   N   E   A   A   H   N   M   K   V   M   K   F   S   V   S
```

FIG. 3B

```
      1467            1476            1485            1494            1503            1512
CCA GTT GTG CAA GTT GCC GTT GAG GTC AAG AAC GCT AAT GAT CTG CCC AAG TTG
--- --- --- --- --- --- --- --- --- --- --- --- --- --- --- --- --- ---
 P   V   V   Q   V   A   V   E   V   K   N   A   N   D   L   P   K   L 1521            1530            1539            1548            1557            1566
GTT GAG GGT CTG AAG CGT TTG TCC AAG TCT GAC CCA TGT GTT TTA ACC TAC ATC
--- --- --- --- --- --- --- --- --- --- --- --- --- --- --- --- --- ---
 V   E   G   L   K   R   L   S   K   S   D   P   C   V   L   T   Y   I 1575            1584            1593            1602            1611            1620
TCC GAG TCT GGT GAG CAC ATT GTT GCT GGT ACT GGT GAG CTG CAC TTG GAA ATC
--- --- --- --- --- --- --- --- --- --- --- --- --- --- --- --- --- ---
 S   E   S   G   E   H   I   V   A   G   T   G   E   L   H   L   E   I 1629            1638            1647            1656            1665            1674
TGT TTG CAA GAT CTG CAA GAC GAC CAC GCT GGT GTC CCT CTG AAG ATT TCT CCT
--- --- --- --- --- --- --- --- --- --- --- --- --- --- --- --- --- ---
 C   L   Q   D   L   Q   D   D   H   A   G   V   P   L   K   I   S   P 1683            1692            1701            1710            1719            1728
CCA GTT GTT ACC TAC CGT GAG ACT GTC ACT AAC GAA TCT TCC ATG ACT GCC CTG
--- --- --- --- --- --- --- --- --- --- --- --- --- --- --- --- --- ---
 P   V   V   T   Y   R   E   T   V   T   N   E   S   S   M   T   A   L 1737            1746            1755            1764            1773            1782
TCC AAG TCT CAG AAC AAG CAT AAC AGA ATT TAC CTG AAG GCT CAA CCA ATT GAC
--- --- --- --- --- --- --- --- --- --- --- --- --- --- --- --- --- ---
 S   K   S   Q   N   K   H   N   R   I   Y   L   K   A   Q   P   I   D 1791            1800            1809            1818            1827            1836
GAG GAA TTG TCT TTG GCT ATC GAA GAA GGT AAG GTT CAC CCA AGA GAC GAC TTT
--- --- --- --- --- --- --- --- --- --- --- --- --- --- --- --- --- ---
 E   E   L   S   L   A   I   E   E   G   K   V   H   P   R   D   D   F 1845            1854            1863            1872            1881            1890
AAA GCC AGA GCC AGA ATC ATG GCT GAT GAA TAC GGT TGG GAC GTC ACT GAT GCC
--- --- --- --- --- --- --- --- --- --- --- --- --- --- --- --- --- ---
 K   A   R   A   R   I   M   A   D   E   Y   G   W   D   V   T   D   A 1899            1908            1917            1926            1935            1944
AGA AAG ATC TGG TGT TTC GGT CCA GAC GGT ACT GGT GCC AAC TTA GTT GTT GAC
--- --- --- --- --- --- --- --- --- --- --- --- --- --- --- --- --- ---
 R   K   I   W   C   F   G   P   D   G   T   G   A   N   L   V   V   D 1953            1962            1971            1980            1989            1998
CAG TCT AAG GCT GTC CAA TAC TTG CAC GAG ATC AAG GAC TCT GTT GTT GCC GGT
--- --- --- --- --- --- --- --- --- --- --- --- --- --- --- --- --- ---
 Q   S   K   A   V   Q   Y   L   H   E   I   K   D   S   V   V   A   G 2007            2016            2025            2034            2043            2052
TTC CAA TTG GCT ACC AAG GAA GGT CCA ATT TTG GGA GAA AAC ATG AGA TCC GTC
--- --- --- --- --- --- --- --- --- --- --- --- --- --- --- --- --- ---
 F   Q   L   A   T   K   E   G   P   I   L   G   E   N   M   R   S   V 2061            2070            2079            2088            2097            2106
AGA GTC AAC ATC TTG GAT GTT ACC CTG CAC GCC GAT GCT ATC CAC AGA GGT GGA
--- --- --- --- --- --- --- --- --- --- --- --- --- --- --- --- --- ---
 R   V   N   I   L  |D   V   T   L   H   A   D   A   I   H   R   G   G 2115            2124            2133            2142            2151            2160
GGA CAA GTC ATT CCA ACC ATG AAG AGA GTT ACC TAC GCC GCC TTC CTG TTG GCT
--- --- --- --- --- --- --- --- --- --- --- --- --- --- --- --- --- ---
 G   Q   V   I   P   T   M   K   R| V   T   Y   A   A   F   L   L   A 2169            2178            2187            2196            2205            2214
GAG CCA GCT ATC CAG GAG CCT ATC TTC TTG GTG GAG ATC CAA TGT CCA GAG AAT
--- --- --- --- --- --- --- --- --- --- --- --- --- --- --- --- --- ---
 E   P   A   I   Q   E   P   I   F   L   V   E   I   Q   C   P   E   N
```

FIG. 3C

```
      2223            2232            2241            2250            2259            2268
GCC ATT GGT GGT ATC TAC TCT GTT TTG AAC AAG AAG AGA GGT CAA GTT ATC TCT
--- --- --- --- --- --- --- --- --- --- --- --- --- --- --- --- --- ---
 A   I   G   G   I   Y   S   V   L   N   K   K   R   G   Q   V   I   S 2277            2286            2295            2304            2313            2322
GAG GAA CAA AGA CCA GGT ACC CCA TTG TTC ACT GTC AAA GCT TAC TTG CCA GTT
--- --- --- --- --- --- --- --- --- --- --- --- --- --- --- --- --- ---
 E   E   Q   R   P   G   T   P   L   F   T   V   K   A   Y   L   P   V 2331            2340            2349            2358            2367            2376
AAC GAG TCA TTC GGT TTC ACC GGT GAA CTG AGA CAA GCT ACC GCT GGT CAA GCT
--- --- --- --- --- --- --- --- --- --- --- --- --- --- --- --- --- ---
 N   E   S   F   G   F   T   G   E   L   R   Q   A   T   A   G   Q   A 2385            2394            2403            2412            2421            2430
TTC CCA CAG ATG GTG TTC GAC CAC TGG GCC AAC ATG AAT GGT AAC CCA TTG GAC
--- --- --- --- --- --- --- --- --- --- --- --- --- --- --- --- --- ---
 F   P   Q   M   V   F   D   H   W   A   N   M   N   G   N   P   L   D 2439            2448            2457            2466            2475            2484
CCA GCC TCC AAG GTC GGT GAG ATT GTT CTT GCT GCC AGA AAG AGA CAG GGT ATG
--- --- --- --- --- --- --- --- --- --- --- --- --- --- --- --- --- ---
 P   A   S   K   V   G   E   I   V   L   A   A   R   K   R   Q   G   M 2493            2502            2511            2520            2529            2538
AAG GAG AAC GTT CCT GGT TAT GAA GAG TAC TAC GAC AAG TTG TAA GCT TAA TGT
--- --- --- --- --- --- --- --- --- --- --- --- --- --- --- --- --- ---
 K   E   N   V   P   G   Y   E   E   Y   Y   D   K   L 2547            2556            2565            2574            2583            2592
TTC ATT AAC TTA TTT GTG TCG TTC GTA TGT CTA TTT ACG TAC TTA ATT CAG TGT
         A5'EF-2◄

2601
ATT GTT GTT 3'
```

FIG. 3D

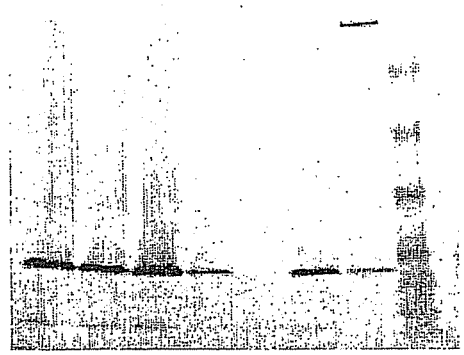
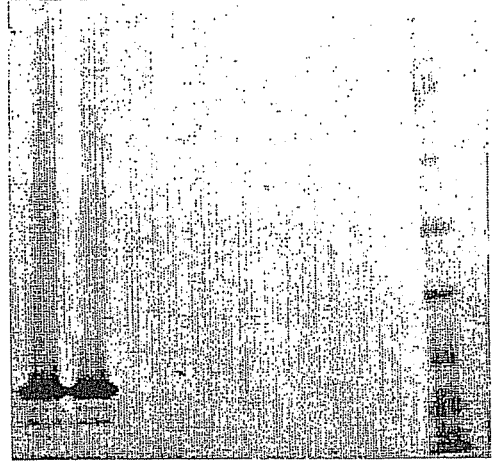
FIG. 6

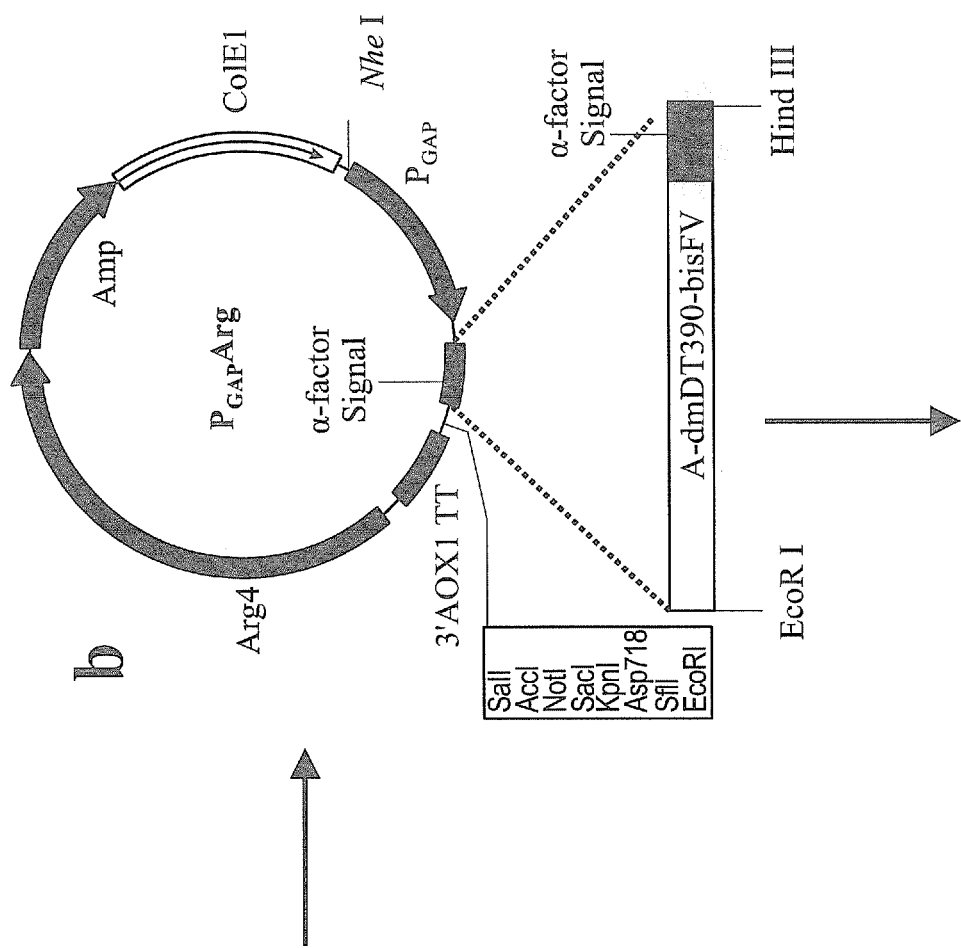
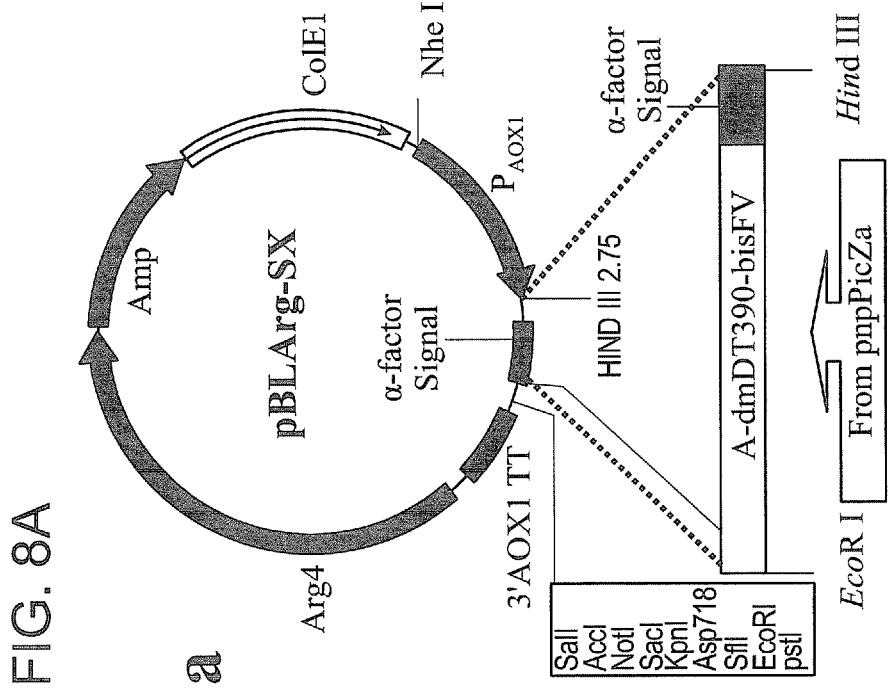
FIG. 8A

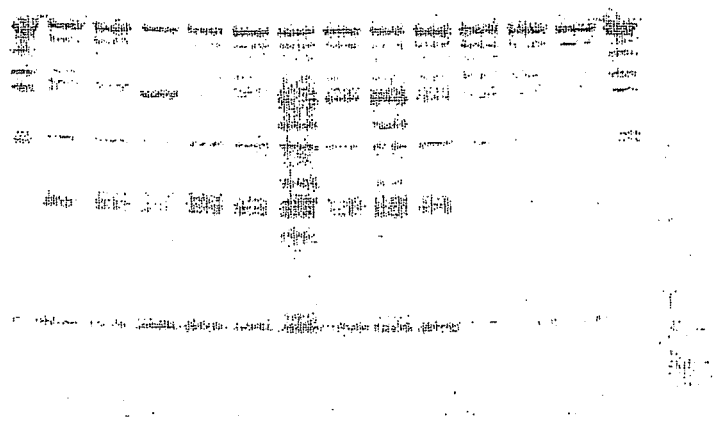
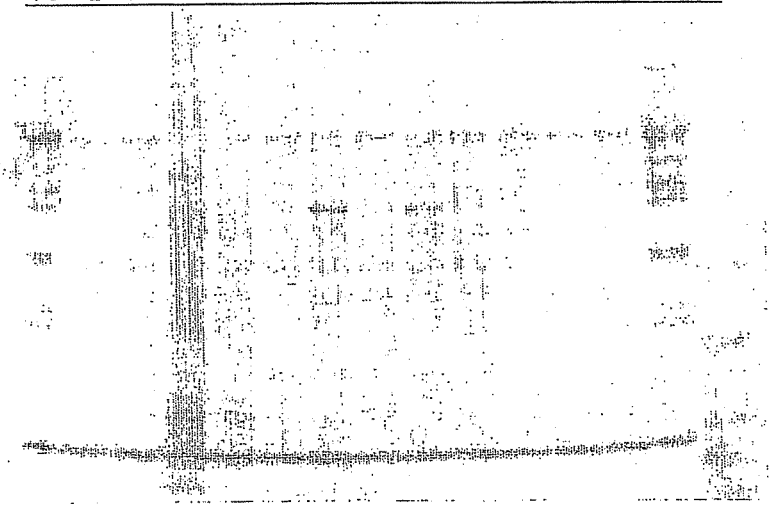
FIG. 9

Lowering agitation speed in fermentation reduces immunotoxin aggregates

Fig. 12

Effect of Tween 20 on aggregation of purified immunotoxin after 20 hrs incubation at 30 C at 250 rpm

Fig. 13

A 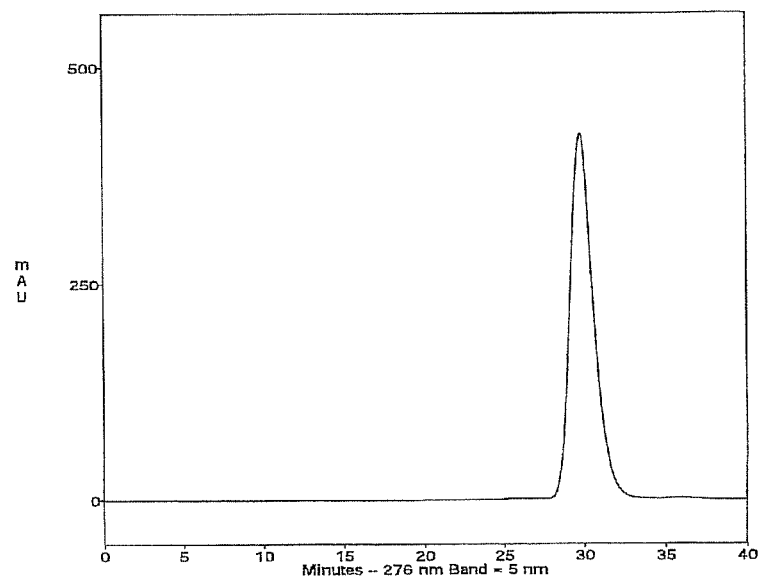 B 
FIG. 19

```
Ala Gly Ala Asp Asp Val Val Asp Ser Ser Lys Ser Phe Val Met Glu
 1               5                  10                  15
Asn Phe Ala Ser Tyr His Gly Thr Lys Pro Gly Tyr Val Asp Ser Ile
            20                  25                  30
Gln Lys Gly Ile Gln Lys Pro Lys Ser Gly Thr Gln Gly Asn Tyr Asp
        35                  40                  45
Asp Asp Trp Lys Gly Phe Tyr Ser Thr Asp Asn Lys Tyr Asp Ala Ala
    50                  55                  60
Gly Tyr Ser Val Asp Asn Glu Asn Pro Leu Ser Gly Lys Ala Gly Gly
65                  70                  75                 ·80
Val Val Lys Val Thr Tyr Pro Gly Leu Thr Lys Val Leu Ala Leu Lys
                85                  90                  95
Val Asp Asn Ala Glu Thr Ile Lys Lys Glu Leu Gly Leu Ser Leu Thr
                    100                 105                 110
Glu Pro Leu Met Glu Gln Val Gly Thr Glu Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                    165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                 210                 215                 220
Gly Pro Ile Lys Asn Lys Met Ser Glu Ser Pro Ala Lys Thr Val Ser
225                 230                 235                 240
Glu Glu Lys Ala Lys Gln Tyr Leu Glu Glu Phe His Gln Thr Ala Leu
                    245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                    325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
                370                 375                 380
His Lys Thr Gln Pro Phe Leu Pro Trp Asp Ile Gln Met Thr Gln Thr
385                 390                 395                 400
Thr Ser Ser Leu Ser Ala Ser Leu Gly Asp Arg Val Thr Ile Ser Cys
                    405                 410                 415
```

FIG. 20A

Arg Ala Ser Gln Asp Ile Arg Asn Tyr Leu Asn Trp Tyr Gln Gln Lys
    420             425             430
Pro Asp Gly Thr Val Lys Leu Leu Ile Tyr Tyr Thr Ser Arg Leu His
    435             440             445
Ser Gly Val Pro Ser Lys Phe Ser Gly Ser Gly Ser Gly Thr Asp Tyr
    450             455             460
Ser Leu Thr Ile Ser Asn Leu Glu Gln Glu Asp Ile Ala Thr Tyr Phe
465             470             475             480
Cys Gln Gln Gly Asn Thr Leu Pro Trp Thr Phe Ala Gly Gly Thr Lys
        485             490             495
Leu Glu Ile Lys Gly Gly Gly Gly Ser Gly Gly Gly Gly Ser Gly Gly
            500             505             510
Gly Gly Ser Glu Val Gln Leu Gln Gln Ser Gly Pro Glu Leu Val Lys
    515             520             525
Pro Gly Ala Ser Met Lys Ile Ser Cys Lys Ala Ser Gly Tyr Ser Phe
    530             535             540
Thr Gly Tyr Thr Met Asn Trp Val Lys Gln Ser His Gly Lys Asn Leu
545             550             555             560
Glu Trp Met Gly Leu Ile Asn Pro Tyr Lys Gly Val Ser Thr Tyr Asn
            565             570             575
Gln Lys Phe Lys Asp Lys Ala Thr Leu Thr Val Asp Lys Ser Ser Ser
        580             585             590
Thr Ala Tyr Met Glu Leu Leu Ser Leu Thr Ser Glu Asp Ser Ala Val
            595             600             605
Tyr Tyr Cys Ala Arg Ser Gly Tyr Tyr Gly Asp Ser Asp Trp Tyr Phe
        610             615             620
Asp Val Trp Gly Ala Gly Thr Thr Val Thr Val Ser Ser Gly Gly Gly
625             630             635             640
Gly Ser Gly Gly Gly Gly Ser Gly Gly Gly Gly Ser Asp Ile Gln Met
                645             650             655
Thr Gln Thr Thr Ser Ser Leu Ser Ala Ser Leu Gly Asp Arg Val Thr
            660             665             670
Ile Ser Cys Arg Ala Ser Gln Asp Ile Arg Asn Tyr Leu Asn Trp Tyr
        675             680             685
Gln Gln Lys Pro Asp Gly Thr Val Lys Leu Leu Ile Tyr Tyr Thr Ser
    690             695             700
Arg Leu His Ser Gly Val Pro Ser Lys Phe Ser Gly Ser Gly Ser Gly
705             710             715             720
Thr Asp Tyr Ser Leu Thr Ile Ser Asn Leu Glu Gln Glu Asp Ile Ala
            725             730             735
Thr Tyr Phe Cys Gln Gln Gly Asn Thr Leu Pro Trp Thr Phe Ala Gly
        740             745             750
Gly Thr Lys Leu Glu Ile Lys Gly Gly Gly Gly Ser Gly Gly Gly Gly
    755             760             765
Ser Gly Gly Gly Gly Ser Glu Val Gln Leu Gln Gln Ser Gly Pro Glu
    770             775             780
Leu Val Lys Pro Gly Ala Ser Met Lys Ile Ser Cys Lys Ala Ser Gly
785             790             795             800
Tyr Ser Phe Thr Gly Tyr Thr Met Asn Trp Val Lys Gln Ser His Gly
            805             810             815
Lys Asn Leu Glu Trp Met Gly Leu Ile Asn Pro Tyr Lys Gly Val Ser
        820             825             830

FIG. 20B

```
Thr Tyr Asn Gln Lys Phe Lys Asp Lys Ala Thr Leu Thr Val Asp Lys
835             840             845
Ser Ser Ser Thr Ala Tyr Met Glu Leu Leu Ser Leu Thr Ser Glu Asp
850             855             860
Ser Ala Val Tyr Tyr Cys Ala Arg Ser Gly Tyr Tyr Gly Asp Ser Asp
865             870             875             880
Trp Tyr Phe Asp Val Trp Gly Gln Gly Thr Thr Leu Thr Val Phe Ser
885             890         896
```

METHODS FOR EXPRESSION AND PURIFICATION OF IMMUNOTOXINS

This application is a divisional application of U.S. application Ser. No. 10/566,886, filed Feb. 1, 2006, (now U.S. Pat. No. 7,892,786, issued Feb. 22, 2011), which is a national stage application filed under 35 U.S.C. §371 of international application No. PCT/US2004/024786, filed Aug. 2, 2004, which claims the benefit of priority under 35 U.S.C. §119(e) to U.S. Provisional Application 60/491,923, filed Aug. 1, 2003.

The U.S. Government has certain rights in the invention.

BACKGROUND OF THE INVENTION

1. Field of the Invention

The present invention relates generally to methods of protein expression and purification, and more specifically, to methods of expression and purification of immunotoxins.

2. Description of the Related Art

The number of organ transplants performed in the United States each year is approximately 24,000 and consists predominantly of kidney transplants (14,000), liver transplants (5,000), heart transplants (2,200), and smaller numbers of pancreas, lung, heart-lung, and intestinal transplants (2002 OPTN/SRTR Annual Report).

Transplant tolerance remains an elusive goal for patients and physicians whose ideal would be to see a successful, allogenic organ transplant performed without the need for indefinite, non-specific maintenance immunosuppressive drugs and their attendant side effects. Many of these patients have been treated with cyclosporin, azathioprine, and prednisone with a variety of other immunosuppressive agents being used for induction or maintenance immunosuppression. The average annual cost of maintenance immunosuppressive therapy in the United States is approximately $11,000 (Immunosuppressive Drugs Coverage Act, National Kidney Foundation, available at www.kidney.org/general/pubpol/ir_mufact.cfm). While these agents are effective in preventing rejection, the side effects of immunosuppressive therapy are considerable. Immunosuppressive therapy induces nonspecific unresponsiveness of the immune system. Recipients are susceptible to infection and there is a risk of malignancy such as in the form of post transplant lymphoproliferative disorders. A major goal in transplant immunobiology is the development of specific immunologic tolerance to organ transplants with the potential of freeing patients from the side effects of continuous pharmacologic immunosuppression and its attendant complications and costs.

A bivalent anti-T cell immunotoxin, A-dmDT390-bisFv (G$_4$S) was developed for tolerance induction for transplantation, T-cell leukemia and autoimmune diseases. The immunotoxin consists of the first 390 amino acid residues of diphtheria toxin (DT390) and two tandem antigen-binding domains (sFv) from the anti-CD3 antibody UCHT1, that are responsible for binding the immunotoxin to the CDR3εγ subunit of the T cell receptor complex. The anti-CD3ε antibody moiety enables the immunotoxin to target specific cells and the diphtheria toxin moiety kills the target cells. The immunotoxin may be utilized to effect at least partial T-cell depletion in order to treat or prevent T-cell mediated diseases or conditions of the immune system.

Administration of an anti-T cell immunotoxin provides an approach for specific immunologic tolerance. It is applicable to new organ transplants and potentially to existing transplants in recipients with stable transplant function. The immunotoxin can provide highly specific immunosuppression and imparts transplant tolerance in primates, without the adverse effects of nonspecific immunosuppressive drugs, anti-lymphocyte serum or radiation. It is a goal in this field to inhibit the rejection response to the point that rejection is not a factor in reducing average life span among transplant recipients.

The methylotrophic yeast *Pichia pastoris* has been used successfully to express heterologous proteins from different origins (Gellissen 2000). As an eukaryote, *Pichia pastoris* has the ability to perform many post-translational protein modifications such as proteolytic processing, folding, disulfide bond formation and glycosylation. Like other yeasts, *Pichia pastoris* offers significant advantages over higher eukaryotic cells such as Chinese hamster ovary (CHO) or baculovirus-infected insect cell expression systems. It is easy to manipulate, has a rapid growth rate and requires inexpensive media. These greatly reduce the production time and cost, especially on a commercial scale. Unlike *Saccharomyces cerevisiae*, *Pichia pastoris* is not a strong fermentor and can be easily cultured to very high cell density of >100 g dry cell weight/liter (Siegel et al., 1989). This, plus the strong AOX1 promoter employed in driving transcription of foreign genes, have made *Pichia pastoris* the system of choice for high levels of expression of heterologous proteins. The AOX1 promoter also has advantages in the expression of foreign proteins that are deleterious to the expressing host because the promoter is tightly regulated and highly repressed under non-methanolic growth conditions. The inducible and tightly regulated AOX1 promoter has allowed successful expression of DT based immunotoxins, in secreted form, in *Pichia pastoris* strains without any mutation to confer a resistance to DT. (Woo et al., 2002). However, diphtheria toxin (DT) is a very potent toxin to all eukaryotic cells if its catalytic domain can find a route to the cytosol. *Pichia pastoris* is inherently sensitive to these toxins.

The prior art teaches methods for growing *Pichia pastoris*. For example, *Pichia pastoris* may be grown in a fermentor. One protocol for *Pichia pastoris* fermentation contains glycerol as the initial carbon source, followed by brief carbon starvation and use of methanol as the carbon source (*Pichia pastoris* Fermentation Using a BioFlo 110 Benchtop Fermentor, New Brunswick Scientific).

Woo et al. disclosed that, when expressing a bivalent anti-human anti-T cell immunotoxin A-dmDT390-bisFv($G_4S$) in *Pichia pastoris*, a buffered complex medium at pH 7.0 with 1% casamino acids provided the highest expression in shake flask culture and that the expression level was improved by adding PMSF in the range of 1 to 3 mM. (25 Protein Expression and Purification 270-82 (2002)).

Sreekrishna disclosed that an increased secretion level was obtained using *Pichia pastoris* in shake flask cultures when the cells were highly aerated and in a buffered medium at pH 6.0 that was supplemented with yeast extract and peptone (Chapter 16, Industrial Microorganisms: Basic and Applied Molecular Genetics (1993)). The growth medium contained yeast nitrogen base with ammonium sulfate, biotin and glycerol buffered to pH 6.0 with potassium phosphate buffer as well as yeast extract and peptone. The induction medium contained methanol in place of glycerol.

In contrast, the present invention provides an improved method of using *Pichia pastoris* to produce an immunotoxin. The immunotoxins expressed and purified in the present invention can be used in a method of inducing immune tolerance. It would be desirable to provide a method of expression and purification that increased the yield of immunotoxins. The present invention addresses this problem and others in the manner described below.

SUMMARY OF THE INVENTION

In one aspect the present invention relates to a method of expressing an immunotoxin in *Pichia pastoris* toxin resistant EF-2 mutant comprising a) growing the *Pichia pastoris* in a growth medium comprising an enzymatic digest of protein and yeast extract; and b) performing methanol induction of the *Pichia pastoris* with a limited methanol feeding of 0.5 to 0.75 ml/min (per 10 L initial medium) during induction, and wherein the methanol induction is at a temperature of below about 17.5° C.

In another aspect, the present invention relates to a method of expressing an immunotoxin in *Pichia pastoris* comprising a) growing the *Pichia pastoris* in a growth medium comprising an enzymatic digest of protein and yeast extract; and b) performing methanol induction of the *Pichia pastoris* with a methanol and glycerol containing feed, wherein the *Pichia pastoris* is contacted with a phenylmethanesulfonyl fluoride and a source of amino acids and wherein the methanol induction is at a temperature of below about 17.5° C.

In yet another aspect, the present invention relates to a method of purifying a non-glycosylated immunotoxin comprising a) loading a solution containing the non-glycosylated immunotoxin onto a hydrophobic interaction column; b) obtaining a first non-glycosylated immunotoxin containing eluant from the hydrophobic interaction column; c) loading the non-glycosylated immunotoxin containing eluant from step (b) onto an anion exchange column; d) obtaining a second non-glycosylated immunotoxin containing eluant from the anion exchange column by eluting the non-glycosylated immunotoxin with a sodium borate solution; e) diluting the concentration of sodium borate in the second non-glycosylated immunotoxin containing eluant from step (d) to about 50 mM or less; f) concentrating the diluted non-glycosylated immunotoxin containing eluant from step (e) over an anion exchange column; and g) obtaining a purified non-glycosylated immunotoxin from the anion exchange column.

It is to be understood that both the foregoing general description and the following detailed description are exemplary and explanatory only and are not restrictive of the invention, as claimed.

BRIEF DESCRIPTION OF THE DRAWINGS

The accompanying drawings illustrate one or more embodiments of the invention and, together with the written description, serve to explain the principles of the invention.

FIG. 1 shows conservation of diphthamide domain and DT-resistant mutations in eukaryotic EF 2s and nucleotide sequence mutations for the substitution of Arg for Gly 701 in *Pichia pastoris* EF-2. The underlined sequences are the site for the restriction enzyme Sac II that resulted from the nucleotide mutations. See SEQ ID NOS: 1-10.

FIG. 2. The 5' end sequence of *Pichia pastoris* EF-2 showing the short intron (SEQ ID NO: 11; mRNA) and (SEQ ID NO: 12; gDNA). The 5' splice site, branch site and 3' splice site are under lined. EF-2 coding sequence is in bold.

FIG. 3. (A) (B) (C) (D) Nucleotide and deduced amino acid sequence of *Pichia pastoris* EF-2 (SEQ ID NO:13). The nucleotide sequence is numbered from the beginning of the initiation codon. Consensus GTP-binding motif in the protein sequence is AHVDHGKST (SEQ ID NO:14), the threonine residue putatively phosphorylated in vivo by EF-2 kinase is circled and the effector domain conserved among all elongation factors is DEQERGITIKSTA (SEQ ID NO:15). The 22 well-conserved residues of the diphthamide domain are boxed.

FIG. 6. Western blot analysis of cytosolic expression of DT-A chain in mutated and wild type *Pichia pastoris* strains. (a) Lanes 1-6 are the cell extracts of 6 independent clones of mutEF2JC307-8 transformed with pPIC3-DtA, +C: The purified A-dmDT390-bisFv. M: SeeBlue plus2 Protein markers (Invitrogen). (b) Cytosolic expression of DT-A chain in cultures of two separated colonies of mut-3 and mut-5 that are mutEF2JC307-8(3) and (5) respectively, C3 and C4. Protein samples are loaded on 4-12% NuPAGE gels (Invitrogen).

FIG. 9. Western blot analysis of expression of A-dmDT390-bisFv. Samples of culture media (a) and cell extracts (b) were loaded on 4-12% NuPAGE gels (Invitrogen). Lanes of +c are purified A-dmDT390-bisFv. Lanes 1-9 were samples of 9 selected clones of mut EF2JC303 transformed with 2 copies of the A-dmDT390-bisFv gene. Lanes 10, 11 and 12 were samples of single copy clones: lane 12 was the non-mutated EF-2 clone JHW#2, lanes 10 and 11 were two of selected clones of mutEF2JC307-8(1) and mutEF2JC307-8(2) that is also called YYL#8-2.

FIG. 12 Lowering agitation speed in fermentation reduces immunotoxin aggregates. Fermentation performed at high agitation speed resulted in more than 50% of the secreted immunotoxin being present in inactive aggregate forms in the supernatants. In addition, aggregates accumulated over induction time. However, lowering agitation speed from 800 rpm to 400 rpm reduced immunotoxin aggregates. Immunotoxin aggregates were maintained at the same level over induction time.

FIG. 13 Effect of TWEEN 20® on aggregation of purified immunotoxin after 20 hrs incubation at 30° C. at 250 rpm.

Using purified immunotoxin, TWEEN 20® prevented the formation of aggregates by agitation. Approximately 50% of the purified immunotoxin was aggregated by incubation at 30° C. at 250 rpm for 20 hours. However, 0.01%-0.04% of TWEEN 20® significantly reduced the aggregation purified immunotoxin by agitation.

Figure 14:
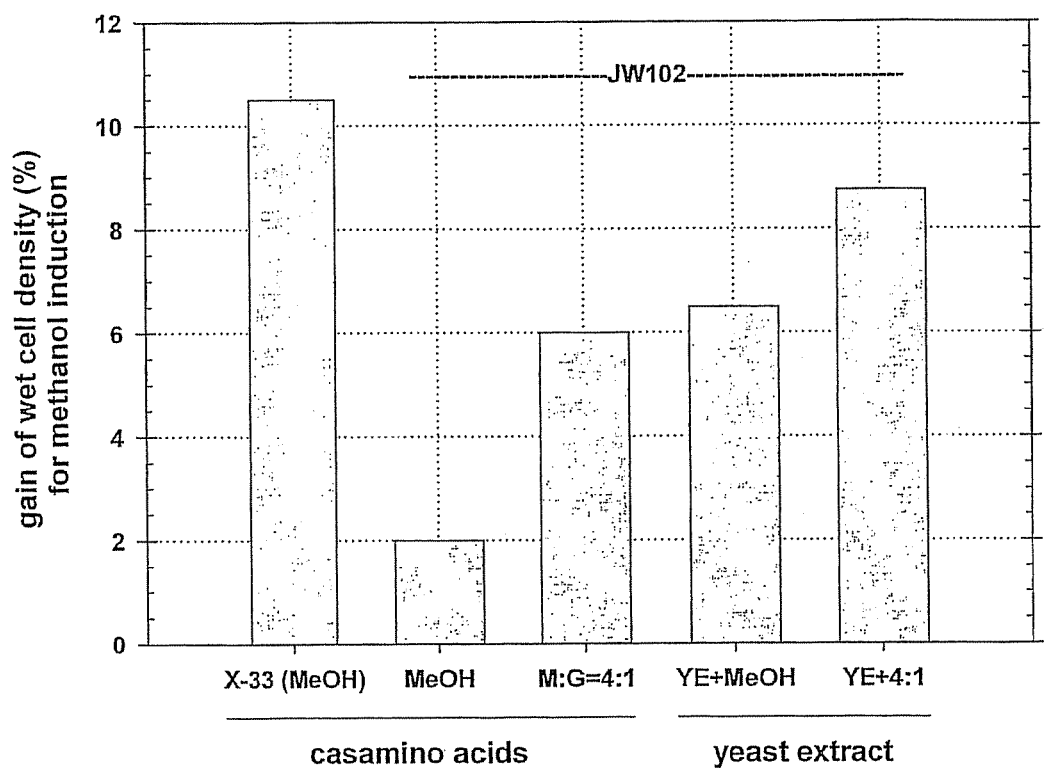

FIG. 14. Change of gain of wet cell density during the first 44 hours of methanol induction. MeOH, methanol alone and feeding of casamino acids; M:G=4:1, methanol/glycerol mixed feeding and feeding of casamino acids; YE+MeOH, feeding of yeast extract and methanol alone; YE+4:1, feeding of yeast extract and methanol/glycerol mixed feeding.

Figure 15A:
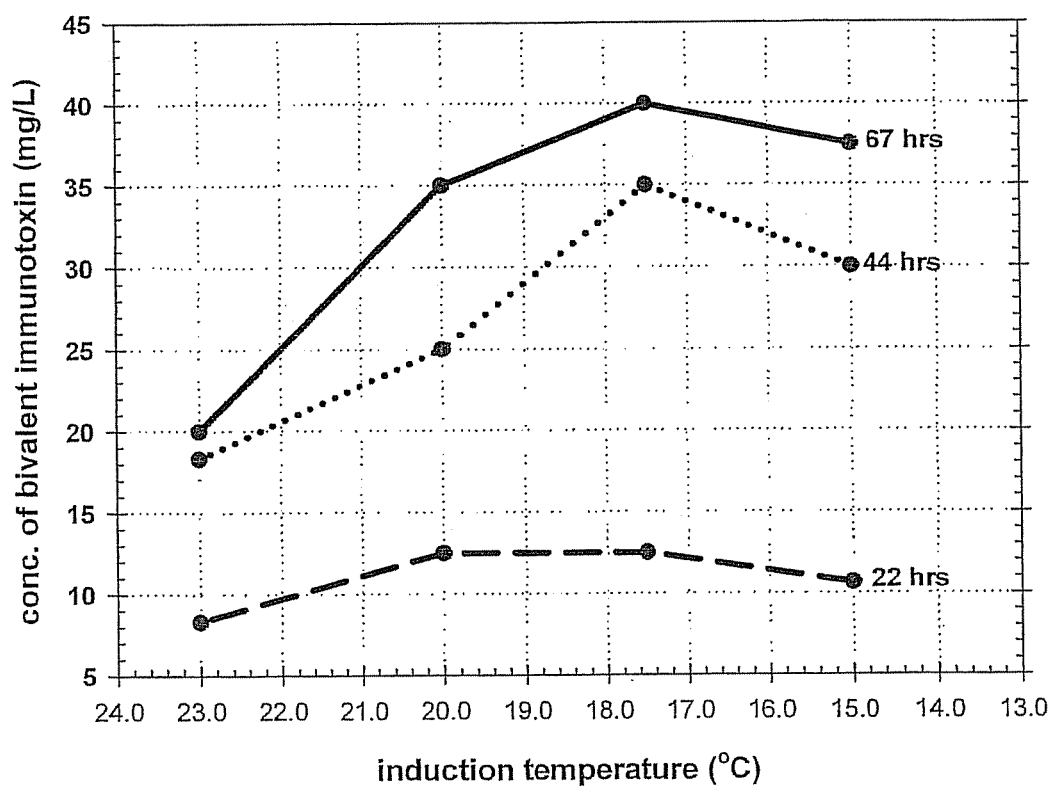
Figure 15B:
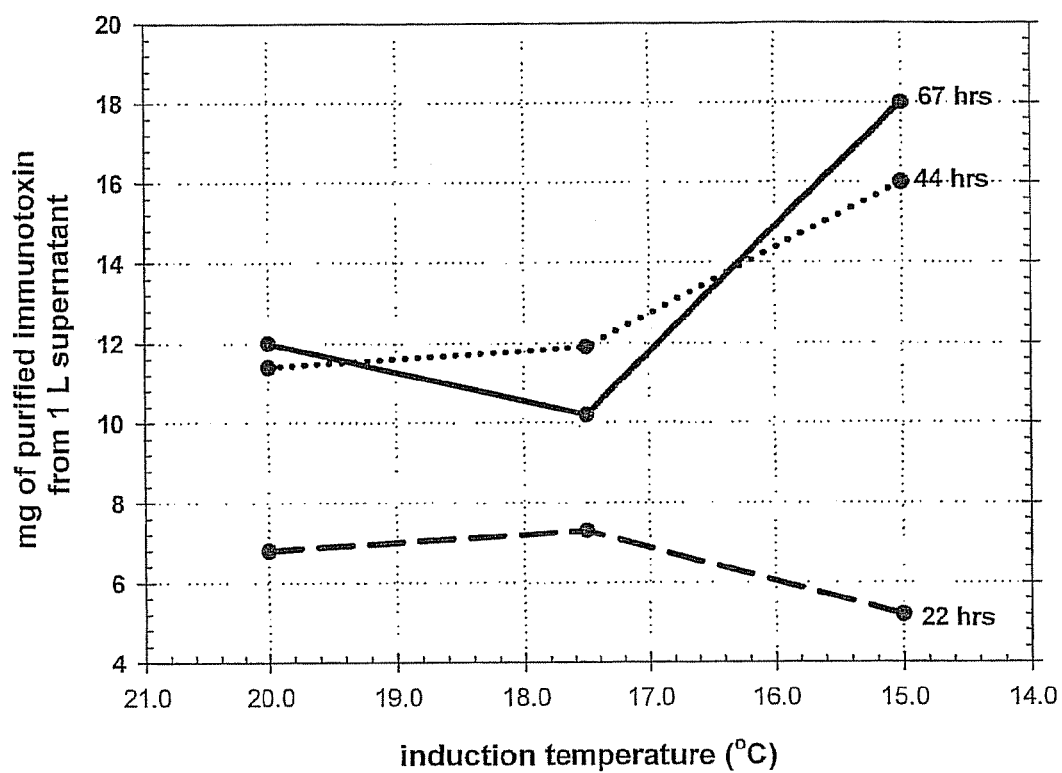

FIG. 15. Expression level of the bivalent immunotoxin and its final purification yield depending on induction temperature. A: change of expression level by induction temperature. B: change of the final purification yield from 1 liter of supernatant taken at 22, 44, and 67 hours of methanol induction. 22 hrs, 44 hrs, and 67 hrs represent time of methanol induction. C: change of methanol consumption depending on induction temperature.

Figure 16:
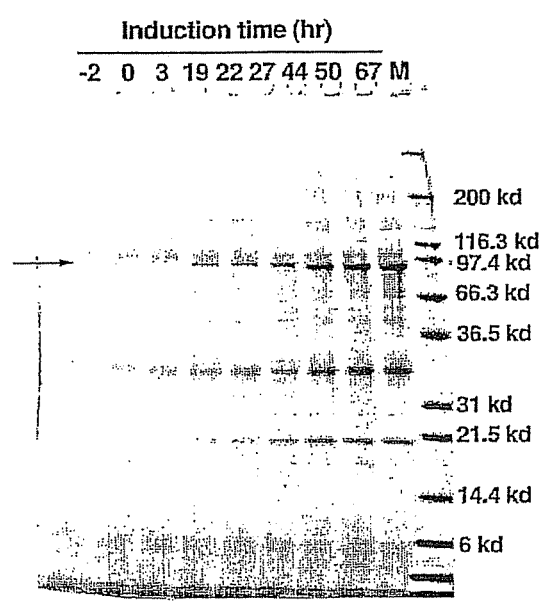

FIG. 16. A representative of optimized fermentation runs. Samples taken at indicated induction time points were fractionated on 4-20% SDS-tris-glycine gel and the gel was stained with Coomassie blue dye. Arrow indicates the position of the bivalent immunotoxin. Mark 12 marker (Invitrogen) was used.

Figure 17:
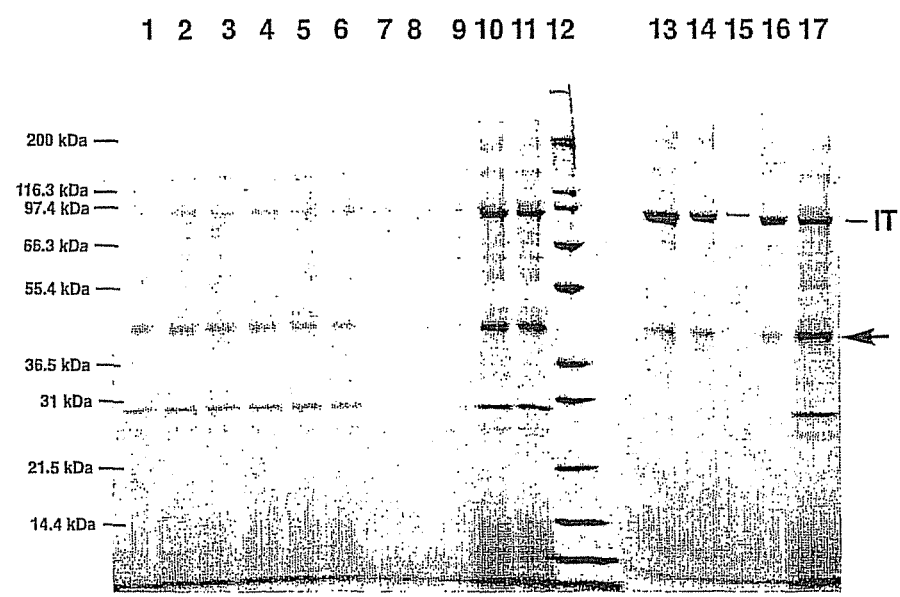

FIG. 17. SDS-PAGE analysis of proteins obtained by butyl 650M capture step. Lane 1~4, sample flow-through fraction #1~#4; lane 5, pooled sample flow-through fractions; lane 6~8, wash fraction #1~#3; lane 9, pooled wash fractions; lane 10, 11, 17, supernatant; lane 12, Mark 12 protein standards (Invitrogen); lane 13~15, eluted fraction #1~#3; lane 16, pooled eluted fractions. IT, immunotoxin.

Figure 18:
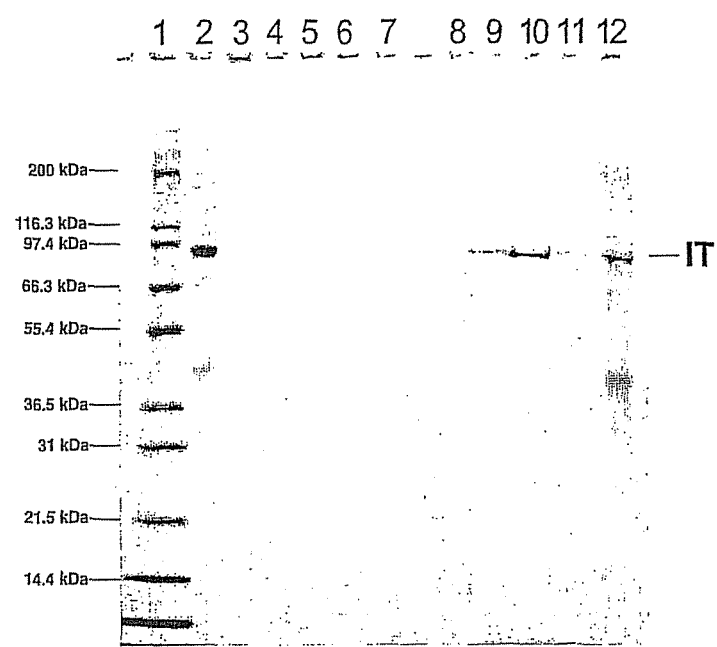

FIG. 18. SDS-PAGE analysis of proteins obtained by Poros 50 HQ borate anion exchange step. Lane 1, Mark 12 protein standards (Invitrogen); lane 2, sample obtained from Butyl 650M HIC step; lane 3~7, sample flow-through fraction #1—#5; lane 8, fraction #1 eluted with 25 mM borate in Buffer B; lane 9, fraction #2 eluted with 50 mM borate in Buffer B; lane 10, fraction #3 eluted with 75 mM borate in Buffer B; lane 11, fraction #4 eluted with 100 mM borate in Buffer B; lane 12, fraction #5 fraction eluted with 1 M NaCl in Buffer B. IT, immunotoxin.

FIG. 19. Analytical gel filtration and SDS-PAGE analysis of purified immunotoxin. A: Chromatogram of Superdex 200 10/300 GL gel filtration. B: Picture of Coomassie-stained SDS-polyacrylamide gel.

FIG. 20. (a) (b) (c) Amino acid sequence of Ala-dmDT390bisFv(UCHT1) (SEQ ID NO:16).

Figure 21:
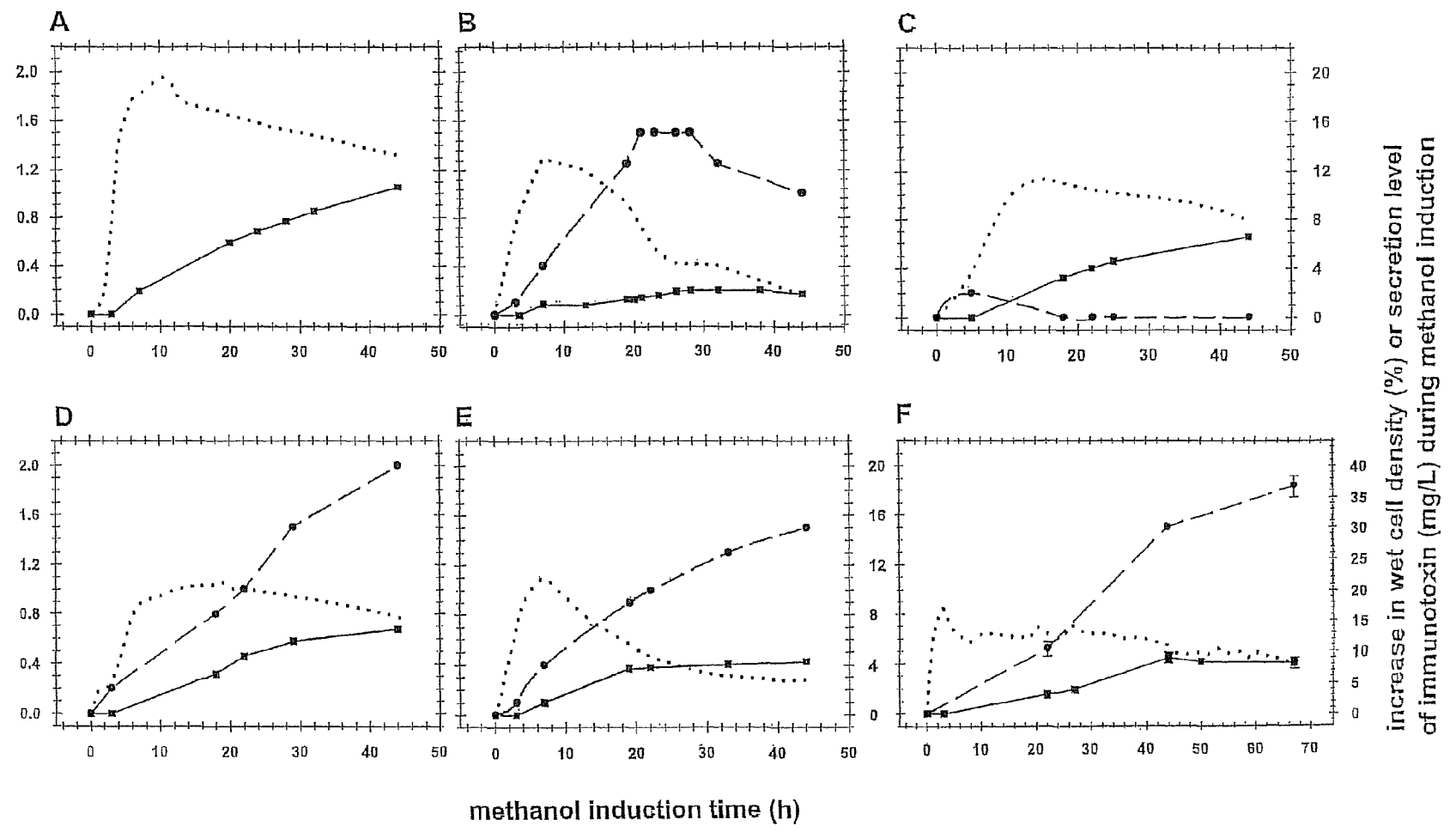

FIG. 21. Comparison of profiles of cell growth, methanol consumption and immunotoxin secretion during methanol induction. Panel A. X-33 strain and the immunotoxin producing toxin resistant EF-2 mutant mutEF2JC307-8(2). These two strains had similar profile of methanol consumption rate and wet cell density gain during methanol induction. The data shown in panel A was for X-33. For the toxin resistant mutant, the maximum methanol consumption rate and wet cell density gain at 44 h of methanol induction was 2.2 ml/rain and 9.17%, respectively. Panels B-F. strain JW102. Constant conditions in all panels A-F were a glycerol batch phase followed by a glycerol-fed batch phase prior to induction. For induction, either pure methanol (MeOH) alone or 4:1 methanol:glycerol (M/G) mixed feed was used. PMSF at 10 mM in methanol was infused continuously during induction. Casamino acid feeding was performed when yeast extract (YE) feeding was not done. Induction conditions: panel A, M/G feeding and no YE feeding; panel B, methanol feeding and no YE feeding; panel C, methanol feeding and YE feeding; panel D, M/G feeding and YE feeding; panel E, M/G feeding and no YE feeding; panel F, M/G feeding and YE feeding. The induction temperature was 23~25° C. in A-E and 15° C. in F (note the right hand axis in panel F is compressed 2-fold compared to the other panels). Methanol consumption rate (ml/min), dotted line; wet cell density (%, w/v), solid line; and level of secreted immunotoxin (mg/L), dashed line. Because of the large amount of work involved in 10 L bioreactor fermentations, it was not practical to replicate the results in panels A-E. The optimized method, panel F, was performed 3 times and the points are averages with standard error of the mean shown when greater than 10%. The actual data points for wet cell density and level of secreted immunotoxin are shown as squares and circles. The actual data points for methanol consumption rate are omitted because methanol consumption rate was measured every minute.

Figure 22:
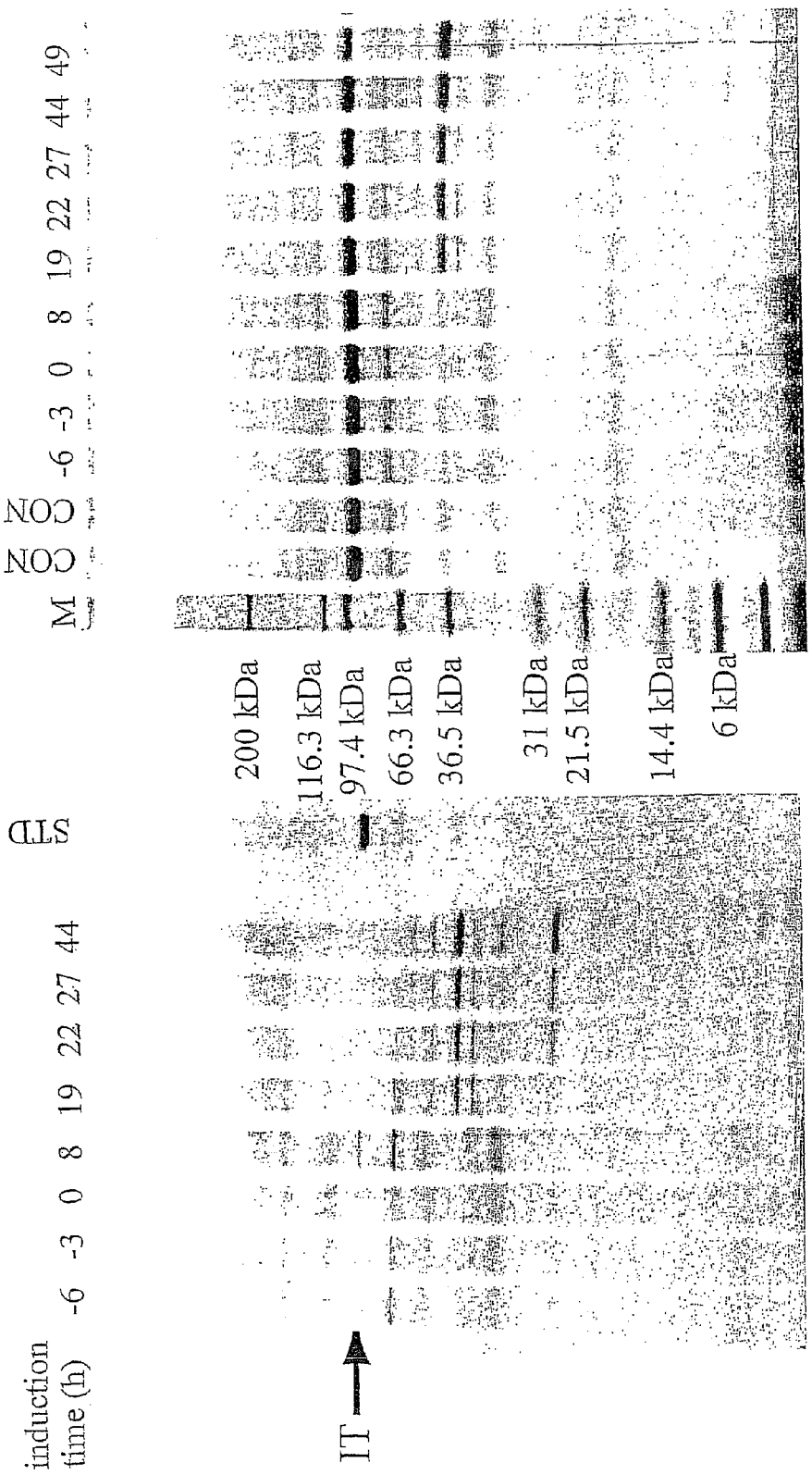

FIG. 22. Protein degradation and immunotoxin production. A. Time course of immunotoxin levels during methanol induction in cultures with methanol and yeast extract feeding (FIG. 21C). The immunotoxin band is marked with IT and an arrow. B. Analysis of residual immunotoxin by SDS-PAGE after incubation (28° C., 20 h, and 250 rpm shaking) of an equal volume of purified immunotoxin (250 µg/ml) with an equal volume of the supernatants collected at the indicated times following methanol induction. Mixtures of equal volumes of purified immunotoxin and PBS buffer or supernatant from 0 h, were used as the controls (CON). Ten µl of the prepared samples were loaded for SDS-PAGE and fractionated on 4-20% SDS-tri-glycine gels under non-reducing conditions. Gels were stained with Coomassie blue dye. Mark12 marker (Invitrogen) was used as the protein marker.

Figure 23:
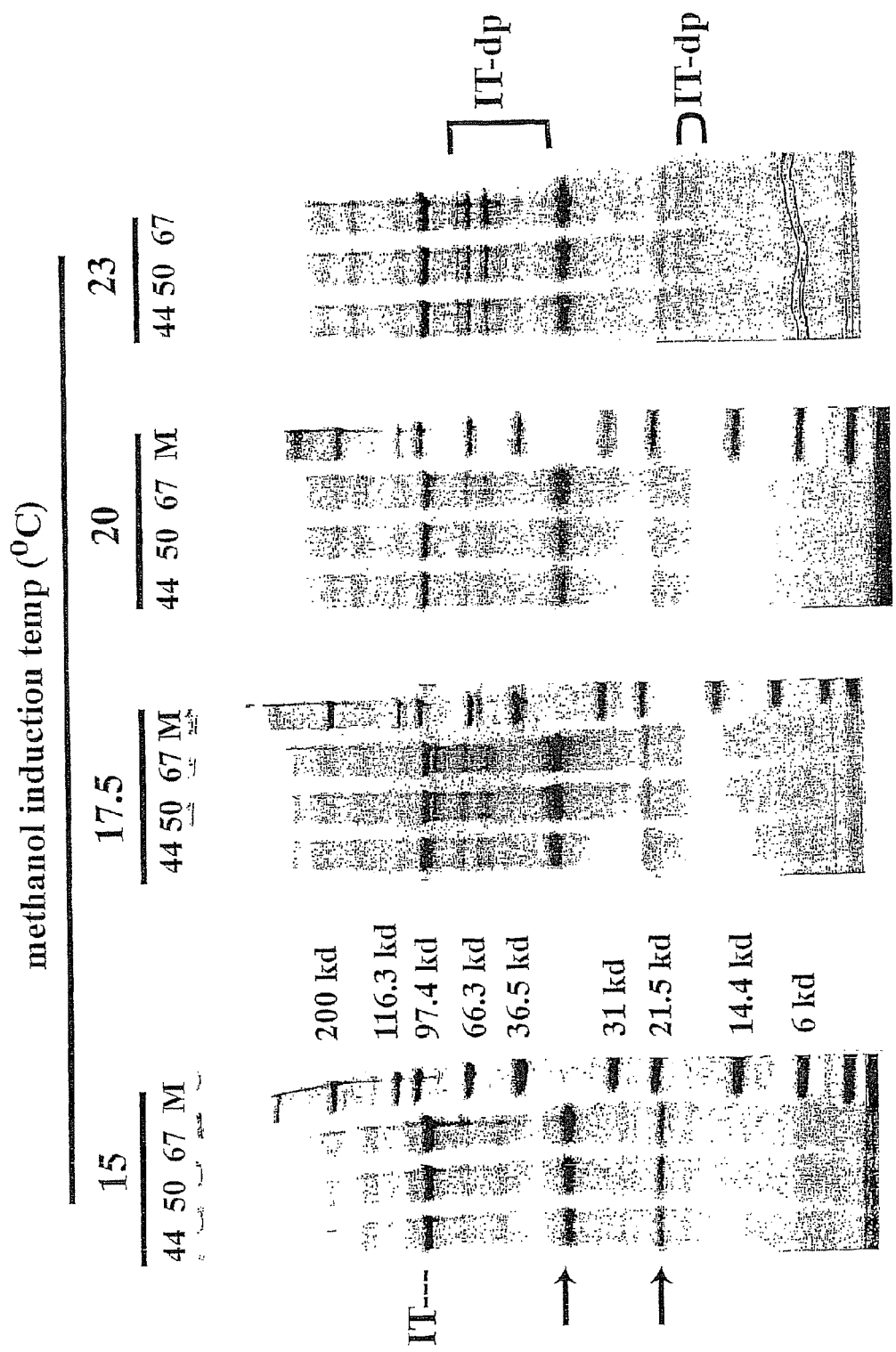

FIG. 23. Effect of temperature on immunotoxin production. Samples taken at indicated induction time points (44, 50, 67 h) from runs at different induction temperature (15~23° C.) were fractionated on 4-20% SDS-tris-glycine gels under non-reducing condition. Continuous feeding of yeast extract and methanol-glycerol feed were used for all runs. The gels were stained with Coomassie blue dye. IT-dp-degraded products of the bivalent immunotoxin. These degradation products were identified by Western blots using anti-DT antibody and anti-$(G_4S)_3$ linker antibody. The anti-$(G_4S)_3$ linker antibody could detect the bivalent immunotoxin and degraded products, because the immunotoxin contained three $(G_4S)_3$ linkers. Arrows point to bands not related to the bivalent immunotoxin. IT—bivalent immunotoxin. Mark12 marker (Invitrogen) was used as the protein marker.

Figure 24:
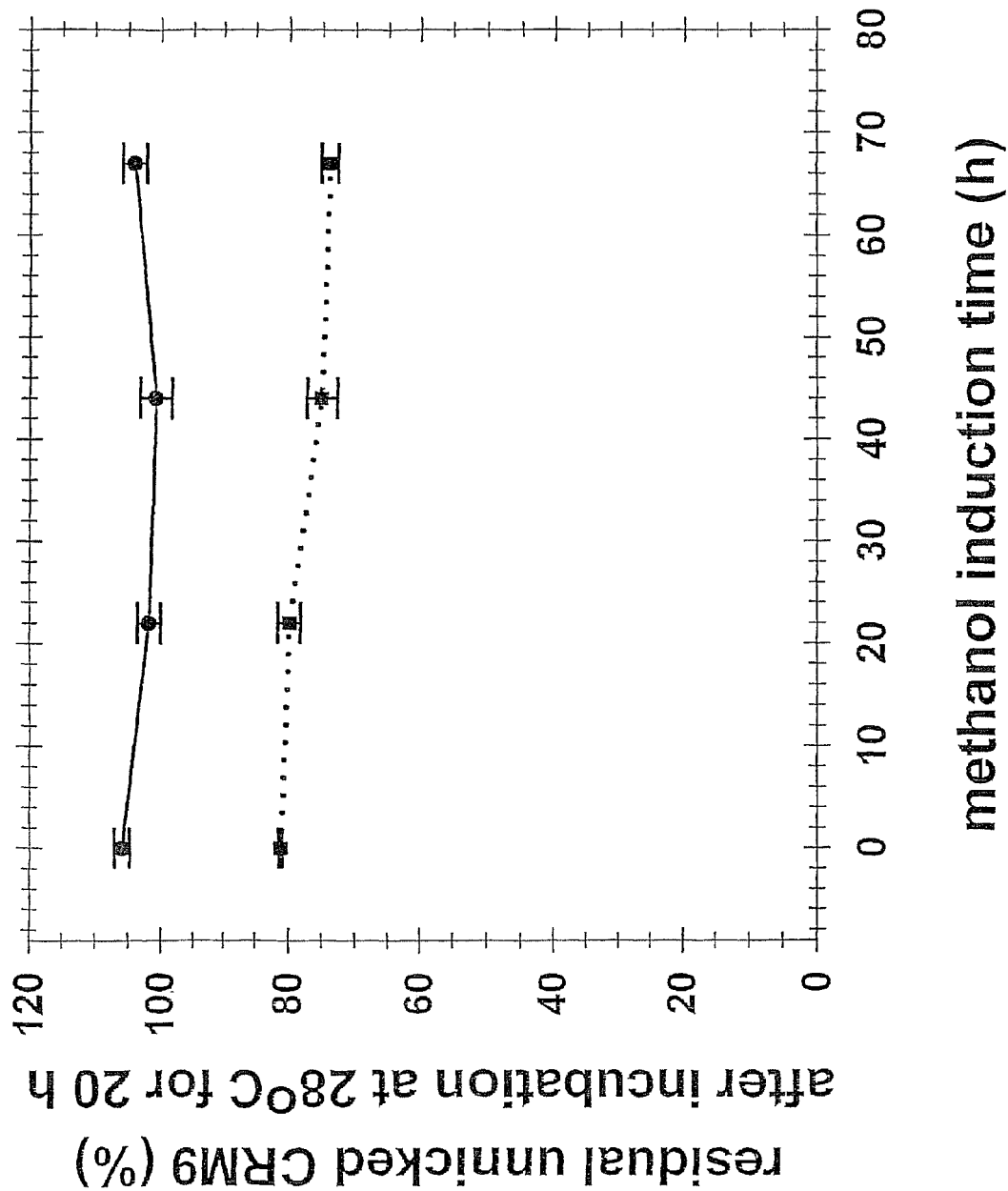

FIG. 24. Analysis of protease activity in supernatants in the absence and presence of PMSF during methanol induction at 15° C. Supernatants were taken at 0, 22, 44 and 67 h of methanol induction from fermentation runs treated with continuous feeding of yeast extract and methanol-glycerol feed. The supernatants were incubated with unnicked CRM9 as the substrate. After incubation, 10 µl of the sample was fractionated on 4~20% SDS-tris-glycine gels under reducing conditions. After staining and drying, the gel was digitized and analyzed for band intensity of unnicked CRM9 by using NIH Image software. PMSF supplementation during methanol induction, solid line; no PMSF, dotted line. Each data point is the average from 3 fermentation runs with the standard error of the mean.

DETAILED DESCRIPTION OF THE INVENTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular aims "a," "an" and "the" include the plural forms unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Contacted" means one substance is placed in physical association with another substance.

"Non-glycosylated" means in the absence of glycosylation or in the absence of glycosylation perceptible using routine methods known in the art for measuring glycosylation. Thus non-glycosylated includes having had glycosylation sites mutated so that glycosylation does not occur, expressing in a system in which glycosylation will not occur or not possessing glyscosylation sites in the wild type state.

"Loading" a column means placing the sample in a position in which at least a portion of the sample will eventually enter the part of the column occupied by the resin.

An "enzymatic digest" refers to hydrolysis of a protein or peptide at peptide bonds by one or more of various enzymes. Such enzymes may include but are not limited to trypsin, chymotrypsin, pepsin, thrombin, papain, bromelain, thermolysin, subtilisin or carboxypeptidase A.

"Yeast extract" is a preparation of peptides and amino acids obtained by proteolysis of the proteins within yeast cells.

"Induction" refers to providing a signal to a given promoter to cause expression of a given gene.

"Feed" refers to providing fresh media or nutrients at a rate that at least partially replaces the media or nutrients as they are depleted.

"Moiety" refers to one portion of a molecule or compound that is divided into multiple portions. In the present invention, moiety may refer a toxin portion or an antibody portion of an immunotoxin.

Throughout this application, the term "bivalent" is used to refer to the ability of a single composition to bind two ligands. For example, an A-dmDT390-bisFv($G_4S$) immunotoxin can bind two CD3 molecules. It is also understood that the term "divalent" can have a similar meaning in the art. Herein, the terms "bivalent" and "divalent" refer to the same property and are used interchangeably.

The invention provides a system for expressing and purifying mutant ADP ribosylating toxins and toxin fusion proteins in a *Pichia pastoris* mutant. The methods of the present invention possess the advantage of being compliant with Good Manufacturing Practices.

As used throughout, optionally, the immunotoxin is a fusion protein. The immunotoxin can comprise a diphtheria toxin moiety. It is understood and herein contemplated that other ADP ribosylating immunotoxins may be used in the present methods. For example, specifically contemplated are fusion proteins wherein the immunotoxin comprises a Psuedomonas exotoxin A moiety. The toxin moiety can be a truncated moiety and/or can comprise mutations as compared to the wild-type toxin.

The immunotoxin can further comprise a CD3 antibody moiety or other antibody moiety. It is also understood that the immunotoxin can comprise a targeting antibody moiety other than the CD3 antibody. One of skill in the art would know which moiety to use with the immunotoxin based on the target cell. For example, a CD22 antibody may be used to direct the immunotoxin fusion protein to B cells.

The invention provides a method of expressing an immunotoxin in *Pichia pastoris* toxin resistant EF-2 mutant comprising growing the *Pichia pastoris* in a growth medium comprising an enzymatic digest of protein and yeast extract; and performing methanol induction at a temperature of below about 17.5° C.

In one aspect, the invention provides a method of expressing an immunotoxin in *Pichia pastoris* toxin resistant EF-2 mutant comprising growing the *Pichia pastoris* in a growth medium comprising an enzymatic digest of protein and yeast extract; and performing methanol induction of the *Pichia pastoris* with a limited methanol feeding during induction of 0.5 to 0.75 ml/min (per 10 L initial medium), wherein the methanol induction is at a temperature of below about 17.5° C.

Alternatively, the invention provides a method of expressing an immunotoxin in *Pichia pastoris* comprising growing the *Pichia pastoris* in a growth medium comprising an enzymatic digest of protein (e.g., soy protein) and yeast extract; and performing methanol induction of the *Pichia pastoris* with a methanol and glycerol containing feed (e.g., with a methanol to glycerol ration of about 4:1), wherein the *Pichia pastoris* is contacted with a phenylmethanesulfonyl fluoride and a source of amino acids (e.g., a yeast extract) and wherein the methanol induction is at a temperature of below about 17.5° C.

The act of contacting *Pichia pastoris* with phenylmethanesulfonyl fluoride and the source of amino acids in the expression method includes contacting the cells with phenylmethanesulfonyl fluoride and the source of amino acids for at least 2 hours, including 2, 3, 4, 5, 6, 7, 8, 9, 10, or more hours or any amount in between. Preferably, the phenylmethanesulfonyl fluoride is dissolved in the 4:1 methanol glycerol induction feed and the concentration does not exceed 10 mM.

The methanol induction temperature is preferably below about 17.5, and even more preferably is about 15° C. Other temperatures at which methane induction can take place in the practice of the present method include 17.0, 16.5, 16.0, 15.5, 14.5, 14.0, 13.5, 13, 12.5, 12° C. or any amounts in between.

Growth medium refers to any substance required for growth of the selected organism. Substances required for growth may include but are not limited to carbon, hydrogen, oxygen, nitrogen, phosphorus, sulphur, potassium, magnesium, calcium, sodium, iron, trace elements and organic growth factors. Various materials may be included in growth medium to provide the required substances. Such substances include but are not limited to simple sugars, extracts such as peptone, soytone, tryptone, yeast extract, carbon dioxide, vitamins, amino acids, purines and pyrimidines. An example of the method of the invention utilizes the presence of an enzymatice digest of soy produced by DIFCO. Another example of the method of the invention utilizes the presence of yeast extract produced by DIFCO. It is understood that yeast extracts and enzymatic digests produced by any manufacturer of such items, for example, New England Biosciences can be used.

In a specific non-limiting example of the method, the composition of the growth medium is about 4% glycerol, about 2% yeast extract, about 2% enzymatic digest of soy protein, about 1.34% yeast nitrogen base with ammonium sulfate and without amino acids, and about 0.43% PTM1 solution. Optionally, the growth medium further comprises an antifoaming agent. More specifically, the antifoaming agent is present at a concentration of about 0.01% or greater. For example, the anti foaming agent can be present at a concentration of 0.07% or any amount between about 0.01% and about 0.07%. The optimum level of antifoaming reagent is chosen as the minimum amount required to reduce the layer of foam above the liquid-air interface to ½ inch or less. Thus, the composition of the growth medium can be about 4% glycerol, about 2% yeast extract, about 2% enzymatic digest of soy protein, about 1.34% yeast nitrogen base with ammonium sulfate and without amino acids, about 0.43% PTM1 solution and about 0.02% antifoaming agent.

It is understood that one of skill in the art will know that the composition of the growth medium may be altered to optimize for maximal growth. Specifically contemplated are changes up to 20% above or below the percentages of the components in the growth medium. Thus herein disclosed is a growth medium, wherein the composition of the growth medium is about 3.2%-4.8% glycerol, about 1.6%-2.4% yeast extract, about 1.6-2.4% enzymatic digest of soy protein, about 1.07-1.61% yeast nitrogen base with ammonium sulfate and without amino acids, and about 0.34%-0.52% PTM1 solution. For example, specifically disclosed is a growth medium, wherein the composition of the growth medium is about 3.6% glycerol, about 2.4% yeast extract, about 1.9% enzymatic digest of soy protein, about 1.43% yeast nitrogen base with ammonium sulfate and without amino acids, and about 0.43% PTM1 solution.

Optionally, the dissolved oxygen concentration in the growth medium is maintained at a value of 40% or higher (e.g., 45%, 50%, 55%, 60%, or 65%) in the expression method of the invention. For example, in the present invention, a glycerol-fed batch phase is employed to obtain high cell density before initiation of methanol induction. The glycerol-fed batch phase is started when the dissolved oxygen rises above 40%. Glycerol is fed whenever the dissolved oxygen rises above 40% and until the level drops below 40%. When the dissolved oxygen rises again after stopping glycerol feeding, the feed is switched to methanol. A rise or spike in dissolved oxygen, DO, level indicates exhaustion of the carbon source. Typically the DO spike is used to indicate depletion of the glycerol used for growth and indicates that a switch to methanol for the induction phase should occur.

Furthermore, the growth step is optionally at a pH of about 3.0-4.0 and the methanol induction step is at a pH of about 6.7-7.4. For example, the growth step is at a pH of 3.5 and the methanol induction step is at a pH of 7.0.

Methanol induction time can be increased to maximize yields. Typical induction times include 22 h, 44 h, 67 h, and 163 h. Inductuion can be as long as 12 days (288 h). Thus, specifically contemplated are methanol inductions that last about 22 h to about 12 days (288 h). For example, it is understood that methanol induction can last 163 h.

Thus an embodiment of the present invention is a method of expressing an immunotoxin in *Pichia pastoris* comprising a) growing the *Pichia pastoris* in a growth medium comprising an enzymatic digest of protein and yeast extract; b) performing methanol induction of the *Pichia pastoris*, wherein the methanol induction comprises a limited methanol feed of 0.5-0.75 ml/min/10 L of initial volume, wherein the induction is performed at a temperature below 17.5° C., antifoaming agent supplied up to 0.07%, and agitation is reduced to 400 RPM, and wherein the induction step is performed for between about 22 and 288 h.

More specifically, an embodiment of the present invention comprises a method of expressing an immunotoxin in *Pichia pastoris* comprising a) growing a *Pichia pastoris* that expresses an immunotoxin in a growth medium comprising about 4% glycerol, about 2% yeast extract, about 2% enzymatic digest of soy protein, about 1.34% yeast nitrogen base with ammonium sulfate and without amino acids, and about 0.43% PTM1 solution, wherein the growth occurs at a pH of about 3.5, and wherein the dissolved oxygen concentration in the growth medium is maintained at a value of 40% or higher; and b) performing methanol induction of the *Pichia pastoris*, wherein the methanol induction comprises a limited methanol feed of 0.5-0.75 ml/min/10L of initial volume, wherein the induction is performed at a temperature is 15° C., wherein the pH is about 7.0, wherein antifoaming agent supplied at 0.02%, wherein the agitation reduced to 400 RPM, and wherein the induction phase is about 163 h.

The bivalent anti-T cell immunotoxin, A-dmDT390-bisFv ($G_4S$), which selectively kills human T cells, was developed for treatment of T-cell leukemia, autoimmune diseases and tolerance induction for transplantation (U.S. patent application Ser. No. 09/573,797, incorporated by reference). The bivalent anti-T cell immunotoxin, A-dmDT390-bisFv($G_4S$), consists of the first 390 amino acid residues (DT390) of diphtheria toxin (DT) and two tandem antigen-binding domains (sFv) from the anti-CD3 antibody UCHT1. Two N-glycosylation sites in the DT390 immunotoxin have been removed by introduction of two mutations (Liu et al., 2000), resulting in a non-glycoprotein with a molecular weight of 96.5 kDa. The immunotoxin can also comprise a linker molecule to join the antibody moiety to the toxin moiety. The linker (L) can be a Gly-Ser linker. The Gly-Ser linker can be but is not limited to (Gly4Ser)n or (Gly3Ser)n. More specifically, the linker can be a (Gly4Ser)$_3$ linker (GGGGSGGGGSGGGGS) (SEQ ID NO: 17), also referred to herein as (G4S), or a (Gly3Ser)$_4$ linker (GGGSGGGSGGGSGGGS) (SEQ ID NO: 18), also referred to herein as (G3S). In a preferred embodiment the immunotoxin comprises A-dmDT390-bisFv(G4S).

The immunotoxin is sensitive to pH levels below 6.0, as shown by the fact that low pH induces an irreversible conformational change in the translocation domain of the DT390 moiety. The translocation domain mediates translocation of the A chain in the DT390 from the endosomes or the plasma membrane to the cytosol in a proton dependent manner. The catalytic A chain is responsible for protein synthesis inhibition by ADP-ribosylation of elongation factor 2 (EF-2) in the cytosol. This inhibition of protein synthesis is toxic to many eukaryotic cells. The pH sensitivity of the immunotoxin restricts the use of cation exchange chromatography and affinity chromatography based on eluting with a low pH buffer.

The use of toxin-resistant eukaryotic cells can overcome the immunotoxin toxicity. However, selection and characterization of toxin-resistant eukaryotic cells are tedious, labor intensive and time-consuming work. Furthermore, the bivalent immunotoxin production in a EF-2 mutant CHO cell expression system was limited to 5 mg/L and could not be increased by selection for multiple gene insertions. Due to this limitation, with three exceptions (12, 20, 25) all recombinant immunotoxin production for therapeutic uses has been limited to E. coli production necessitating denaturation and refolding from inclusion bodies (6). However, refolding of the multi-domain structure of the bivalent immunotoxin from E. coli was inefficient and full bioactivity was not recovered (25). Also, the multi-domain structure of the bivalent immunotoxin hinders efficient production in Escherichia coli. Therefore, the attempt to develop a robust Pichia pastoris production system for the bivalent inamunotoxin was driven by the inadequacy of the existing productions systems.

Pichia pastoris is a good expression system for the bivalent anti-T cell immunotoxin A-dmDT390-bisFv as it provides optimal protein folding compared to prokaryotic expression systems and provides higher yields compared to mammalian cell expression (CHO cells). Antibody fusion proteins require correct disulfide bridges and the endoplasmic reticulum of yeast provides an oxidizing environment like that of eukaryotic antibody producing cells. The multi-domain structure of the bivalent immunotoxin requires a eukaryotic expression system to properly fold this complex protein. Yet most eukaryotes are sensitive to the effects of protein synthesis inhibition upon expression of the immunotoxin. However, a budding yeast, Pichia pastoris has a certain degree of tolerance to DT (Neville et al., 1992; Woo et al., 2002) and yielded the immunotoxin at a level of 40 mg/L in fermentor culture. The immunotoxin was produced by fermentation of genetically engineered Pichia pastoris (JW102, renamed from pJW#2 (Woo et al., 2002)) via the secretory route. As shown in Example 41, the present method provides a yield of 120 mg/l after a 163 h induction period and the purified yield is 90.8 mg/L (see table 6).

After gene optimization to reduce the AT content of the DNA sequence, secreted expression levels under the AOX1 promoter of 25-30 mg/L can be obtained in bioreactors after 24-44 hours of induction. Pichia pastoris was sensitive to the toxic effects of cytosolic expressed diphtheria toxin A chain which ADP ribosylates elongation factor 2 (EF-2) leading to cessation of protein synthesis. Toxicity to expression of A-dmDT390-bisFv by the secretory route was indicated by a continuous fall in methanol consumption after induction. A mixed feed of glycerol and methanol was provided to the cells. Expression of the catalytic domain (A chain) of DT in the cytosol is lethal to Pichia pastoris. When cells bearing the construct A-dmDT390-BisFv (UCHT1) were induced by methanol to express the immunotoxin, nearly 50% were killed after 24 hours (Woo et al., 2002). In contrast, when the same immunotoxin was expressed in CHO cells that had been mutated to DT resistance, no toxic effect was observed (Liu, et al., 2000; Thompson, et al., 2001). In the cytosol of eukaryotes, the catalytic domain of DT catalyzes ADP ribosylation of elongation factor 2 (EF-2), leading to inhibition of protein synthesis and cell death (by protein starvation and or apoptosis, Van Ness et al., 1980; Houchins, 2000). The sensitivity of the eukaryotic EF-2 to ADP-ribosylation by these toxins lies in the structure of protein. EF-2 is a single polypeptide chain of about 850 amino acids and is composed of two domains. The N-terminal G domain is responsible for binding and hydrolysis of GTP that promotes translation, and the C-terminal R (or diphthamide) domain is thought to interact with the ribosome (Kohno et al., 1986; Perentesis et al, 1992). The diphthamide domain (FIG. 1) contains a histidine residue in a region of 22 residues that are well conserved in the EF-2 of all eukaryotes. This conserved histidine is specifically modified post-translationally to the derivative, diphthamide, which is the unique target for ADP-ribosylation by DT (Van Ness et al., 1880). In S. cerevisiae, the conserved histidine can be mutated and substitutions with some other 2 amino acids yielded functional EF-2s that were resistant to ADP-ribosylation (Phan et al., 1993; Kimata and Kohno 1994). However, cells with EF-2 mutated at diphthamide grew more slowly than those expressing wild-type EF-2. In CHO cells, a single substitution of arginine for glycine, which is another well conserved residue located at the 3rd position to the C-terminal side of the diphthamide, also prevented the formation of diphthamide (Kohno & Uchida, 1987; Foley et al., 1992) and resulted in non-ADP-ribosylatable EF-2. This mutation had the same effect on EF-2 of S. cerevisiae (Kimata et al., 1993). In contrast to the mutation at diphthamide, the Gly to Arg mutation in EF-2 did not affect cell growth of CHO and S. cerevisiae (Foley et al., 1992; Kimata and Kohno 1994; Kimata et al., 1993).

In order to determine if the expression level of A-dmDT390-bisFv could be further increased by rendering Pichia pastoris insensitive to toxin, the EF-2 gene of Pichia pastoris has been mutated so that the Gly at position 701 was changed to Arg, which has been shown to prevent ADP-ribosylation of EF-2 in other organisms. The EF-2 mutagenesis required cloning of the gene, introduction of the in vitro mutated sequence with a selection marker, URA3, to the genome and PCR identification of mutated clones. The entire EF-2 gene of Pichia pastoris has been cloned and sequenced. The coding sequence of Pichia pastoris EF-2 is 2526 nucleotides coding for 842 amino acids. The Pichia pastoris EF-2 is the same as the EF-2 of S. cerevisiae and S. pombe in length and shares 88% and 78% of identity in amino acid sequence with these two, respectively. In contrast to these two yeasts, Pichia pastoris has only one copy of the EF-2 gene that contains a short intron. Before the complete sequence of EF-2 was known, different approaches were used to mutate Pichia pastoris to obtain DT resistant strains. All these efforts were unsuccessful due to the lack of robust selection. Based on the EF-2 sequence obtained, a pBLURA-Δ5' mutEF-2 was constructed that targets Pichia pastoris EF-2 gene and introduces a mutation of Gly 701 to Arg to the gene by homologous recombination. The construct contains the 3' end 1028 nucleotides of EF-2 that has been mutagenized in vitro to contain the amino acid substitution and the auxotrophic marker URA3. A PCR detection method was also developed for fast and accurate identification of mutant clones after uracil selection. The targeted mutation strategy with construct pBLURA-Δ5' mutEF-2 allowed mutation of the EF-2 gene of Pichia pastoris with about 40% of uracil positive clones being found to contain the introduced mutations. EF-2 mutants were developed with different auxotrophic markers, (specifically mutEF2JC308 (ade1 arg4 h is 4), mutEF2JC303 (arg4 his4) and mutEF2JC307 (his4)) and demonstrated that the Gly 701 to Arg mutation in EF-2 confers resistance to the cytosolic expression of DT A chain.

When EF-2 mutants were used to express A-dmDT390-bisFv under the control of AOX1 promoter, they did not show the advantage over the non-mutated expressing strain JW102 in the production of the protein in shake-flask. However, in large-scale fermentation culture under conditions adopted from those optimal for JW102, the production of the mutant strain YYL#8-2 [mutEF2JC307-8(2)], increased continuously for 96 hours and reached a level 1.46-fold greater than the non-mutated JW102 strain. Cell growth and methanol consumption rates of the mutant strain expressing A-dmDT390-bisFv were the same as that of the non-expressing wild type strain. Therefore it appeared that expression of A-dmDT390-bisFv was not toxic to the mutant strain. The EF-2 mutants allowed expression of A-dmDT390-bisFv under the control of the constitutive GAP promoter ($P_{GAP}$). In shake-flask culture, the production of A-dmDT390-bisFv under $P_{GAP}$ was about 30% higher than that under $P_{AOX1}$. The increase in production under $P_{GAP}$ may be more significant in fermentation cultures since fermentation allows cells to grow to very high density.

In the *Pichia pastoris* expression system, most heterologous proteins such as botulinum neurotoxin fragments for vaccine use (Potter et al., 2000), hepatitis B surface antigen (Hardy et al., 2000), gelatin (Werten et al., 1999), collagen (Nokelainen et al., 2001), and insulin (Wang et al., 2001) were successfully expressed and/or secreted by using a simple defined medium. The cytosolic expression of the catalytic domain of DT causes protein synthesis inhibition, leading to complete cell death in the defined medium, but not in complex media (Liu et al., 2003). This finding indicates that complex media play a role in attenuation of protein synthesis inhibition that is caused by ADP-ribosylation of EF-2. A very low production of the bivalent immunotoxin was observed in the defined medium but not in a complex medium in shake flask culture. Fermentation of *Pichia pastoris* for expression of heterologous proteins had been developed on the basis of a defined medium but use of complex media for expression of the bivalent immunotoxin in a secreted form provides a higher level of production.

In the present large scale production of bivalent immunotoxin in *Pichia pastoris*, lowering the induction temperature to 15° C. substantially improved the secretion of bioactive immunotoxin, and thereby compensated for the limitation in *Pichia pastoris* secretory capacity. In addition, the use of complex medium containing yeast extract further enhanced immunotoxin secretion, apparently by attenuating the toxic effects of the immunotoxin on the *Pichia pastoris* host.

The expression level of the bivalent immunotoxin was improved by 4-fold in bioreactor culture compared to shake flask culture by optimizing the fermentation conditions in *Pichia pastoris* as follows: (1) use of Soytone Peptone and yeast extract based complex medium, (2) use of methanol/glycerol mixed feed (4:1) to supplement the energy source during methanol induction, (3) continuous feeding of PMSF and yeast extract during induction, and (4) lowering temperature to 15° C. during methanol induction. The lowered temperature resulted in a 2-fold increase in secretion relative to using 23° C. during methanol induction.

As noted above, a major problem in production of the bivalent immunotoxin was reduction of methanol utilization during the methanol induction phase. The reduction of methanol utilization results from a reduction in the activity of the rate limiting enzyme, alcohol oxidase (AOX1). This could be secondary to protein synthesis inhibition by the bivalent immunotoxin reaching the cytosol compartment through leakage from the secretory compartment or by proton dependent translocation from the mildly acidic secretory compartment (Arata et al., 2002). The fact that methanol utilization is not affected by immunotoxin production in a *Pichia pastoris* strain mutated to toxin resistance in the EF-2 gene (Liu et al., 2003) indicates that toxin induced ADP-ribosylation is the cause of the decreased AOX1 activity in strain JW102. However, control of AOX1 level is balanced by both synthesis as well as degradation, and degradative mechanisms could be augmented in response to toxin mediated ADP-ribosylation. For reasons unknown, yeast extract increased methanol utilization, though not to wild type levels. In addition, low methanol utilization negatively affected *Pichia pastoris* cell growth. This was corrected in the present method by adding another carbon source, glycerol, and continuous feeding of yeast extract during methanol induction. These two corrections raised the methanol consumption to 80% of the non-expressing strain.

To further compensate for *Pichia pastoris* protein synthesis inhibition by the expressed immunotoxin, the fermentation conditions were manipulated for full activation of alcohol oxidase I (AOX1), the rate limiting enzyme for methanol metabolism (Veenhuis et al., 1983). Since the immunotoxin gene was under the control of the same strong promoter as the AOX1 gene, the immunotoxin should be highly expressed. However, it has previously been observed in the secretion of heterologous proteins that each protein appears to have an optimal secretion level. Expression beyond the optimal level (overexpression) of secreted heterologous proteins can cause a reduction in secreted protein yields in mammalian, insects and yeast cells (Bannister and Wittrup, 2000; Liebman et al., 1999; Liu et al., 2003; Pendse et al., 1992). In order to determine whether the bivalent immunotoxin was being overexpressed in *Pichia pastoris*, the induction temperature was lowered during methanol induction. Since most cellular activities including protein synthesis are decreased at low temperature, lowering induction temperature should decrease the synthetic rate of the bivalent immunotoxin. Any resulting change in secretion rate was judged. Bivalent immunotoxin expression was increased at low induction temperatures, reaching a maximum at 17.5° C., and secretion of bioactive immunotoxin reached a maximum at 15° C., in spite of the fact that methanol consumption rate at 15° C. fell to 75% of its 23° C. value. Because continuous feeding of PMSF and yeast extract during induction effectively inhibited protease activity in supernatants, it appears unlikely that a reduction in protease activity with lower induction temperature accounts for the nearly 2-fold increase in bivalent immunotoxin secretion seen at 15° C. The limitation in *Pichia pastoris* secretion of bivalent immunotoxin previously described may actually represent an overexpression at 23° C. that is reduced at 15° C. achieving a better balance of input and output within the secretory compartment.

In short, the immunotoxin was produced in *Pichia pastoris* (JW102) via the secretory route under control of the AOX1 promoter in the fermentor using methanol as a carbon source. There were two major impediments to efficient immunotoxin production, the toxicity of the immunotoxin towards *Pichia pastoris* and the limited secretory capacity of *Pichia pastoris* for the immunotoxin. The toxicity towards *Pichia pastoris* resulted in a decrease in the metabolic rate of methanol consumption, a cell growth rate reduction and very low productivity in a defined medium during methanol induction. These problems were overcome by (1) using an enzymatic digest of soy protein (e.g., Soytone peptone) and yeast extract based complex medium, (2) using methanol/glycerol mixed feed (4:1) to supplement energy source during methanol induction, and (3) continuously feeding PMSF and yeast extract during methanol induction. Lowering the induction temperature to 15° C. improved secreted immunotoxin yield by almost 2-fold, up to 40 mg/L (at 67 hours induction) compared to secretion at a induction temperature of 23° C., even though methanol consumption was reduced. In addition, with the use of the present method, the fraction of immunotoxin present as biologically inactive oligomeric forms was decreased.

Also provided by the invention is a method of purifying a non-glycosylated immunotoxin comprising (a) loading a solution containing the non-glycosylated immunotoxin onto a hydrophobic interaction column; (b) obtaining a first non-glycosylated immunotoxin containing eluant from the hydrophobic interaction column; (c) loading the non-glycosylated immunotoxin containing eluant from step (b) onto an anion exchange column; (d) obtaining a second non-glycosylated immunotoxin containing eluant from the anion exchange column by eluting the non-glycosylated immunotoxin with a sodium borate solution; (e) diluting the concentration of sodium borate in the second non-glycosylated immunotoxin containing eluant from step (d) to about 50 mM or less; (f) concentrating the diluted non-glycosylated immunotoxin containing eluant from step (e) over an anion exchange column; and (g) obtaining a purified non-glycosylated immunotoxin from the anion exchange column. Optionally, the method further comprises washing the anion exchange column with about 25 mM sodium borate solution prior to eluting with the sodium borate solution. Preferably the non-glycosylated immunotoxin being purified is expressed by the methods taught herein.

The concentration of the sodium borate solution in step (d) of the purification method is between about 25 mM and about 200 mM, and preferably is between about 75 mM and about 100 mM. For example, the concentration of sodium borate in step (e) can be about 20 mM.

A major problem encountered in the large scale purification of the bivalent anti-T cell immunotoxin, A-dmDT390-bisFv($G_4S$), from *Pichia pastoris* supernatants is the presence of host glycoproteins exhibiting similar charge, size and hydrophobicity characteristics. This problem was overcome by employing borate anion exchange chromatography. Borate anion has an affinity for carbohydrates and imparts negative charges to these structures. At a concentration of sodium borate between 50 and 100 mM, the non-glycosylated immunotoxin did not bind to Poros 50 HQ anion exchanger resin, but glycoproteins, including aggregates related to the immunotoxin, did bind. By using this property of the immunotoxin in the presence of sodium borate, a 3-step purification procedure was developed: (1) Butyl 650M hydrophobic interaction chromatography, (2) Poros 50 HQ anion exchange chromatography in the presence of borate, and (3) Q anion exchange chromatography. This procedure has several advantages: (1) it is a relatively simple process without any dialysis or diafiltration step; (2) it exhibits good repeatability; (3) the final yield is over 50%; and (4) the final purity is over 98%. Previously, boronic acid resins have been used to separate glycoproteins from proteins. However, combining borate anion with conventional anion exchange resins accomplishes separation of the immunotoxin from glycoproteins, and eliminates the need to evaluate non-standard resins with respect to good manufacturing practice guidelines. Thus, borate anion exchange chromatography was used for separation of the immunotoxin from *Pichia pastoris* glycoproteins.

The immunotoxin is functionally active only in its monomeric form. However the supernatant harvested from the fermentation run contained monomeric, dimeric and higher oligomeric forms of the immunotoxin as well as *Pichia pastoris* proteins.

Among these *Pichia pastoris* proteins, a glycoprotein species of approximately 45 kDa was present in dimeric form (~90 kDa). The dimeric and higher oligomeric forms of the immunotoxin were relatively easy to separate by the use of conventional hydrophobic interaction chromatography and anion exchange chromatography. However, it was difficult to isolate the pure monomeric immunotoxin because the 45 kDa glycoproteins were very similar to the monomeric immunotoxin in size, hydrophobicity, and isoelectric point.

Previously, immobilized phenylboronate resins have been used for separation of glycoproteins from proteins (Myohanen et al., 1981; Bouritis et al., 1981; Williams et al., 1981; Zanette et al., 2003). These immobilized resins bind and selectively retard glycoproteins depending on pH, presence of sugar, type of sugar, concentration of sugar and buffer species. Borate anion exchange chromatography is used rather than the immobilized phenylboronate affinity chromatography for separation of the immunotoxin from the 45 kDa glycoprotiens, because of poor separation capability of phenylboronate resin. Borate forms complexes with sugar residues having vicinal cis-hydroxyl groups (Boeseken, 1949) and these complexes are reversible (Weigel, 1963). Reversible complex formation of borate with carbohydrate on glycoproteins resulted in an increased negative charge of the glycoproteins. This property allowed separation of non-glycoproteins and glycoproteins on anion exchange chromatography (Nomoto et al., 1982; Nomoto and Inoue, 1983).

In the separation of the immunotoxin from glycoproteins, borate anion exchange chromatography had different binding characteristics from phenylboronate affinity chromatography. In phenyloboronate affinity chromatography, glycoproteins as well as the immunotoxin were bound under the condition of low ionic strength and they were co-eluted by either 0-100 mM sodium borate gradient or 0-50 mM sorbitol gradient, indicating that the immunotoxin physically interacts with at least one of the bound glycoproteins, or interacts with the phenylboronate column through an alternate mechanism. The fact that purified bivalent immunotoxin also bound to the phenylboronate column indicates binding through an alternate mechanism.

In previous purification methods utilizing shake flask culture, a 2-step procedure was employed which involved DEAE anion exchange chromatography and Protein L affinity chromatography for purification of the immunotoxin (Woo et al., 2002). However, the supernatants of high density fermentor cultures of *Pichia pastoris* contain materials that severely reduce the capacity of anion exchange resins. In addition, the Protein L affinity step required excessive column size, was expensive and was not available under Good Manufacturing Practices (GMP) certification. Consequently, alternative procedures were developed. Hydrophobic interaction chromatography using Butyl 650M worked well as a capture step but also concentrated *P. pastoris* glycoproteins having similar charge, size and hydrophobicity as the immunotoxin. Concanavalin A affinity resin was promising for glycoprotein removal, but bleeding of potentially toxic concanavalin A from the resin resulted in unacceptable contamination of the final product.

The anion exchange column may be but is not limited to an anion acrylic, anion agarose, anion cellulose, anion dextran or anion polystyrene. The preferred anion exchange columns are a Poros HQ 50 and a Q anion exchange column. By using the Poros 50 HQ borate exchange chromatography in the present invention, substantial purification of the monomeric form of the immunotoxin was obtained, even though the immunotoxin in the eluted faction was diluted. Thus, a subsequent concentration step by Q anion exchange chromatography was used.

The hydrophobic interaction column may be but is not limited to a Phenyl-SEPHAROSE® CL-4B, Octyl Agarose, Phenyl-Sepharose 6 Fast Flow, Phenyl-Agarose, Phenyl-Sepharose 6 Fast Flow, Octyl-Sepharose 4 Fast Flow, Butyl Sepharose™ 4 Fast Flow, Octyl Agarose, Phenyl-Agarose, Hydrophobic chromatography media—monoamino MAA-8, Hexyl-Agarose, Dodecyl-Agarose, Hexyl-Agarose, 4-Phenylbutylamine-Agarose, Ethyl-Agarose, Matrix, Butyl-Agarose, Propyl Agarose, Affinity chromatography media AAF-8, Octyl Agarose, Butyl-Agarose, Decyl-Agarose, Phenyl-Agarose, Methyl Matrix: Ceramic HyperD F Hydrogel Composite, Octyl Agarose, Trityl-Agarose, Q Sepharose, Ether 650, Phenyl 650, Butyl 650 or Hexyl 650. The preferred hydrophobic interaction column is a Butyl 650M hydrophobic interaction column.

The present borate anion exchange chromatography is useful for the purification of other *Pichia pastoris* expressed proteins. *Pichia pastoris* is being increasingly used as an expression system for therapeutic recombinant proteins (Cereghino et al., 2002). Many of these recombinant proteins have their glycosylation sites removed due to the profound differences in glycosylation patterns between *Pichia pastoris* and humans. These recombinant proteins are then amenable to purification using borate anion exchange chromatography.

It is contemplated that any buffer, flow rate, and column size may be used that would successfully effect elution of the immunotoxin in a more pure state than the immunotoxin was loaded upon the column.

An immunotoxin used in the present invention comprises a mutant toxin moiety (e.g., DT toxin) linked to an antibody moiety (targeting moiety). Toxins that may be used include but are not limited to diphtheria toxin, ricin toxin, and pseudomonas exotoxin. The antibody moiety is preferably a single chain (sc) variable region.

The practice of the present invention will employ, unless otherwise indicated, conventional techniques of molecular biology, microbiology, recombinant DNA, protein chemistry and immunology, which are within the skill of the art. Such techniques are explained fully in the literature, including Sambrook, et al., MOLECULAR CLONING: A LABORATORY MANUAL 2nd ed. (Cold Spring Harbor Laboratory Press, 1989); DNA CLONING, Vol. I and II, D. N Glover ed. (IRL Press, 1985); OLIGONUCLEOTIDE SYNTHESIS, M. J. Gait ed. (IRL Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, METHODS IN ENZYMOLOGY, Academic Press, Inc.; GENE TRANSFER VECTORS FOR MAMMALIAN CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEMICAL METHODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I-IV, D. M. Weir et al., (Blackwell Scientific Publications, 1986); Kitts et al., Biotechniques 14:810-817 (1993); Munemitsu et al., Mol. and Cell. Biol. 10:5977-5982 (1990).

The present invention utilizes a nucleic acid encoding a diphtheria toxin-containing fusion protein, wherein the nucleic acid can be expressed by a yeast cell. The nucleic acid capable of being expressed by yeast, comprises a modified native diphtheria-encoding sequence. To promote expression of the nucleic acids of the present invention by yeast cells, regions of the nucleic acid rich in A and T nucleotides are modified to permit expression of the encoded immunotoxin fusion protein by yeast. For example, such modifications permit expression by *Pichia pastoris*. The modifications are designed to inhibit polyadenylation signals and/or to decrease early termination of RNA transcription. More specifically, one or more AT rich regions of the native diphtheria-encoding sequence are modified to reduce the AT content. The AT rich regions include regions of at least 150 contiguous nucleotides having an AT content of at least 60% or regions of at least 90 contiguous nucleotides having an AT content of at least 65%, and the AT content of the AT rich regions is preferably reduced to 55% or lower. The AT rich regions also include regions of at least 150 contiguous nucleotides having an AT content of at least 63% or regions of at least 90 contiguous nucleotides having an AT content of at least 68%, and the AT content of the AT rich regions is reduced to 55% or lower. The native diphtheria-encoding sequence preferably is further modified to encode a diphtheria toxin truncated at its C-terminal. Furthermore, the native diphtheria-encoding sequence preferably is further modified to encode one or more amino acids prior to the amino terminal glycine residue of the native diphtheria toxin. Furthermore, the native diphtheria-encoding sequence preferably is further modified to encode the alpha mating factor signal peptide or a portion thereof.

The immunotoxin of the present invention may be expressed in and purified from various organisms. These organisms include yeast such as *Pichia pastoris* or *Saccharomyces cerevisiae*, bacteria such as *Escherichia coli*, mammalian cells such as Chinese hamster ovary cells or baculovirus infected insect cells. There are several advantages to yeast expression systems, which include, for example, *Saccharomyces cerevisiae* and *Pichia pastoris*. First, evidence exists that proteins produced in a yeast secretion systems exhibit correct disulfide pairing. Second, efficient large scale production can be carried out using yeast expression systems. The *Saccharomyces cerevisiae* pre-pro-alpha mating factor leader region can be used to direct protein secretion from yeast (Brake, et al. (82)). The leader region of pre-pro-alpha mating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast.

Diphtheria toxin is toxic to yeast when the toxin A chain is synthesized within the cytosol compartment without a secretory signal (Parentesis et al., 1988). This toxin-catalyzed activity is specific for EF-2 and occurs at a unique post-translational histidine residue at the position 699, found in a conserved amino acid sequence in the EF-2 of all eukaryotes. A change of glycine to arginine residue at the position 701 in yeast EF-2 results in resistance to DT.

In an alternative purification method, (Ala)dmDT390-bisFv(UCHT1) was produced in the Pichia medium at a level of 5 mg/ml whether or not the mutant EF-2 gene was present. There is an extremely tight coupling between the presence of the alpha-mating factor signal sequence and the compartmentalization of (Ala)dmDT390-bisFv(UCHT1) into the secretory pathway and away from the EF-2 toxin substrate in the cytosol compartment, since one molecule of toxin in the cytosol can inactivate 99% of the EF-2 in 24 hours. Producing (Ala)dmDT390-bisFv(UCHT1) in Pichia utilizing the alpha-mating factor signal sequence without mutating the Pichia to toxin resistance provided a successful outcome. Another combination of a yeast produced toxin (ricin A chain) and signal sequence, Kar2, resulted in death of the producing cells (Simpson et al., 1999 (80)). It is possible that, at higher gene dosages of immunotoxin fusion protein in Pichia, mEF-2 may confer a benefit in production. A further advantage of yeast over mammalian cells for immunotoxin fusion protein production is the fact that intact yeast are highly resistant to diphtheria toxin present in the external medium to levels as high as $3.3 \times 10-6$ M. Evidently the yeast capsule prevents retrograde transport of toxin back into the cytosol compartment as occurs in mammalian cells and in yeast spheroplasts (Chen et al. 1985).

The invention may utilize a cell comprising a nucleic acid that encodes the immunotoxin fusion protein. The cell can be a prokaryotic cell, including, for example, a bacterial cell. More particularly, the bacterial cell can be an E. coli cell. Alternatively, the cell can be a eukaryotic cell, including, for example, a Chinese hamster ovary (CHO) cell (including for example, the DT resistance CHO-K1 RE 1.22c cell line, as selected by Moebring & Moehring), myeloma cell, a Pichia cell, or an insect cell. The immunotoxin fusion protein coding sequence can be introduced into a Chinese hamster ovary (CHO) cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

The nucleic acids used in the present invention can be operatively linked to one or more of the functional elements that direct and regulate transcription of the inserted nucleic acid and the nucleic acid can be expressed. For example, a nucleic acid can be operatively linked to a bacterial or phage promoter and used to direct the transcription of the nucleic acid in vitro.

A mutant strain of Pichia pastoris is provided. The mutant strain comprises a mutation in at least one gene encoding elongation factor 2 (EF2). This mutation comprises a Gly to Arg replacement at a position two residues to the carboxyl side of the modified histidine residue diphthamide. In this manner, the strain is made resistant to the toxic ADP-ribosyating activity of diphtheria toxin.

A method of expressing a diphtheria toxin protein moiety is provided. Such a method of the invention comprises transfecting a mutated Pichia pastoris cell of the invention with a vector comprising a toxin protein-encoding nucleic acid under conditions that permit expression of the protein-encoding nucleic acid in the cell. The conditions are those used for Pichia pastoris cells and can be optimized for the particular system.

The antibody moiety preferably routes by the anti-CD3 pathway or other T cell epitope pathway. The immunotoxin can be monovalent, but bivalent antibody moieties are presently preferred since they have been found to enhance cell killing by about 15 fold. It is contemplated that any number of chemical coupling or recombinant DNA methods can be used to generate an immunotoxin of the invention. Thus, reference to a fusion toxin or a coupled toxin is not necessarily limiting. The immunotoxin can be a fusion protein produced recombinantly. The immunotoxin can be made by chemical thioether linkage at unique sites of a recombinantly produced bivalent antibody (targeting moiety) and a recombinantly produced mutant toxin moiety. The targeting moiety of the immunotoxin can comprise the human μCH2, μCH3 and μCH4 regions and VL and VH regions from murine Ig antibodies. These regions can be from the antibody UCHT1 so that the antibody moiety is scUCHT1, which is a single chain CD3 antibody having human μCH2, μCH3 and μCH4 regions and mouse variable regions as shown in the figures. Numerous DT mutant toxin moieties are contemplated, including for example, DT390 and DT389, with a variety of mutations or as the wild type toxin moiety.

The toxin moiety retains its toxic function, and membrane translocation function to the cytosol in full amounts. The loss in binding function located in the receptor binding domain of the protein diminishes systemic toxicity by reducing binding to non-target cells. Thus, the immunotoxin can be safely administered. The routing function normally supplied by the toxin binding function is supplied by the targeting antibody anti-CD3. The essential routing pathway is (1) localization to coated pits for endocytosis, (2) escape from lysosomal routing, and (3) return to the plasma membrane.

Any antibody that can route in this manner will be effective with the toxin moiety, irrespective of the epitope to which the antibody is directed, provided that the toxin achieves adequate proteolytic processing along this route. Adequate processing can be determined by the level of cell killing.

When antibodies dissociate from their receptors due to changes in receptor configuration induced in certain receptors as a consequence of endosomal acidification, they enter the lysosomal pathway. This can be prevented or minimized by directing the antibody towards an ecto-domain epitope on the same receptor which is closer to the plasma membranes (Ruud, et al. (1989) Scand. J. Immunol. 29:299; Herz et al. (1990) J. Biol. Chem. 265:21355).

The mutant DT toxin moiety can be a truncated mutant, such as DT390, DT389 or DT383, or other truncated mutants, with and without point mutations or substitutions, as well as a full length toxin with point mutations, such as DTM1, or CRM9 (cloned in *C. ulcerans*), scUCHT1 fusion proteins with DTM1 and DT483, DT390 and DT389, and have been cloned and expressed in *E. coli*. The antibody moiety can be scUCHT1 or other anti-CD3 or anti-T cell antibody having the routing and other characteristics described in detail herein. Thus, one example of an immunotoxin for use in the present methods comprises the fusion protein immunotoxin UCHT1 (or a fragment thereof)-DT390.

There is a consensus sequence for glycosylation (NXS/T (SEQ ID NO:19)) that may be removed or inserted to control glycosylation. Glycosylation occurs in all eukaryotes, e.g. *Pichia pastoris*.

There are numerous variants of the immunotoxins. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following are referred to as conservative substitutions.

Amino Acid Abbreviations

| Amino Acid | Abbreviations |
|---|---|
| Alanine | Ala, A |
| Allosoleucine | AIle |
| Arginine | Arg, R |
| Asparagine | Asn, N |
| aspartic acid | Asp, D |
| Cysteine | Cys, C |
| glutamic acid | Glu, E |
| Glutamine | Gln, K |
| Glycine | Gly, G |
| Histidine | His, H |
| Isolelucine | Ile, I |
| Leucine | Leu, L |
| Lysine | Lys, K |
| Phenylalanine | Phe, F |
| Proline | Pro, P |
| Pyroglutamic acid | PGlu |
| Serine | Ser, S |
| Threonine | Thr, T |
| Tyrosine | Tyr, Y |
| Tryptophan | Trp, W |
| Valine | Val, V |

Amino Acid Substitutions
Original Residue Exemplary Conservative Substitutions, others are known in the art.

| | |
|---|---|
| Ala | ser |
| Arg | lys, gln |
| Asn | gln, his |
| Asp | glu |
| Cys | ser |
| Gln | asn, lys |
| Glu | asp |
| Gly | pro |
| His | asn, gln |
| Ile | leu, val |
| Leu | ile, val |
| Lys | arg, gln; |
| Met | leu, ile |
| Phe | met, leu, tyr |
| Ser | thr |
| Thr | ser |
| Trp | tyr |
| Tyr | trp, phe |
| Val | ile, leu |

Substantial changes in function or immunological identity are made by selecting substitutions that are less conservative than those in the amino acid substitution table, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions that in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or praline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

It is also preferred that the transcribed units contain other standard sequences alone or in combination with the above sequences improve expression from, or stability of, the construct.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Transformation with a Mutagenizing Oligonucleotide

The oligomer of 56 nucleotides (see List of Primers) contains two point mutations to change amino acid 701 from glycine to arginine. A mutagenizing oligo (56 mer, 100 ug) was co-transformed into the GS200 (Mut+, His−, Arg−) strain with an ARG4 DNA fragment. The ARG4 gene with promoter was taken from plasmid PMY30 (supplied by Prof. Jim Cregg, Keck Graduate Institute of Applied Life Sciences, Claremont, Calif. 91711) by Sph I and EcoR V. Approximately 1000 transformants were obtained. To screen for mutated clones having the correct mutations, diagnostic PCR with primers mdb1EF-2 and 2253EF-2C was employed. The mutation-detecting primer (mdb1EF-2) can distinguish a difference in DNA sequence between the normal gene and the mutated gene at amino acid 701. For the normal gene, a PCR product could not be produced because 2 nucleotides at the 3' end were not matched with the DNA sequence of the normal gene, preventing extension by the Taq polymerase. For the mutated gene, the primer could anneal perfectly, so Taq polymerase could produce a PCR product. More than 1000 colonies were screened by this PCR method but no mutated colony was identified. (In the above PCR assay, amino acid 701 mutated EF-2 from *S. cerevisiae* served as a positive control. This mutated gene had been made previously with the intent of introducing it into *Pichia pastoris*. However, *Pichia pastoris* thus transformed had a very slow growth rate and produced the protein of interest at low levels.)

Transformation was performed with a partial DNA fragment containing the conserved region of the EF-2 gene and a mutation on amino acid 701. The partial sequence of *Pichia pastoris* EF-2 (positions 1717 to 2289, FIG. 3 (*a*) (*b*) (*c*) (*d*)) was mutated in vitro to change the amino acid 701 from glycine to arginme (FIG. 1) and then co-transformed into the GS200 strain with the ARG4 gene fragment. More than 2000 Arg4 positive transformants were obtained and screened them for the EF-2 mutation by diagnostic PCR with primers mdb2EF-2 and 2253EF-2C. The mutation was not observed.

List of Primers

Primers derived from *S. cerevisiae* EF-2:

```
5' primer:
                                     (SEQ ID NO: 20)
TTG GTT ATT GAC CAA ACT AAG GCT GTCCAA 3' primer:
                                     (SEQ ID NO: 21)
ACC TCT CTT CTT GTT TAA GAC GGA GTA GAT
```

Primers used in cloning and mutation of *Pichia pastoris* EF-2

$dT_{22}$-Not:

```
                                     (SEQ ID NO: 22)
5'-CTT GCT TTT GCG GCC GCT TTT TTT TTT
TTT TTT TTT TTT
```

EF-$2C_2$:

```
                                     (SEQ ID NO: 23)
5'-G ATA AGA ATG CGG CCG CCA TTT CTT
GGT CTT TGG GTT GAA G
```

EF-$2C_1$:

```
                                     (SEQ ID NO: 24)
5'-GAT AAG AAT GCG GCC GCC AAC TTA GTT
GTT GAC CAG TCT AAG
```

-continued

5'EF-2:
(SEQ ID NO: 25)
5'-ATA GCT AGC ACT TTG AAG TTC TTA ATT TTG TTC CTC

3'EF-2C:
(SEQ ID NO: 26)
5'-ATA AGA ATG CGG CCG CAA GTT AAT GAA ACA TTA AGC TTA CAA C wEF-2:
(SEQ ID NO: 27)
5'-G AAT GAC TTG TCC TCC ACC mEF-2:
(SEQ ID NO: 28)
5'- G AAT GAC TTG TCC TCC GCG G

EF-1426:
(SEQ ID NO: 29)
5'-CAA CTA GCT AGC GCT CAC AAC ATG AAG GTC ATG AAA TTC

BF-1318:
(SEQ ID NO: 30)
5'-AGA ACC GTC GAG CCT ATT GAC GAT

Mutagenizing oligo:

(SEQ ID NO: 31)
5'-CC CTG CAC GCC GAT GCT ATC CAC AGA AGA GGA GGA CAA GTC ATT CCA ACC ATG AAG mdb1EF-2:
(SEQ ID NO: 32)
5'-GCC GAT GCT ATC CAC AGA AGA mbb2EF-2:
(SEQ ID NO: 33)
GCC GAT GCT ATC CAC CGC CGC

2253EF-2C:
(SEQ ID NO: 34)
TCT CTT CTT GTT CAA AAC AGA GTA GAT ACC

Example 2

Spheroplast Transformation with the Partial Fragment of Mutated EF2 and ARG4 Fragment In the methods of Example 1, there was no selection step against wild type DT. A double transformation was thus employed. First, the mutated EF-2 fragment was transformed into the GS200 strain by electroporation. Then, electroporated cells were cultivated overnight to allow the expression of mutated EF-2 inside cell. Cultivated cells were used for making spheroplasts. The resulting spheroplasts were treated with wild type DT (200 μg/ml) and ARG4 fragment (10 μg) for 1 hour and transformed by $CaCl_2$ and PEG. Only a few transformants of normal colony size were obtained and there was no mutated strain. In addition, there were 100 or more micro-colonies obtained. 100 of these were screened but the mutated strain was not detected.

Example 3

Cloning and Sequencing of EF-2 Gene from *Pichia pastoris*

Prior to the cloning of the full sequence of the *Pichia pastoris* EF-2 gene, a partial sequence had been obtained. Initially, the conserved R domain of *Pichia pastoris* EF-2 was amplified from the genomic DNA using two primers derived from the same region of *S. cerevisiae* EF-2 (Perentesis et al., 1992). The 5' primer contained the sequence from position 1933 to 1962 of *S. cerevisiae* EF-2, whereas the 3' primer was complementary to the region of 2227 to 2256. The sequence of 324 nucleotides was then extended towards the 5' end to position 284 and the 3' end to position 2289 in the coding region of *Pichia pastoris* EF-2 gene. The extended sequence was later found to contain several mistakes. To clone the entire *Pichia pastoris* EF-2 gene, two species of cDNA were first synthesized separately from EF-2 mRNA with two different primers. Primer dT22-Not contains a run of 22 T residues complementary to the 3' polyA tail of the mRNA and the recognition sequence for restriction enzyme Not 1. Primer EF-2C2 has 25 nucleotides complementary to nucleotide positions 747 to 771 (FIG. 3 (a) (b) (c) (d)) of the *Pichia pastoris* EF-2 coding sequence. After cDNA synthesis, a homopolymeric track of A residues was added to the 3' end of the cDNA extended from primer C2 by homopolymeric tailing (Sambrook et al., 1989). The 5' end sequence of EF-2 was amplified by PCR from the modified cDNA with EF-2C2 and dT22-Not primers, whereas the 3' end sequence was from the cDNA synthesized from primers dT22-Not and EF-2C1, which contains 27 nucleotides corresponding to the positions 1927 to 1953. The PCR products representing the 5' end and 3' end sequences of *Pichia pastoris* EF-2 were then separately cloned to pCR2.1-TOPO vector (Invitrogen).

Five independent clones containing 5' sequence of EF-2 *Pichia pastoris* were selected for sequencing. They were first sequenced with M13 reverse and M13 forward primers located in the vector close to the up and down streams of the insert respectively, and then with an internal prime complementary to the positions 349 to 384 of EF-2 coding sequence. Among the 5 clones, three had identical sequences, one had two different nucleotides at two different internal locations, and the other one had another different internal nucleotides at a different location. These different nucleotides were likely produced by the cloning procedures since none of these different nucleotides were present in the clone derived from genomic DNA. At the 5' end, all five clones also had 57 to 69 nucleotides of the same sequence before the first ATG codon. The largest open reading frame (ORF) of the 5' end sequence starting from the first AUG is 747 nucleotides and the deduced amino acid sequence (249 aa) shares 90% identity with the first 249 aa at the N-terminus of *S. cerevisiae* EF-2. All four clones containing the 3' end sequence of the EF-2 sequence had the same sequence of 675 nucleotides followed by a homopolymeric A track. The largest ORF is 603 nucleotides ended at stop codon TAA, which is 72 nucleotides up stream of the poly-A track. The deduced amino acid sequence (201 aa) shares 85% identity with the last 201 aa at the C-terminus of *S. cerevisiae* EF-2. Having obtained both the 5' and 3' end sequences of *Pichia pastoris* EF-2, two primers were designed to amplify the entire the EF-2 gene from the genomic DNA of *Pichia pastoris*. Primer 5'EF-2 is derived from the 5' non-coding region and contains the sequence from positions 28 to 54 relative to the ATG initiation codon. Primer 3'EF-2C contains 27 nucleotides complementary to positions 2523 to 2549 at the 3' end. After PCR amplification with Pfu polymerase (Stratagene), the PCR products of EF-2 gene were treated with Taq polymerase to have the 3'A-overhangings added (Instruction manual for original TA cloning kit, Invitogen) and then inserted into the TA cloning vector pCR2.1-TOPO. Ten clones were picked, and the restriction enzyme analysis of plasmid DNA isolated from these clones indicated that they all had the same insert. DNA sequencing was performed first with M13 reverse and M13 forward primers and then advanced step by step towards the opposite ends with primers derived from the sequences obtained from the previous steps. Eight clones were completely sequenced, and found to be identical. The 3' end sequence obtained from the genomic DNA is identical to that from the mRNA. However, compared to the 5' sequence of mRNA, the sequence from the genomic DNA has an insertion of 77 nucleotides in the codon immediately next to the initiation site of the EF-2 ORF (FIG. 2). The insertion has the sequence GTATGT . . . CACTAAC . . . TAG (SEQ ID NO:35), a conserved pattern of short introns in *S. cerevisiae* (Davis et al., 200; Rymond & Rosbash, 1992). Although introns are common in *S. cerevisiae*, they are rarely present in *Pichia pastoris* (Gregg, personal communication). The coding sequence of *Pichia pastoris* EF-2 is present in FIG. 3 (*a*) (*b*) (*c*) (*d*). It contains 2526 nucleotides and code for 842 amino acids. The *Pichia pastoris* EF-2 is the same as the EF-2 of *S. cerevisiae* and *Schizosaccharomyces pombe* in length and shares 88% of identity in amino acid sequence with *S. cerevisiae* (Perentesis et al., 1992) and 78% with *S. pombe* (Mita et al., 1997). Both *S. cerevisiae* and *S. pombe* have two functional EF-2 genes (EFT1 and EFT2) per haploid genome. These two copies of the EF-2 genes encode the same amino acid sequence, but have a few different nucleotides (4 in *S. cerevisiae* and 13 in *S. pombe*) in their coding regions and dissimilar flanking sequences. However, the sequencing data of independent clones derived from mRNA and genomic DNA showed that all of the different clones had the same 5' and 3' end flanking sequences and an identical coding sequence. This plus the evidence of Southern blotting of restriction enzyme digested genomic DNA shows that *Pichia pastoris* has only one copy of the EF-2 gene.

Example 4

Construction of Mutating Plasmid
pBLURA-Δ5'mutEF-2

Figure 4:
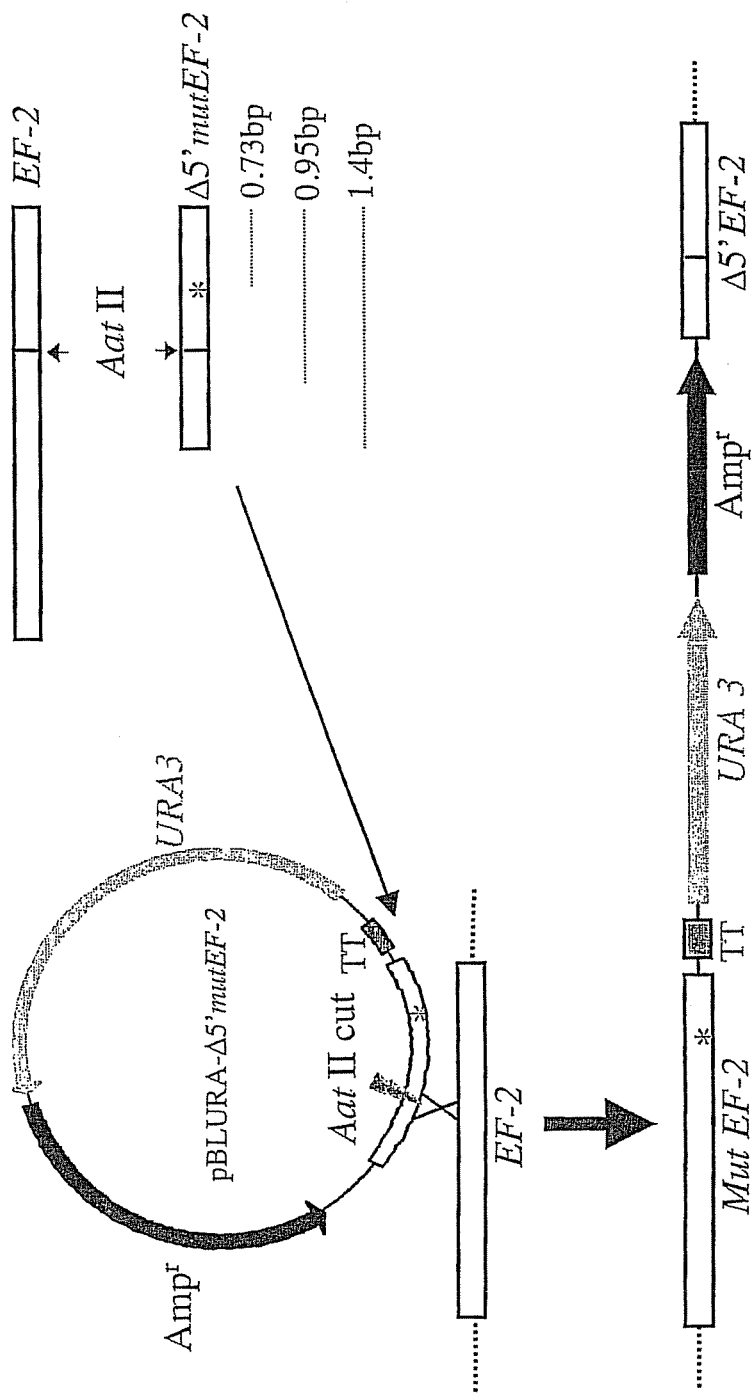
FIG. 4. Targeted mutation using the 3' sequence of EF-2 that has been mutated in vitro. The mutating plasmid pBLURA-Δ5' mutEF-2 contains four essential elements: β-lactamase gene(Ampr), Uracil selection marker (URA3), 3'AOX1 transcription termination sequence(TT) and the in vitro mutated FF-2 3' sequence, Δ5' mutEF-2.

To create DT resistant strains of *Pichia pastoris*, the EF-2 gene was mutated so that the Gly at position 711 was changed to an Arg. The strategy employed to introduce the mutation into the genome is based on that described by Shortle et al. (1984) and is shown in FIG. 4. In this method, a truncated form (at only one end) of the targeted gene was used to introduce a mutation to the gene in the genome by homologous recombination. Integration of the truncated gene fragment bearing a mutation will lead to a situation that the genome contains one intact copy of the gene with the mutation and one truncated copy. Because the targeted site is located close to the 3' end, the 5' truncated EF-2 (Δ5'EF-2) was used as the mutating sequence. Δ5'EF-2 contained 1127 nucleotides from the 3' end of EF-2 starting from position 1432 to 2549 (FIG. 3) and was generated by PCR with Pfu polymerase. After cloning into the pCR2.1-TOPO vector, Δ5'EF-2 was mutagenized in vitro by oligonucleotide-directed mutagenesis. The mutagenized Δ5'EF-2 (Δ5' mutEF-2) was then released from pCR2.1-TOPO by restriction enzymes Nhe1 and Not 1 that cut at the 5' and 3' ends respectively, and then cloned into the vector pBLURA-SX (provided by Professor Cregg and described in Geoffrey et al. (2001)) that had been digested by Nhe1 and Not 1. The vector contains the auxotrophic marker URA3. Plasmid DNA pBLURA-Δ5' mutEF-2 purified from bacterial was linearized before being electroporated into the strains of *Pichia pastoris*. The plasmid DNA contains a unique Aat II site located in the EF-2 sequence, about 220 nucleotides before the mutation site. Cleavage at this site will target the plasmid integration to the EF-2 locus and favors the event of the mutagenized sequence being transferred to the intact copy of EF-2. Three uracil auxotrophic strains of *Pichia pastoris* were transformed with the plasmid DNA. They are JC308 (ade1 arg4 his4 ura3), JC303 (arg4 his4 ura3) and JC307 (his4 ura3), and were all provided by Professor Cregg and described in Geoffrey et al. (2001). JC308 was transformed first followed by JO303 and JC307.

Example 5

Identification of Clones Containing Mutated EF-2

Figure 5:
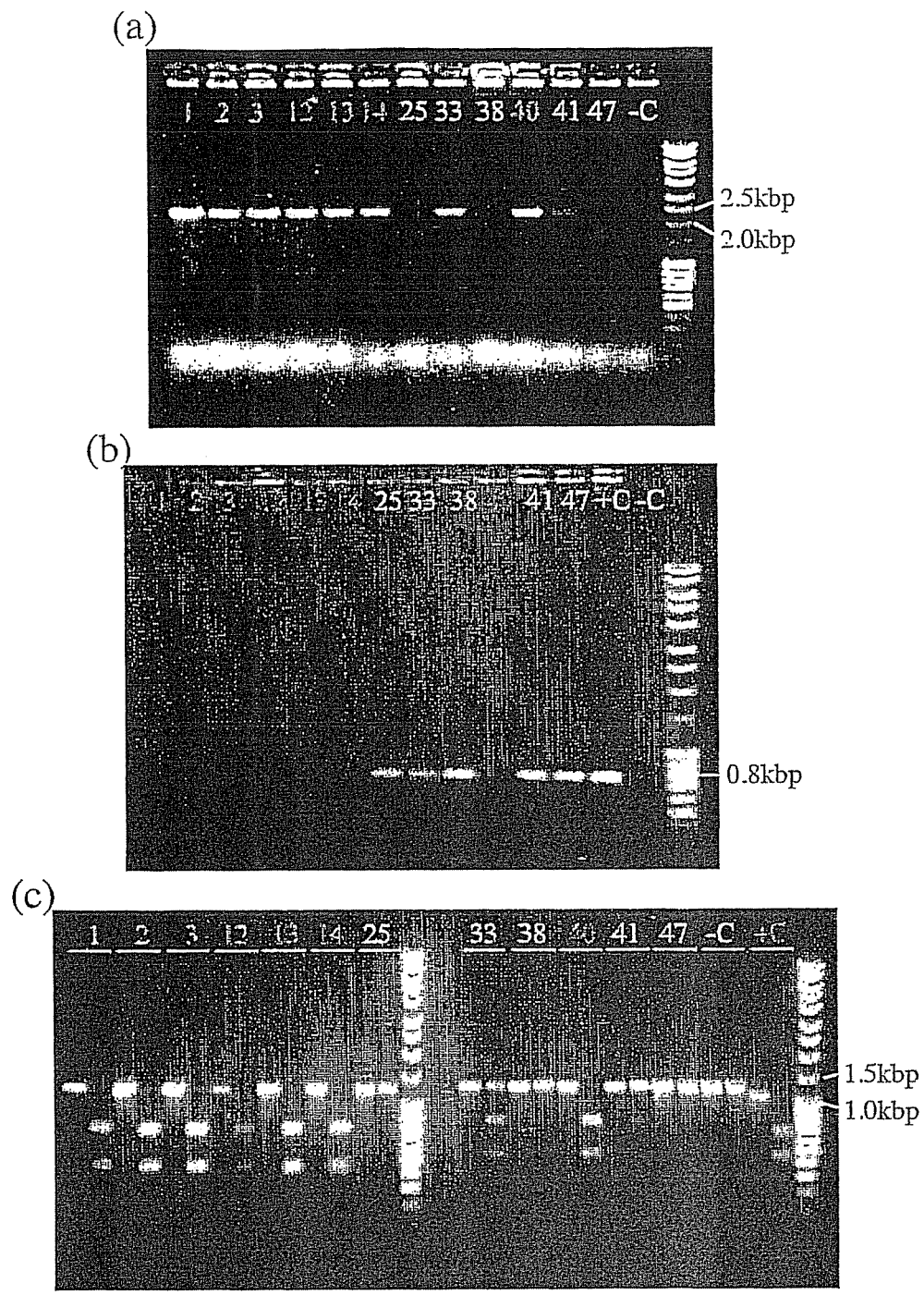
FIG. 5. Agarose gel electrophoresis of PCR products of selected Ura+ clone derived from *Pichia pastoris* JC308 strain. (a) PCR products with primers 1 and M; (b) PCR products with primers 2 and w; (c).Sca II digested PCR products with primers 2 and 3.

After electroporation with the linearized pBLURA-Δ5'mutEF-2 DNA, Cells were spread onto plates containing synthetic complete medium for yeast minus uracil (K.D Medical, Maryland). Ura+ clones were then analyzed by "Colony PCR" for the presence the correct mutations in the intact copy of EF-2. In this method, yeast cells from colonies were picked by tooth pickers and resuspended in 20 ul of PCR mix. DNA released from the cells lysed by the first PCR step (94° C. for 5 minutes) served as the template for PCR amplification. Five primers were used in the PCR detection procedures: primers 5'EF-2 and 3EF-2C were described previously in section 4; EF-2 (1318) has the EF-2 sequence from position 1318 to 1341; primer wEF-2 is complementary to the positions 2100 to 2119, whereas primer mEF-2 has the sequence complementary the same positions but specific to the mutations The designed nucleotide mutations shown in FIG. 1 created a new Sac II restriction enzyme site that was used to confirm the correct mutations in the genome Primers 5'EF-2 and mEF-2 were first used to detect the mutations in the Ura+ transformants. FIG. 5*a* shows that 9 (clones 1, 2, 3, 12, 13, 14, 33, 40 and 41) of the 12 selected Ura+ clones of JC308 are mEF-2 primer positive, they had a PCR product of the expected size (about 2.2 kbp), whereas clones 25, 38 and 47 were negative. As shown in FIG. 5*b*, when the same clones were analyzed for the presence of wild type sequence with primers EF-2 (1318) and wEF-2, all three mEF-2-clones were wEF-2 primer positive. A 0.8 kbp PCR fragment was produced. All mEF-2+clones were wEF-2-except for clones 33 and 41 that were also wEF-2+. Finally when primers EF2 (1318) and 3'EF-2C were used, all of the selected clones yielded a PCR product of about 1.2 kbp as expected (FIG. 5*c*). The PCR products from the clones that were mEF-2+ and wEF-2-were completely digested by Sac II, whereas those of the clones 25, 38 and 47 that were mEF-2− and wEF-2+ were not cut by the enzyme. In agreement with being both mEF-2+ and wEF-2+, clones 33 and 41 produced both Sac II clearable and non-clearable PCR produces. To investigate why clones 33 and 41 had both mutated and wild type EF-2, these clones were streaked on new selection plates and let the cells grow to form colonies. Ten well-isolated colonies were picked from each and performed the PCR with primer EF-2 (1318) plus primer 3'EF-2C and the Sac II digestion steps. None of the colonies had the same mixed PCR products as the originals. PCR products of 4 colonies from clone 33, 7 from 41 were completely digested by Sac II, whereas those of other colonies from clones 33 and 41 were not cut at all. This experiment shows that clones 33 and 44 were each originally formed by two different cells, one had an intact EF-2 with the mutations, and the other had an intact wild type EF-2. This experiment was then repeated and checked some of the clones that had only the Sac II clearable EF-2 (clones 1, 2, 3, 12, 13, 14, and 40) and confirmed that they only contained the mutated intact EP-2. After the success in obtaining EF-2 mutant clones of JC308, the same selection procedure was used to identify EF-2 mutant clones of JC303 and JC307. Among the Ura+ positive clones picked for analysis, 35% of them contained only the mutated intact EF-2. This high frequency of complete mutation may be due to the fact that Pichia pastoris only has one copy of EF-2 per haploid genome. As shown for CHO cells and S. cerevisiae, the Arg substitution for Gly711 of EF-2 in Pichia pastoris did not affect cell growth at normal conditions.

Example 6

Expression of DTA Chain in the EF-2 Mutants

Figure 7:
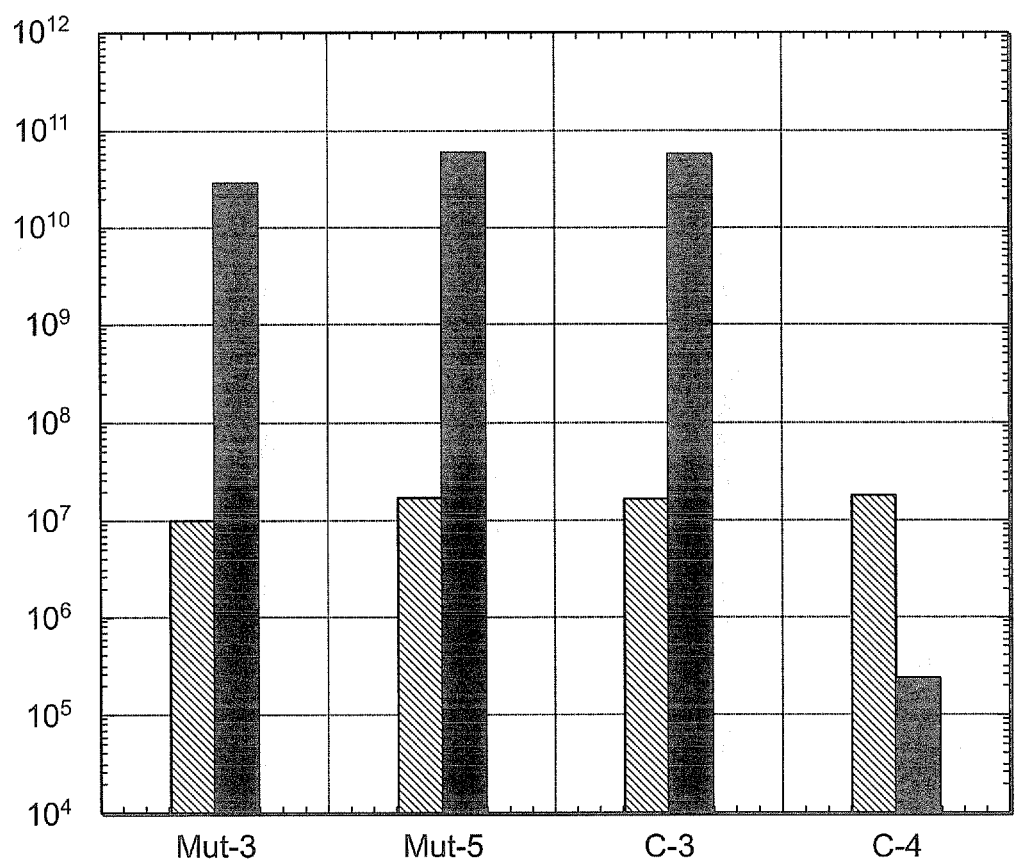
FIG. 7. The effect of intra-cellular expression of DT-A on the survival of *Pichia pastoris* strains with mutated or wild type EF-2. Mut-3 and Mut 5 are EF-2 mutants mutEF2JC307-8-DtA(3) and (5) respectively, Mut-3 expressed DT A chain in the cytosol, mut-5 did not. C3 and C4 are the wild type EF-2 strains that did (C4) or did not express DT A chain in the cytosol. The first bar in each category indicates the colony-forming units before methanol induction. The second bar in each category represents the colony-forming units after methanol induction.

To test whether the obtained EF-2 mutants are resistant to DT expression, mutEF2JC307-8, an EF-2 mutant clone (clone 8) of JC307, was transformed with the plasmid DNA of pPIC3-DtA. The construction of pPIC3-DtA was previously described (Woo et al., 2002). Briefly, the DT A chain gene with Bam HI at its 5' end and Not I at 3' was amplified by PCR, inserted into Pichia pastoris expression vector pPIC 3 (Invitrogen) and digested with these two enzymes. Integration of pPIC3-DtA allows cytosolic expression of DT chain upon methanol induction. This plasmid DNA had previously been used to transform the GS200 strain of Pichia pastoris (Invitrogen) and two of the resulting clones (C3 and C4) were used in the study on tolerance of Pichia pastoris to DT (Woo at al., 2002). C3 had been characterized as a non-DT A expressing clone, whereas C4 is a DT A expressing clone. After the transformation with pPIC3-DtA, six mutEF2JC307-8, (mutEF2JC307-8-DtA(1) to (6), clones were randomly picked for analysis of their cytosolic expression of DT A chain and their viability after methanol induction. Cells from single colonies of mutEF2JC307-8-DtA(1) to (6), C3 and C4 were grown in 2 ml YPD (Yeast extracts-Peptone-Dextrose) medium at 30° C. overnight before being pelleted down by centrifugation. Cells from each culture were resuspended in YP medium to a density at OD600 nm±0.5. Cell suspensions (2 ml) were induced by adding methanol to 1% and incubated at 30° C. with vigorous shaking. After methanol induction for 24 hours, cells from 100 µl of each culture were pelleted down and washed with PBS buffer. After this, cells were resuspended in PBS and mixed with protein sample buffer. Finally, the samples were subjected to two cycles of boiling and freezing on dry ice before being analyzed by SDS-PAGE and Western blotting with a DT specific antibody. The cultures of mutEF2JC307-8-DtA(3) and (5), C3 and C4 were also used for viability assay. This was performed by diluting each culture $10^4$ to $10^7$ fold with PBS buffer, plating 100 µl of aliquot on YPD plate and then counting the colonies appearing on the plates after 3 days incubation at 30'C. The result of SDS-PAGE and Western blotting showed that except for mutEF2JC307-8-DtA(5), all mutEF2JC307-8-DtA clones expressed DT A chain (FIG. 6a). The expression of mutEF2JC307-8-DtA(3) was estimated roughly at 20 µg/ml cell culture. As expected, C3 did not express DT A. Although C4 did express DT A, the protein band was barely visible (FIG. 6b). Before methanol induction, the number of the colony forming units (CFU) per ml of cells was about the same for mutEF2JC307-8-DtA(3) and (5), C3 and C4. After 24 hours methanol induction, the CFU number of mutEF2JC307-8-DtA(3) and (5) and C3 all increased about $10^3$ fold, whereas the CFU number of C4 decreased about $10^2$ (FIG. 7). This result demonstrated that the expression of DT A chain in the cytosol of cells bearing the mutated EF-2 was not toxic to the cells.

Example 7

Small-Scale Expression in Shake-Flask Culture

MutEF2JC307-8 was first used to express the bivalent immunotoxin Since this EF-2 mutant is auxotrophic for histidine, it was transformed with plasmid pPIC9K containing the final version of the modified gene for the bivalent immunotoxin: A-din DT390-bisFv described in Woo et al. (2002). Bivalent refers to two repeats of the sFv antibody fragment. The protocols used for transformation, selection for transformants, and protein expression and analysis were described previously (Woo et al., 2002, which is incorporated herein by reference in its entirety for the methods taught therein). After transformation, 12 colonies were randomly picked and analyzed for protein expression. SDS-PAGE analysis revealed that all of the selected clones expressed the bivalent immunotoxin, although some clones, such as clone number 2 [mutEF2JC307-8(2)], expressed at slightly higher levels than others. When they were cultured and expressed under the same conditions and at the same time, mutEF2JC307-8 (2) expressed the bivalent immunotoxin at the same level as pJHW#2, a clone of GS 115 (bearing the wild type EF-2) that had been transformed with pPIC9K-A-din DT390-bisFv. The expression levels of mutEF2JC307-8(2) and pJHW#2 were about 5 to 10 µg/ml of culture supernatant in shake-tube culture. The fact that mutEF2JC307-8(2) did not yield a higher level of expression demonstrated that other factors in addition to EF-2 ADP ribosylation also limit production of the bivalent immunotoxin.

In a second attempt to express the bivalent immunotoxin in mutated Pichia pastoris, two copies of A-dmDT390-bisFv gene were introduced into mutEF2JC303-5, an EF-2 mutant clone (clone 5) of JC303, which is auxotrophic for histidine and arginine. To build an expression vector with ARG4 selection marker, The AdmDT390-bisFv gene (see FIG. 20) was cloned into the expression vector pBLARGSX3 provided by Professor Cregg and described in Geoffrey et al. (2001). This was done by inserting the final version of A-dinDT390-bisFv gene plus the α-factor signal sequence released from pPICZα (Woo et al., 2002) by Hind III and Not I digestion into pBLARG-SX3 that had been cut with these two restriction enzymes. The resulting construct, pBLARG-A-dmDT390-bisFv (FIG. 8a), together with pPIC9K-AdmDT390-bisFv were electroporated at the same time into mutEF2JC303(5). Transformants expressing these two marker genes were selected on plates containing synthetic complete medium minus arginine and histidine (K.D Medical, Maryland). Eighteen colonies were picked from the selection plate and analyzed for their expression of the immunotoxin protein. SDS-PAGE showed that they all secreted roughly the same amount of intact immunotoxin protein into induction media. This amount was similar to that secreted from single copy clones: mutEF2JC307-8(2) and JHW#2. As shown in FIG. 9a, three of the selected clones (clones 3, 6, 8) also expressed a smaller, but much more abundant protein that reacted with an anti-DT antibody and had the same size as the monovalent immunotoxin (Liu et al., 2000). The smaller protein is more stable than the intact protein regardless as to whether this protein was produced from a truncated copy of A-dmDT390-bisFv gene or the proteolytically cleaved product of the intact protein. The figure also shows that there were many other smaller proteins in the culture supernatant that reacted with the anti-DT antibody; they were most likely the proteolytic cleaved products of the intact protein. The smallest and also the most abundant one was characterized as the A chain of DT, which is very stable (Collier 1975) and can account for the final product of proteolytic degradation of the intact protein. The degradation also took place inside the cell (FIG. 9b). Because the A chain is about ¼ of the size of the intact protein, the amount of the A chain shown on the Western blot indicates that the actual expression level was probably several times higher than the level of intact protein present in the induction medium. A majority of the protein synthesized was probably degraded either before or after secretion out into the medium. Although the double copy clones accumulated the same amount of intact protein in the medium as the single copy clones, the double copy clones produced a larger amount of degraded products, indicating that more gene products had been synthesized. Different measures to control the protein degradation have been employed but the production of the intact protein has not been increased. Thus protein degradation either within or outside the cell is a limiting factor to increase the production of the bivalent immunotoxin.

Example 8

Alternative Method for Large-Scale Expression in Fermentation Culture Using PMSF For large scale cultures, the BioFlo 4500 fermentor (New Brunswick Scientific Company), which was installed with a methanol sensor (Raven Biotechnology Company) for precise control of methanol concentration in cultures, was used. The initial fermentation medium (10 L) contained 1% yeast extract, 2% peptone or 2% soytone, 4% glycerol, 1% casamino acids, 1.34% yeast nitrogen base with ammonium sulfate and without amino acids, 0.43% PTM1 salt solution and 0.01% antifoam 289 (Sigma Co.) or a mixture of antifoam 204, 0.01% and Stuktol 0.01%. Depending on culture conditions, 75% (v/v) glycerol solution having 1.8% PTM1 salt solution was used for obtaining a desired cell density before methanol induction and/or supplementing an additional carbon source or energy source for methanol induction. 100% methanol solution for induction containing 20 mM PMSF and/or 1.2% PTM1 salt solution was used. Alternatively, induction was performed with a continuous feed of 4:1 methanol/glycerol containing 73 mM PMSF, and PMSF was added to 1 mM final concentration just prior to induction. In order to prepare a seed culture for the fermentor, 50 ml of YPD (1% yeast extract, 2% peptone and 2% glucose) was inoculated with 1 ml of a frozen stock of YYL #8-2 and then cultivated for 2 days at 30° C. with vigorous shaking. The 30 ml from the 50 ml culture was used as the first seed culture for inoculating approximately 600 ml of the second seed culture. The DO level in the fermentor was maintained at more than 25% for the whole fermentation run. The pH in the fermentor was kept at 3.5 for growth phase and 7.0 for methanol induction phase. The temperature was set at 28° C. for growth and 15-25° C. for methanol induction. Casamino acids solution (20%) was fed continuously at 20 ml/h during methanol induction or at the maximum speed of a pump for feeding for the first 2 hours of methanol induction. At the temperature of 23° C. for methanol induction, the expression level of the bivalent immunotoxin was the highest among 4 different runs. However, its expression level was similar to that of the current expression strain, pJHW #2. Table 1 summarizes results of 5 fermentation runs.

TABLE 1

Results of Fermentation Runs

| | Run 1 (#27) | Run 2 (#28) | Run 3 (#29) | Run 4 (#36) | Run 5 (#41) |
|---|---|---|---|---|---|
| glycerol-fed batch time (hour) | 5.5 | 4 | 0 | 7.5 | 6 |
| cell density at the start of methanol induction (%) | 19.44 | 18.60 | 11.93 | 20.02 | 21.16 |
| final conc. of PMSF (mM) | 2[1] | 2[1] | 2[1] | 7[2] | 2[1] |
| casamino acid (g) | 100[3] | 100[3] | 100[3] | 100[4] | 138[5] |
| temperature for methanol induction (C) | 25 | 20 | 15 | 23 | 23 |
| methanol consumption (g) | 3093 | 2776 | 2474 | 2538 | 3000 |
| glycerol feeding for methanol induction (g) | 475 | 0 | 0 | 0 | 0 |
| methanol induction time (hour) | 43 | 44 | 70 | 44 | 94 |
| final volume of the supernatant (L) | 13.3 | 12.3 | 11.9 | 11.4 | 13.4 |
| expression level (mg/L) at 22 hours of induction | 10 | 15 | 10 | 15 | NM[6] |
| expression level (mg/L) at 42 hours of induction | NM | NM | NM | NM | 27.5 |
| expression level (mg/L) at 66 hours of induction | NM | NM | NM | NM | 30.0 |
| Expression level (mg/L) at harvest | 3.3 | 18.3 | 26.6 | 27.5 | 32.5 |
| Total amount of the bivalent immunotoxin (mg) | 43.9 | 225.1 | 316.5 | 313.5 | 435.5 |

Figure 10:
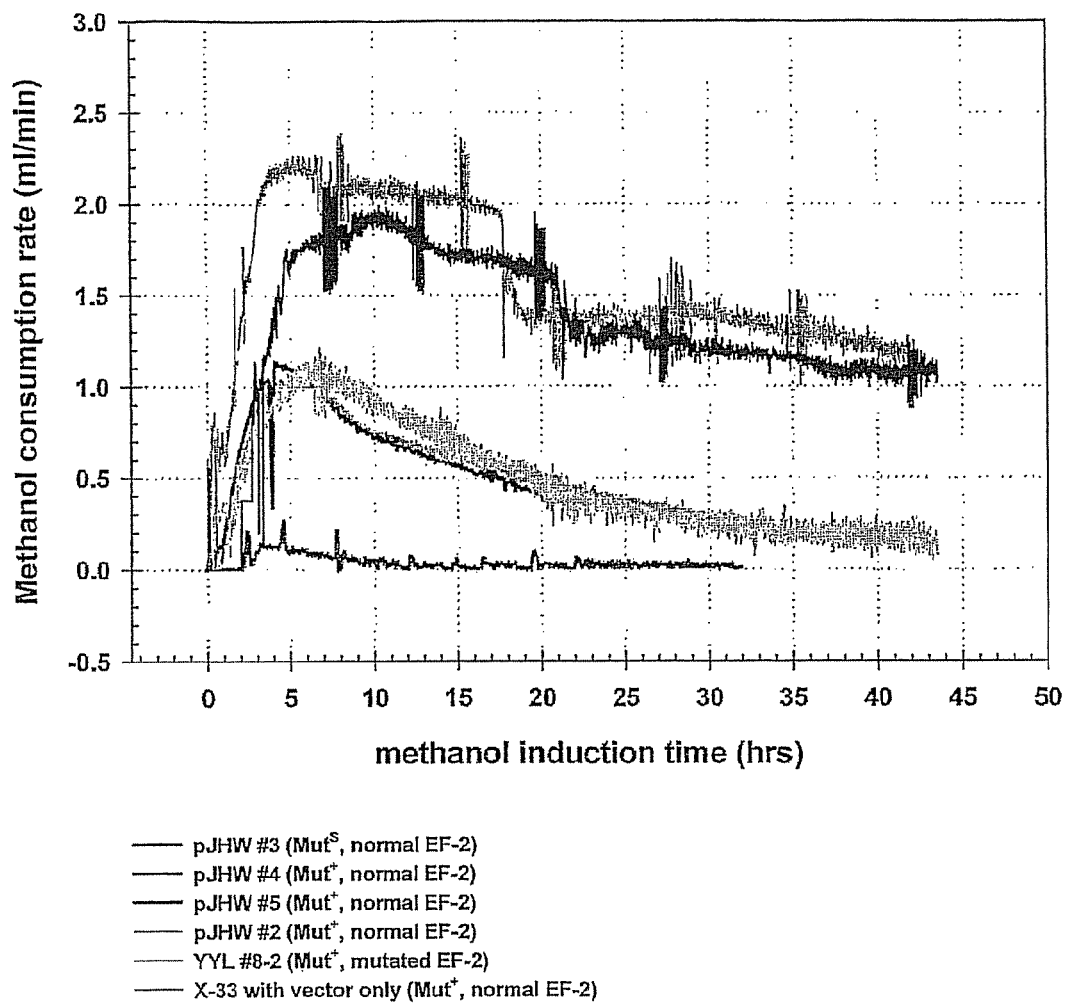
FIG. 10. Comparison of the methanol consumption rate among different *Pichia pastoris* strains. All of these strains are Mut+ (Methanol utilization plus) except for pJHW#3, which is MutS (Methanol utilization slow). pJHW#2 to 5 and the EF-2 mutant YYL#8-2 all expressed the bivalent immunotoxin A-dmDT390-bisFv. X-33 is a wild type strain that does not express A-dmDT390-bisFv, but was transformed with the expression vector.

[1] 50 ml of PMSF solution (3.484 g per 50 ml of methanol) was fed on the based of methanol concentration in the culture for the beginning of methanol induction. After the finish of feeding of PMSF solution, methanol solution containing 12 ml of PTM1 salt solution per 1 liter of methanol was replaced.
[2] 15 ml of PMSF solution (1.742 g per 15 ml of methanol) was injected at the beginning of methanol induction. On the basis of methanol concentration, methanol solution (20 mM PMSF and 12 ml of PTM1 salt solution/liter of methanol) was fed.
[3] 10% casamino acids solution was fed at the maximum speed of a pump at the start of methanol induction.
[4] 20% casamino acids solution was continuously fed at 20 ml/hour of pump speed.
[5] 15% casamino acids solution was continuously fed at 20 ml/hour of pump speed.
[6] not measured Under these conditions, maximum production of the wild-type expression strain, pJHW #2, is 27.5 mg/L with the total amount of 286.0 mg of the bivalent immunotoxin in 42 hrs of methanol induction. This level could not be increased beyond 42 hrs of induction. However, under conditions adopted from those for pJHW #2, production the EF-2 mutant strain YYL8-2 continued to increase up to 94 hrs after methanol induction in spite the fact that the initial 10 L of culture medium was gradually diluted to 13.4 L with methanol and 10% casamino acids solution (see run 5). The total amount of the bivalent immunotoxin of run 5 was 435.5 mg (32 mg/L). This is 1.46-fold greater that the maximum production of pJHW #2. The difference in the production of the bivalent immunotoxin between these two strains is reflected by the methanol consumption rates as shown in FIG. 10.

Example 9

Previous Method of Purification of the Bivalent Immunotoxin

The *Pichia pastoris* supernatant contains materials that compete with A-dmDT390-bisFv in binding to anion exchange resins. In addition, the toxin moiety can not be exposed to pH less than 6.5 without undergoing unfolding of hydrophobic residues. Therefore a hydrophobic interaction chromatographic step using Butyl-650M (TosoHaas) was employed. This resin preferentially binds monomeric A-dmDT390-bisFv over the dimeric form, a species having greatly diminished biologic activity. The capture step also concentrates a *Pichia pastoris* glycoprotein that appears as a diffuse band of ~40 kD on SDS gels but has the same mobility as A-dmDT390-bisFv under size exclusion chromatography. This material is eliminated by preferentially binding to Con A Sepharose (Pharmacia). A Superdex (Pharmacia) size exclusion step eliminates any A-dmDT390-bisFv dimer not previously screened during the capture step. The overall yield is 45% when the fermentation conditions achieve an A-din DT390-bisFv monomer content of 85%. The procedure for purification of A-dmDT390-bisFv is presented below:
1. Butyl-650M hydrophobic interaction chromatography
    Bed volume: 600 ml (in 10 cm diameter column)
    Flow Rate: 50-70 cm/hour
        sample preparation: solid sodium sulfate and 1 M Tris buffer (pH 8.0) were added to the final concentration of 0.5 M and 20 mM, respectively.
        sample volume: typically 10 L
        binding buffer: 500 mM Na2SO4, 1 mM EDTA, 20 mM Tris buffer (pH 8.0)
        elution buffer: 5% glycerol, 1 mM EDTA, 20 mM Tris buffer (pH 8.0)
        procedure:
            equilibrate the column with binding buffer
            applied the sample onto the column
            washed with 5 bed volume of binding buffer
            eluted A-dmDT390-BisFv with 6 bed volume of elution buffer
            regenerated the column by manufacturer's protocol
        volume of eluted fractions: 3600 ml
2. Diafiltration
    membrane: Amicon spiral-wound membrane (30 Kd) model S3Y30 (0.23 m2)
    sample: eluted fractions from capturing step
    diafiltration buffer: 5% glycerol, 1 mM EDTA, 20 mM Tris buffer (pH 8.0)
    buffer volume used for diafiltration: 6 volume of the sample
    pressure: 7 psi
    final volume: around 2 L
3. Poros 50 HQ ion exchange chromatography
    Bed volume: 40 ml (in 2.6 cm diameter column)
    Flow rate: 1 ml/min
    sample: diafiltrated sample (typically 2 L)
    binding buffer: 5% glycerol, 20 mM Tris buffer (pH 8.0)
    elution: 0~500 mM NaCl gradient (10 bed volume) in binding buffer
    procedure:
        equilibrate the column with binding buffer
        applied the sample onto the column
        washed with 3 bed volume of binding buffer and started to collect 20 ml of each fraction
        eluted A-dmDT390-BisFv with 10 bed volume of 0~500 mM NaCl gradient
        regenerated the column by manufacturer's protocol
    fraction size: 20 ml
4. Con A affinity chromatography
    a sample: 90~120 ml of the eluted fractions having A-dmDT390-BisFv from Poros TEX
    bed volume: 60 ml resin packed in 2.5 cm×20 cm column
    binding buffer: 5% glycerol, 20 mM Tris buffer (pH 8.0)
    flow rate: by gravity
    procedure
        equilibrated the column with binding buffer
        applied the sample to the column and started to collect 10 ml of each fraction
        added 0.5 M EDTA to each fraction at the final conc. of 1 mM
        washed the column with 5 bed volume of binding buffer
        regenerated the resin by manufacturer's protocol
5. Superdex 200 prep grade Gel filtration
    sample: 50 ml pooled fraction containing A-dmDT390-BisFv from Con A affinity step
    sample preparation: 5 M NaCl was added to the final conc. of 200 mM
    bed volume: 970 ml of Superdex 200 resin in 5 cm×60 cm column
    buffer: 200 mM NaCl, 1 mM EDTA, 20 mM Tris-Cl (pH 8.0) and 5% glycerol
    flow rate: 1 ml/min
    procedure
        equilibrated the column with binding buffer
        applied the sample to the column and started to collect 20 ml of each fraction
        eluted the column with 1 bed volume of the buffer
        regenerated the resin by manufacturer's protocol This method is difficult from a regulatory standpoint because Con A, which is toxic is leached from the column matrix. In contrast, the present method (see Example 16 and Example 38 uses borate to eliminate the glcoprotein. Borate binds to the glycoprotein vicyl hydoxyl groups and imparts a negative charge thus making the glycoprotein stick tighter to the anion exchange column. However the rIT as no carbohydrate groups and is eluted by the borate.

Example 10

Construction of Expression Vectors pPGAP-Arg and pPGAP-His

The promoter for *Pichia pastoris* glyceraldehydes-3-phosphate dehydrogenase gene ($P_{GAP}$) has been characterized and used for heterologous protein expression in *Pichia pastoris* (Waterham et al., 1997). $P_{GAP}$ is a strong and constitutive promoter. It was reported that protein expression under control of $P_{GAP}$ in glucose-grown *Pichia pastoris* was higher than that of the commonly used $P_{AOX1}$ in methanol-grown cells (Waterham et al., 1997; Döring et al., 1998). The disadvantage of constitutive promoters in heterologous protein expression is that they are not suitable for proteins that are toxic to the expressing host. Since the EF-2 mutants of *Pichia pastoris* were resistant to cytosolic expression of DT A, these mutants should allow constitutive expression of DT or PE based immunotoxins in their cells. Therefore $P_{GAP}$ was used to drive the expression of A-dmDT390-bisFv in *Pichia pastoris* in the hope that the $P_{GAP}$ would increase the expression level of protein.

Figure 8B:
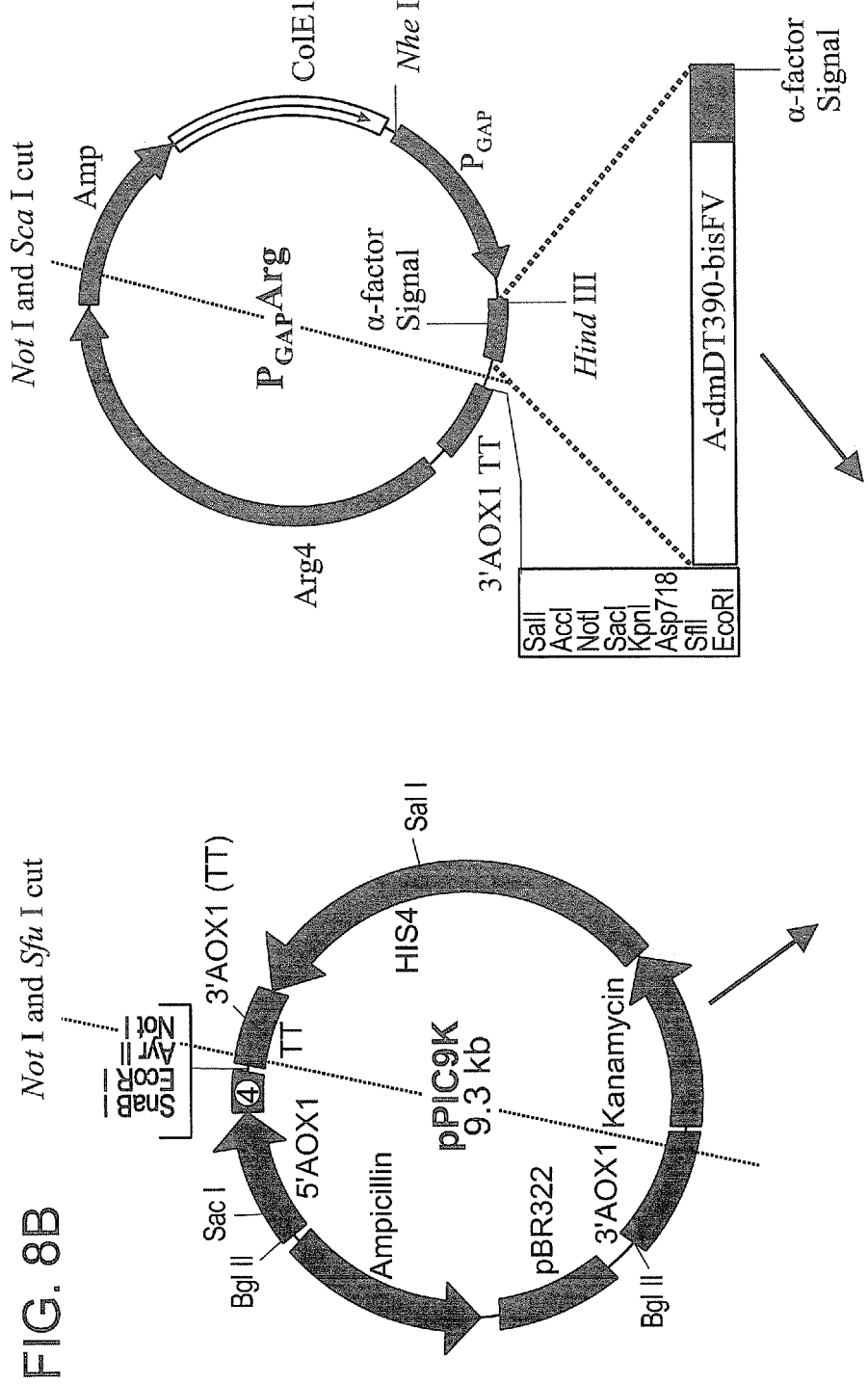
FIG. 8. Schematic presentation of plasmid construction. (a). pBLARG-A-dmDT390-bisFv; (b). pPGAPArg-A-dmDT390-bisFv; (c). pPGAPHis-A-dmDT390-bisFv.
Figure 8C:
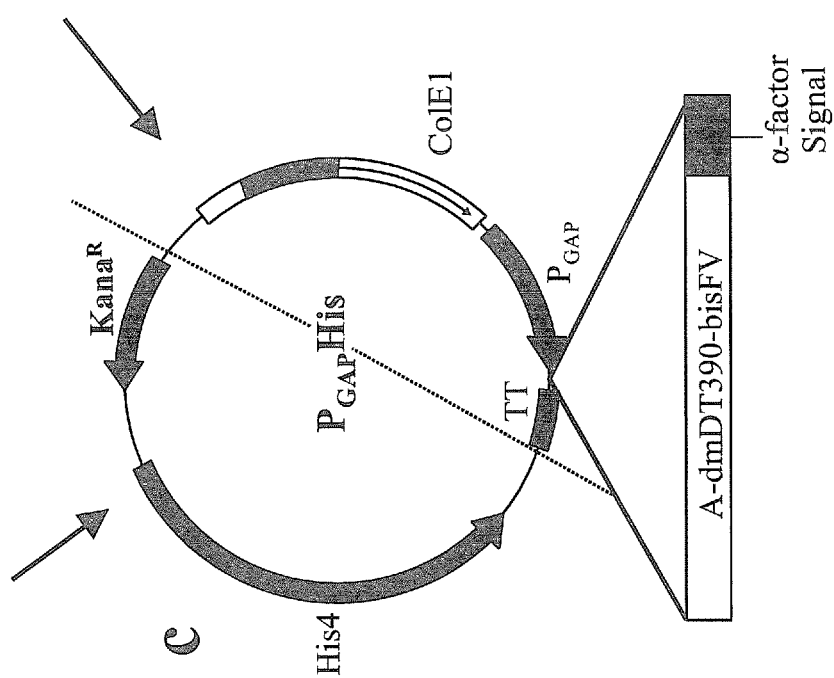

The construct pPGAPArg-A-dmDT390-bisFv was made by replacing the AOX1 promoter of pBLARG-A-dmDT390-bisFv with $P_{GAP}$ (FIG. 8b). First, $P_{GAP}$ was amplified from the expression vector pGAPZ A (Invitrogen) by PCR with primers containing sequences of $P_{GAP}$ 5' and 3' ends. The 5' and 3'end primers had a Nhe I and Hind III added respectively. After digestion with Nhe I and Hind III, the PCR products of $P_{GAP}$ were then inserted in pBLARG-A-dmDT390-bisFv that had been cut with these two restriction enzymes to remove the AOX1 promoter. The construct pPGAPHis-A-dmDT390-bisFv (FIG. 8c) was created by joining DNA fragments from plasmids pPIC9K (Invitrogen) and pPGAPArg-A-dmDT390-bisFv. The plasmid pPIC9K was first cut by Sfu I, after filling in with Klenow Fragment by Not I, then the DNA fragments were separated by agarose gel electrophoresis. The 5.1 kbp fragment containing kanamycin resistant gene, HIS4 gene and 3' AOX1 transcription termination (TT) was isolated and ligated with the plasmid DNA pPGAPArg-AdmDT390-bisFv that had been digested with Not 1 and Sca I to remove the 3'AOX1 TT and ARG4 gene.

Example 11

Expression of the Bivalent Immunotoxin Under the Control of $P_{GAP}$

As done for the expression under AOX1 promoter, one copy clones were obtained by transforming mutEF2JC307-8 with construct pPGAPHis-A-c-dmDT390-bisFv; two copy clones by transforming mutEF2JC303-5 with both pPGA-PArg-A-dmDT390-bisFv and pPGAPHis-A-dmDT390-bisFv. This time the two copy clones were constructed by two steps. First, mutEF2JC303-5 was transformed with pPGA-PArg-A-dmDT390-bisFv, after selection and protein expression analysis. The clone that produced the intact immunotoxin at highest level was then transformed with pPGAPHis-A-dmDT390-bisFv.

Small scale protein expression was carried out by inoculating a single colony to 2 ml YPD, and after overnight growth, cells were seeded in 2 ml expression medium at an $OD_{600\ nm}$=0.5, and then incubated at 28° C. for 24 hours before the culture supernatant was analyzed for expression of the immunotoxin. The expression medium is the similar to BMMYC used for expression of the immunotoxin under $P_{AOX1}$, but instead of 0.5% methanol it contains 2% glucose. SDS-PAGE analysis showed that accumulation of the intact protein in the culture supernatant of 2 copy clones was slightly higher than that of 1 copy clones. One of the 2 copy clones (Pgap2-9) has consistently producing 10 to 15 μg of intact protein per ml of culture medium. The results of Western blotting analysis of culture supernatant and extract cell pellet were consistent with those obtain from the expression under $P_{Aox1}$.

The production of the bivalent immunotoxin under control of $P_{GAP}$ was slightly higher than that under $P_{AOX1}$ in shake tube culture. Since fermentation allowed cells to grow to very high density, the increase in production under control of $P_{GAP}$ may be more significant when the production is in a bioreactor. The other advantage of $P_{GAP}$ controlled expression is that production procedure was simpler and shorter. It did not require addition and maintenance of methanol in the expression medium. The whole production procedure was about 40 hours compared to more than 72 hour for that of the $P_{AOX1}$ controlled expression.

Example 12

Yeast Strains and Strain Maintenance

In order to optimize fermentation conditions, genetically engineered *Pichia pastoris* strain JW102 (former name was pJHW #2) was used, which was generated for production of the bivalent immunotoxin from the host strain GS 115 (Invitrogen, Carlsbad, Calif.) (Woo et al., 2002). The AOX1 (alcohol oxidase 1) promoter controlled the expression of immunotoxin during methanol induction. The gene product was secreted by the alpha-prepro leader sequence. To compare the growth profile and fermentation parameters in the fermentor, X-33 and JW103 (MutS) or mutEF2JC307-8(2) were used (Table 2) and elsewhere.

TABLE 2

The *Pichia pastoris* strains used in this study.

| Names | Protein of interest | Phenotypes |
|---|---|---|
| JW102* | Secretion of bivalent immunotoxin | His$^+$Mut$^+$ |
| JW103* | Secretion of bivalent immunotoxin | His$^+$Mut$^S$ |
| C-4 | Cytosolic expression of A chain of DT | His$^+$Mut$^+$ |
| X-33 | Host strain | His$^+$Mut$^+$ |

*JW102 and JW103 were renamed from pJHW#2 and pJHW#3, respectively (Woo et al., 2002)

Strain JW102, expressing the bivalent immunotoxin, was genetically very stable. After subculturing the strain more than 60 times onto YPD plates (1% yeast extract, 2% Bacto peptone, 2% dextrose and 2% agar), the strain maintained expression of the bivalent immunotoxin. A colony isolated at the very early stage was expanded in YPD broth (1% yeast extract, 2% Bacto peptone, 2% dextrose) and then kept as frozen stock at −80° C. Frozen stock was prepared by mixing a 2-day incubation culture with an equal volume of 25% (v/v) glycerol and 1 ml of the mixture was dispensed into a 2 ml Cryo vial.

Example 13

Fermentation

A BioFlo 4500 fermentor (New Brunswick Scientific Company, Edison, N.J.), with a methanol sensor and controller (Raven Biotechnology Company, Canada) that maintained methanol at 0.15% (v/v) during induction was used. This fermentor was linked to a computer running an AFS-BioConimand Windows-based software (New Brunswick Scientific Company), which allowed for the control of all parameters by programmed processes. The basic initial fermentation medium (10 liters) contained 2% (20 g/L) yeast extract, 2% (20 g/L) Soytone Peptone (Difco), 4% (40 g/L) glycerol, 1.34% (13.4 g/L) yeast nitrogen base with ammonium sulfate and without amino acids, 0.43% (4.3 mL) PTM1 salt solution and 0.02% (v/v) antifoam 289 (Sigma Co.). The PTM1 salt solution (Invitrogen) contained of 24.0 mM (6 g/L) cupric sulfate ($CuSO_4.5H_2O$), 0.534 mM (80 mg/L) sodium iodide (NaI), 17.8 mM (338.6 mg/L) manganese sulfate ($MnSO_4.5H_2O$), 0.827 mM (200 mg/L) sodium molybdate ($NaMoO_4.2H_2O$), 0.323 mM (20 mg/L) boric acid ($H_3BO_3$), 2.1 mM (500 mg/L) cobalt chloride ($CoCl_2.6H_2O$), 147.0 mM (20 g/L) zinc chloride ($ZnCl_2$), 234.0 mM (65.1 g/L) ferrous sulfate ($FeSO_4.7H_2O$), 1.64 mM (400 mg/L) biotin, 188.0 mM (18.4 g/L) sulfuric acid ($H_2SO_4$).

The glycerol batch phase was completed within 18 h of inoculation, and complete consumption of glycerol in the culture was detected by monitoring the DO spike. A glycerol-fed batch phase ensued, during which 75% (v/v) glycerol was fed by ramping up the feeding rate at 0.1 g/min to 3.0 g/min for 7 h. Seventy-five percent (v/v) glycerol solution containing 18 ml/L (1.8%) of PTM1 salt solution was used for obtain the desired cell density for 7 h before methanol induction. Induction was performed with a continuous feed of methanol or 4:1 methanol:glycerol (based on volume) with or without 101 mM PMSF (phenylmethylsulfonyl fluoride). The feeding rate of methanol or 4:1 methanol:glycerol was automatically controlled to be maintained at the set point (0.15% (v/v) methanol in the culture) by the methanol sensor and controller. The methanol consumption rate was measured by weighing a methanol solution or methanol/glycerol mixed solution every one minute on a computer interfaced balance (PG5002S, Mettler Toledo, Switzerland). PMSF was added to 1 mM final concentration just prior to induction when PMSF was added during methanol induction. A casamino acids or yeast extract solution (10%, w/v) was fed continuously at 10 ml/h/10 L initial volume during methanol induction.

Alternatively, with the EF-2 mutant, the carbon source may be limited to methanol during induction and the methanol feed rate may be limited to about 0.5~0.75 ml/min or lower and regulated by a precision pump (Table 3). In run #53, methanol was fully fed by a pump that was controlled by a methanol sensor to maintain a set point of 0.15% methanol in the culture. In run #56, methanol feeding during methanol induction was limited to 0.75 ml/min. Concentration of bivalent immunotoxin in the supernatants taken at various induction time points was determined on Coomassie-stained SDS-polyacrylamide gels. For further comparison between both runs, protein yield of the Butyl 650M HIC capture step was deter fined from 1 liter of each supernatant. Limited feeding of methanol during methanol induction increased the secretion level of bivalent immunotoxin up to 50 mg/L.

TABLE 3

Limited feeding of methanol at a rate of 0.75 ml/min during methanol induction increased secretion level of bivalent immunotoxin in the EF-2 mutant strain.

| Induction time | Purification step | Run #53 Full feeding of methanol | Run #56 Limited feeding of methanol |
|---|---|---|---|
| 22 hr | Supernatant | 12.5 mg/L | 15.0 mg/L |
|  | Butyl 650M HIC (from 1 L supernatant) | 11.7 mg | 14.4 mg |
| 44 hr | Supernatant | 30.0 mg/L | 35.0 mg/L |
|  | Butyl 650M HIC (from 1 L supernatant) | 23.4 mg | 28.8 mg |
| 67 hr | Supernatant | 35.0 mg/L | 50.0 mg/L |
|  | Butyl 650M HIC (from 1 L supernatant) | 29.3 mg | 40.3 mg |

In order to prepare a seed culture for the fermentor, 50 ml of YSG broth (1% (w/v) yeast extract, 2% (w/v) Soytone Peptone, 1% (w/v) glycerol) was inoculated with 1 ml of a frozen stock (−80° C. in 25% (v/v) glycerol) and then cultivated for 2 days at 28° C. at 250 RPM (orbit diameter, 1.9 cm).). Thirty ml from a 50 ml culture was used as the first seed culture for inoculating 600 ml of YSG broth in two 1 L flasks. After cultivation for 1 day at 28° C. at 250 rpm (orbit diameter, 1.9 cm), the cultures were used as the second seed culture for inoculation of 10 L of initial complex fermentation medium in the fermentor. All parameters were automatically managed by running processes programmed in the AFS-Bio-Command software. The DO level in the fermentor was maintained at >40% for the entire fermentation with $O_2$ supplementation as needed. The pH in the fermentor was kept at 3.5 during the growth phase and at 7.0 during the methanol induction phase by adding 29% (v/v) $NH_4OH$ or 40% (v/v) $H_3PO_4$. The pH was ramped up from 3.5 to 7.0 for 2 h before the initiation of methanol induction. The pH shifting procedure reduced the secretion of contaminant proteins (75 kDa and 35 kDa bands) into the supernatant. The temperature was set at 28° C. for growth and 15-25° C. during methanol induction. The induction temperature was ramped down from 28 to 25-15° C. during the first 4 h of methanol induction. Reducing the bioreactor agitation may increase the fraction of monomeric and bioactive immunotoxin. A bioreactor agitation of 400 rpm increases the fraction of monomeric and bioactive immunotoxin by 50% over a bioreactor agitation of 800 rpm (FIG. 12). Providing a detergent or other denaturant during agitation may reduce aggregation of the immunotoxin. Including TWEEN 20® at 0.01% during agitation of immunotoxin further reduces aggregation and increases the fraction of monomer and bioactive immunotoxin to 90% (FIG. 13). After harvesting the culture, the supernatant was prepared by centrifugation (2,800×g at 4° C. for 30 min). EDTA was added to a final concentration of 5 mM to prevent protein degradation during storage at 4° C.

Example 14

Measurement of Wet Cell Density (%, w/v) for Monitoring Cell Growth

One ml of culture sample was placed in a tared 1.5-ml microcentrifuge tube and spun at 20,800×g at 25° C. for 2 min. The supernatant was removed with a pipet and residual liquid in the tube was blotted with filter paper. After weighing the tube containing the cell pellet, the wet cell density (%, w/v) was calculated.

Example 15

Purification

A scaleable 3-step procedure for purification of the bivalent immunotoxin has been developed that utilizes borate anion exchange chromatography to eliminate contaminating host glycoproteins. Purifications were performed with 1 L of centrifuged supernatant. No dialysis or diafiltration step was employed. In brief, 1 L of supernatant was mixed with 28.4 g of solid $Na_2SO_4$ and applied to a 100 ml bed of butyl-650M and eluted with 5% glycerol, 20 mM tris and 1 mM EDTA, pH 8.0, after washing in 200 mM $Na_2SO_4$. 600 ml of eluant was diluted with 4.2 L of TE buffer (20 mM tris, 1 mM EDTA, pH 8.0) and applied to a 40 ml bed of Poros 50 HQ. The bivalent immunotoxin was eluted in steps of sodium borate buffer from 25-100 mM, and then glycoproteins and some highly aggregated immunotoxin were eluted with 1 M NaCl. 1.2 L of the borate eluant was diluted with 3.6 L of TE buffer and applied to a 5 ml prepacked bed of Hi-trap Q. After washing, the bivalent immunotoxin was eluted with a 0-400 mM NaCl gradient.

Butyl-650M hydrophobic interaction chromatography (BIC): Approximately 100 ml of Butyl-650M resin (Tosoh Biosep LLC) was packed in a 5 cm×20 cm XK column (Amersham Pharmacia Biotech) and the column was equilibrated with Buffer A containing 200 mM Na2SO4, 1 mM EDTA, 20 mM Tris-Cl buffer (pH 8.0). Solid sodium sulfate and 1 M Tris-Cl buffer (pH 8.0) were added to 1 liter of the supernatant to a final concentration of 200 mM and 20 mM, respectively. The sample was filtered with a 802 fluted filter paper (>15 um particle retention: Whatman Inc.; Clifton, N.J., USA) before loading. The flow rate was 44 cm/hour (14.4 ml/min). After equilibrating the column, 1 L of the prepared sample was applied onto the column, and then the column was washed with 6 column volumes of binding buffer A. The bound proteins to Butyl-650M resin were eluted with 6 column volumes of Buffer B containing 5% glycerol, 1 mM EDTA, 20 mM Tris-Cl buffer (pH 8.0). The eluted fractions having the immunotoxin were pooled for the next step (volume: ~600 ml). After each run, the column was regenerated according to the manufacturer's protocol. All steps were performed in a cold room except for the first step that was carried out at room temperature.

Poros 50 HQ anion exchange chromatography (AEX) by step-elution with sodium borate buffer: Approximately 40 ml of Poros 50 HQ resin (PerSeptive Biosystems) was packed in a 2.6 cm×20 cm XK column (Amersham Pharmacia Biotech) and then the column was equilibrated with Buffer B. The pooled sample from the previous step was diluted with 4.2 L of TE buffer (20 mM Tris-Cl, 1 mM EDTA, pH 8.0). The diluted sample was loaded onto the column at a flow rate of 80.2 cm/hour (7.08 ml/min), and then the column was washed with 6 column volumes of Buffer B. The bound proteins were eluted in steps of sodium borate of 25 mM, 50 mM, 75 mM and 100 mM in Buffer B (10 column volumes for each step). These eluted fractions were pooled for the next step. The residual protein bound to the resin was stripped with 6 column volumes of 1 M NaCl in Buffer B. After each run, the column was washed with 0.5 M NaOH and then re-equilibrated with Buffer B minus 5% glycerol for the next use.

Hi-trap Q anion exchange chromatography: A prepacked Hi-trap Q anion exchange column (5 ml) was purchased from Amersham Pharmacia Biotech. The pooled sample from the previous step was diluted with 3.6 L of TE buffer. The sample was loaded onto the equilibrated column with Buffer B at a flow rate of 221.5 cm/hour (7.08 ml/min). The column was washed with 5 column volumes of Buffer B. The bound immunotoxin was eluted with a linear 0~400 mM NaCl gradient in Buffer B (20 column volume). The flow rate for washing and eluting steps was 2 ml/min and fraction size was 5 ml.

Example 16

Measurement of Protease Activity in the Supernatant

Unnicked CRM9 (one point mutation in the recognition domain of diphtheria toxin (7)) was used as the substrate for measurement of serine-protease activity in the supernatant at a final concentration of 225 μg/ml. The supernatant was incubated at 28° C. with shaking at 250 rpm (orbit diameter, 1.9 cm) for 20 h before applying to a 4-20% tris-glycine precast SDS-PAGE gel in the presence of reducing agent (100 mM dithiothreitol). CRM9 contains a well exposed furin/Kex-2 cleavage site between the A fragment (22 kDa) and B fragment (40 kDa) spanned by a disulfide bond. Protease activity in the medium was detected by loss of unnicked CRM9 under reducing condition, and the band intensity of the unnicked CRM9 was quantified by densitometry on Coomassie stained gels.

Example 17

SDS-PAGE and Western Blotting

Proteins in culture supernatants were subjected to SDS-PAGE utilizing tris-glycine 4~20% precast gels (Invitrogen) under non-reducing and/or reducing conditions. For Western blotting, the fractionated proteins were transferred onto nitrocellulose membranes by electroblotting. Non-specific binding was blocked with 5% nonfat skimmed milk in TBST buffer (50 mM Tris-HCl, pH 7.5, 150 mM NaCl, and 0.1% TWEEN 20®). Goat polyclonal antibody directed against diphtheria toxin (Thompson et al., 1995) diluted 1:2000 was used as the primary antibody, and alkaline phosphatase-conjugated rabbit anti-goat IgG (Roche Molecular Biochemicals) diluted 1:5000 was used as the secondary antibody. The immunotoxin was visualized with one-step NBT/BCIP substrate (Pierce Chemical Company). Alternatively, rabbit polyclonal antibody directed against $(G_4S)_3$ linker was used as the primary antibody for detecting intact immunotoxin and degraded products since the bivalent immunotoxin contained three $(G_4S)_3$ linkers. This antibody was raised against the synthetic peptide, whose amino acid sequence was GGGGSGGGGSGGGGS (SEQ ID NO: 17).

Example 18

Cytotoxicity Assay

The tests to measure the specific cytotoxicity of anti-human anti-CD3 immunotoxins expressed in *Pichia pastoris* were performed as described (Neville et al., 1992). Briefly, immunotoxins were applied to Jurkat cells, a human CD3ε+ T cell leukemia line, (5×104 cells/well) in 96-well plates in leucine-free RPMI 1640 medium. After 20 hours, a 1 hour pulse of [$^3$H] leucine was given. The cells were then collected onto filters with a cell harvester. After addition of scintillant, samples were counted in a Beckman scintillation counter using standard liquid scintillation counting techniques.

Example 19

Measurement of Cell Viability

In order to measure cell viability of cultures taken at various time points in fermentation, Ormerod's method was modified (Ormerod, 2000). Fluorescein diacetate (FDA) and propidium iodide (PI) were used as vital dyes of cell viability. FDA taken up by *Pichia pastoris* was converted to fluorescein by an intracellular esterase. If a cell has an intact plasma membrane, fluorescein is retained and PI is excluded. In brief 500 μl of a suspension of *Pichia pastoris* cells at 106 cells/ml in the PBS buffer were mixed with 50 μl of FDA solution (10 μg/ml) and 50 μl of PI solution (100 μg/ml). After incubation at room temperature for 10 min, cell viability of the sample was analyzed by flow cytometry. The viable cell gate included green fluorescence and excluded red fluorescence.

Example 20

Quantification of Concentration of the Bivalent Immunotoxin

A Superdex 200 10/300 GL prepacked column (dimension 1.0 cm×30 cm) was purchased from Amersham Pharmacia Biotech. The column was connected to an HPLC system (GBC Scientific Equipment; Arlington Heights, Ill., USA). Gel filtration buffer consisted of 90 mM sodium sulfate ($Na_2SO_4$), 10 mM sodium phosphate monobasic ($NaH_{27}PO_4.H_2O$) and 1 mM EDTA (pH 8.0). The flow rate was 0.5 ml/min and injection volume was 500 μl. Purified immunotoxin of known concentration based on UV absorbance (25) served as a standard.

Quantification of the bivalent immunotoxin in supernatants or liquid samples, was performed by comparing the intensity of Coomassie-stained 4-20% precast SDS gels with that of immunotoxin standards of known concentration.

Example 21

Immunotoxin Toxicity During Expression in *Pichia pastoris* is Manifest by a Reduction in AOX1 Activity The bivalent immunotoxin in *Pichia pastoris* was expressed via the secretory route. This secretion of the bivalent immunotoxin in *Pichia pastoris* significantly attenuated the toxicity of the immunotoxin (Woo et al., 2002), but the bivalent immunotoxin expression depressed metabolic capacity of methanol utilization and growth reduction during methanol induction in fermentor culture.

Figure 11:
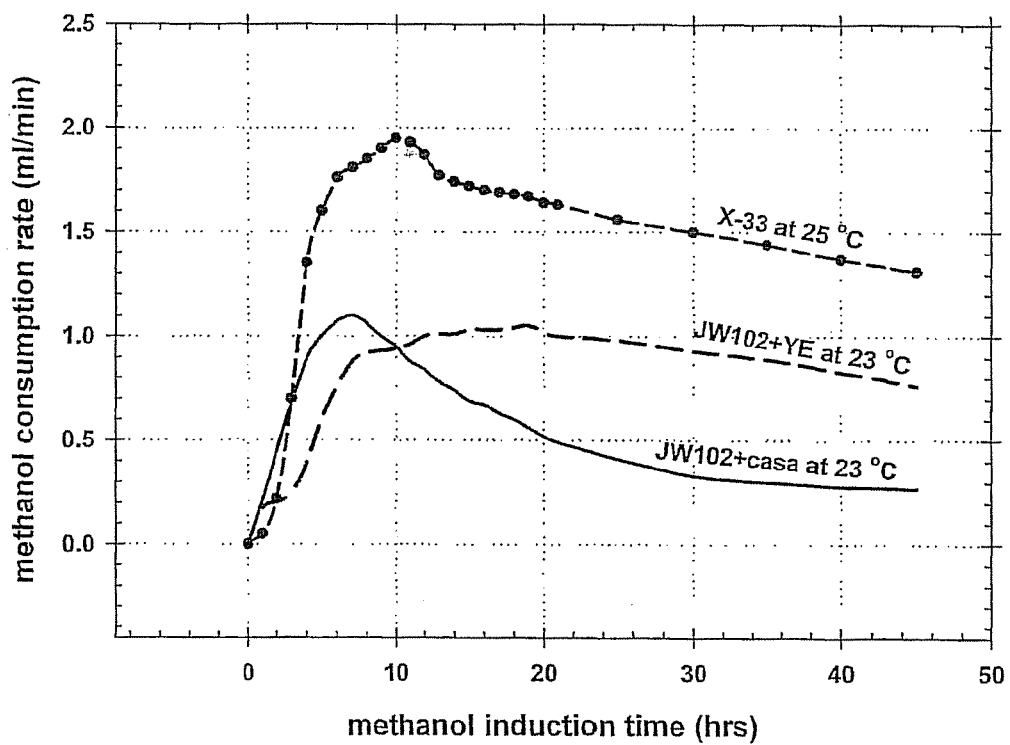
FIG. 11. Comparison of profiles of methanol consumption rate between X-33 and JW102 and between different nutrient feeding of JW102 at the indicated temperature. YE and casa represents feeding of yeast extract and casamino acids, respectively.

In the metabolism of methanol by *Pichia pastoris*, oxidation of methanol by alcohol oxidase (AOX1) is the rate-limiting reaction (Veenhuis et al., 1983), and the amount of the AOX1 gene product determines how rapidly methanol is metabolized. AOX1 can account for 30% of the proteins in *Pichia pastoris* cells utilizing methanol. Therefore, measurement of methanol consumption rates during methanol induction reflects the AOX1 level and provides an indication of how the expression of the bivalent immunotoxin affects protein synthesis and degradation of AOX1 in *Pichia pastoris*. To this end, profiles of the methanol consumption rate in a fermentor culture were compared between the wild type host strain X-33 and the JW102 strain, which expressed the bivalent immunotoxin via the secretory route. Under the fermentation conditions where casamino acid supplements were used during methanol induction, X-33 had a maximum 1.95 ml/min of methanol consumption at 25° C. and the consumption rate was maintained at more than 70% of the maximum rate during the whole methanol induction phase (FIG. 11). For the immunotoxin expressing strain JW102 (Mut+), the maximum methanol consumption rate was approximately 1.10 ml/min at 23° C. After the peak point at 7~8 hours following the initiation of methanol induction, the consumption rate was gradually decreased to 20% of the maximum rate. Within the first 18 hours of methanol induction, the methanol consumption rate dropped below 50% of maximum methanol consumption rate (FIG. 11). These low levels of methanol consumption were associated with low levels of wet cell density increase, 2% for JW102 versus 10.5% for X-33 at 44 hours (FIG. 14).

Example 22

Use of PMSF and Casamino Acids or Yeast Extract During the Methanol Induction Phase In the initial stages of fermentation optimization, supplementing of PMSF and casamino acids during methanol induction was crucial for boosting the expression level in the fermentor. Without these two components during methanol induction, the expression level of the bivalent immunotoxin reached a maximum 7 hours after initiation of methanol induction and then decreased. However, supplementing these two components during methanol induction extended the optimal induction time from 7~8 hours to 24~48 hours after the start of methanol induction. In addition, the expression level was improved up to 2-fold.

To avoid the use of animal-derived material, yeast extract was substituted for casamino acids. This change resulted in a substantial increase in the expression level by 30% and in wet cell density by 45%. Gain of wet cell density for JW102 by continuous feeding of yeast extract was close to that for X-33 during methanol induction (FIG. 14). These improvements were due to constancy of the methanol consumption rate at greater than 80% of the maximum rate (FIG. 11).

An example of the final expression method, disclosed herein (see Example_41), uses the toxin resistant EF-2 mutant, limited methanol feeding during induction of 0.5 to 0.75 ml/min (per 10 L initial medium) without an additional carbon source, extension of induction time to 163 h, a temperature of 15° C., a continuous infusion of yeast extract, limitation of agitation speed to 400 RPM, addition of anti-foam agent up to 0.07%, and supplementation of oxygen when DO levels fall below 40%. Under these conditions PMSF and Casamino acids are not required. Casamino acids are an animal product and are frowned upon by the FDA. PMSF, a protease inhibitor aided to prevent product breakdown, is toxic and requires additional documentation of its absence from the final product, so these changes aid regulatory approval. Using this methodology the yield is 120 mg/L (see example 41).

Example 23

Use of Methanol/Glycerol Mixed Feed During Methanol Induction

The expression level of the bivalent immunotoxin was positively related to the gain of wet cell density during the first 44 hours of methanol induction. In low-producing cultures, the gain of wet cell density was less than 6.0%. However, in fermentation runs producing more than 25 mg/L of the bivalent immunotoxin, the gain of wet cell density (%) during the first 44 hours of methanol induction was an average of 9.26% (FIG. 14). The gain of wet cell density during methanol induction was hard to achieve without continuous feeding of glycerol as the additional carbon source. Therefore a methanol/glycerol (4:1) mixed feed was used to support cell growth during methanol induction.

Wild type strain X-33 did not produce immunotoxin (FIG. 21A) and served as a control for monitoring methanol consumption and cell growth. This strain had a maximum methanol consumption of 1.95 ml/min at 25° C. This consumption rate was maintained at >70% of the maximum rate for the entire methanol induction phase (FIG. 21A). The wet cell density increased continuously during the 44 h methanol induction. The DT-resistant immunotoxin producing EF-2 mutant strain, mutEF2JC307-8(2) was used as another control for comparing methanol consumption and cell growth upon the secretion of immunotoxin. This EF-2 mutant strain had similar profiles of methanol consumption and wet cell growth to those of wild type strain X-33 during induction (FIG. 21A). The maximum methanol consumption rate and wet cell gain during 44 h of methanol induction were 2.2 ml/min and 9.17%, respectively. However, the use of the EF-2 mutant did not improve immunotoxin secretion under the fermentation conditions for the JW102 strain producing immunotoxin. For strain JW102, the maximum methanol consumption rate was 1.30 ml/min at 25° C. After peaking at 7-8 h following the initiation of methanol induction, the consumption rate decreased to 15% of the maximum rate at 44 h of methanol induction. Within the first 22 h of methanol induction, the methanol consumption rate dropped to <50% of the maximum methanol consumption rate (FIG. 21B). This low level of methanol consumption resulted in less increase in wet cell density, 2.0%, for JW102 than for X-33 (10.5%)

(FIGS. 21A and 21B). There was little or no increase in wet cell density after the first 22 h of methanol induction and the secreted level of immunotoxin decreased from 15 to 10 mg/L. Immunotoxin breakdown products were not detectable on the SDS gels used to monitor product stability.

Example 24

Yeast Extract Feeding, Methanol Consumption, and Immunotoxin Production

The decreased methanol consumption and cell growth rate associated with immunotoxin production can be due to the toxicity of the immunotoxin to *P. pastoris*. If yeast extract was fed continuously to the bioreactor with methanol as the sole carbon source (FIG. 21C), then peak methanol consumption was less than with the wild type strain and the EF-2 mutant strain (FIG. 21A), but the decrease after 10 h was eliminated and cell growth increased throughout the induction period. This growth response was coupled with a loss of immunotoxin in the medium after 8 h, indicating protease activity. Immunotoxin fragments were present at 4 h after induction, and no intact immunotoxin was detected by 19 h after induction (FIG. 22A). If the medium collected at various time points was incubated with purified immunotoxin, then the amount of immunotoxin fragments formed depend on the age of the medium (FIG. 22B). For example, at 49 h post induction the intact immunotoxin band is greatly reduced and the 36.5 kDa band representing degraded fragments is greatly increased relative to samples from earlier time points.

The reduction in methanol utilization that was corrected by yeast extract feeding (FIG. 21C) is apparently secondary to inhibition of protein synthesis by the immunotoxin following ADP-ribosylation of EF-2. This was shown by the fact that a *P. pastoris* strain producing immunotoxin and engineered to toxin resistance in the EF-2 gene (13) consumed methanol at the wild type strain rate (FIG. 21 and FIG. 21 legend). In the toxin-sensitive strain, inhibition of protein synthesis can occur if the immunotoxin gains access to the cytosol compartment where EF-2 resides. Two distinct mechanisms can produce this effect. One mechanism is post-translational translocation where the entire immunotoxin is translated before entering the Sec61 translocon (16). This would provide a brief opportunity for ADP ribosylation of EF-2. Post-translational translocation is common when the signal peptide is alpha mating factor as it is in this case (24). Another mechanism is the well documented proton mediated catalytic domain translocation across an internal membrane compartment (2). This can occur from the mildly acidic Golgi compartment or the more acidic vacuole. Whichever immunotoxin translocation mechanism is dominant, yeast extract feeding either interferes with this step, or with the subsequent ADP-ribosylation of EF-2 either directly or by attenuating the catalytic activity of the translocated toxin A chain Example 25

Addition of Glycerol to the Methanol Feed with Yeast Extract Feeding

The protease activity observed when methanol was the sole carbon source could be a result of leaking from dead or injured cells. When a 4:1 methanol:glycerol feed (FIG. 21D) was substituted for the pure methanol (FIG. 21C) the level of immunotoxin in the medium rose to 20 mg/L at 44 h. Only minimal degradation products now could be detected in SDS gels of proteins in the medium (FIG. 23, far right panel). The methanol-glycerol mixed feed without yeast extract could not sustain the methanol consumption or the continual increase in cell mass, and the final immunotoxin production was to 15 mg/L (FIG. 21E).

Although continuous feeding of yeast extract largely corrected the reduction in methanol metabolism, immunotoxin production was low and was associated with extensive proteolysis (FIGS. 21C and 22). This extensive proteolysis was reversed by providing supplemental carbon in the form of a mixed 4:1 methanol:glycerol feed (FIG. 21D and FIG. 23, panel 23° C.), which increased immunotoxin production to 20 mg/L. It has been reported that there is an optimal maximal specific growth rate during *P. pastoris* methanol fed-batch culture, which when exceeded depresses heterologous protein production (27). Feeding methanol at the optimal rate and adding glycerol at a rate of 20% of the maximal glycerol growth rate increased heterologous protein production by 50% (27). This increase can result from increased metabolism of formaldehyde and $H_2O_2$ and higher activity of catalase and AOX. In the case of secreted proteins these metabolic changes also can reduce the amount of excreted proteases and reduce the number of dead or injured cells leaking proteolytic enzymes.

Example 26

Low Temperature and Secretion of Bivalent Immunotoxin

Figure 15C:
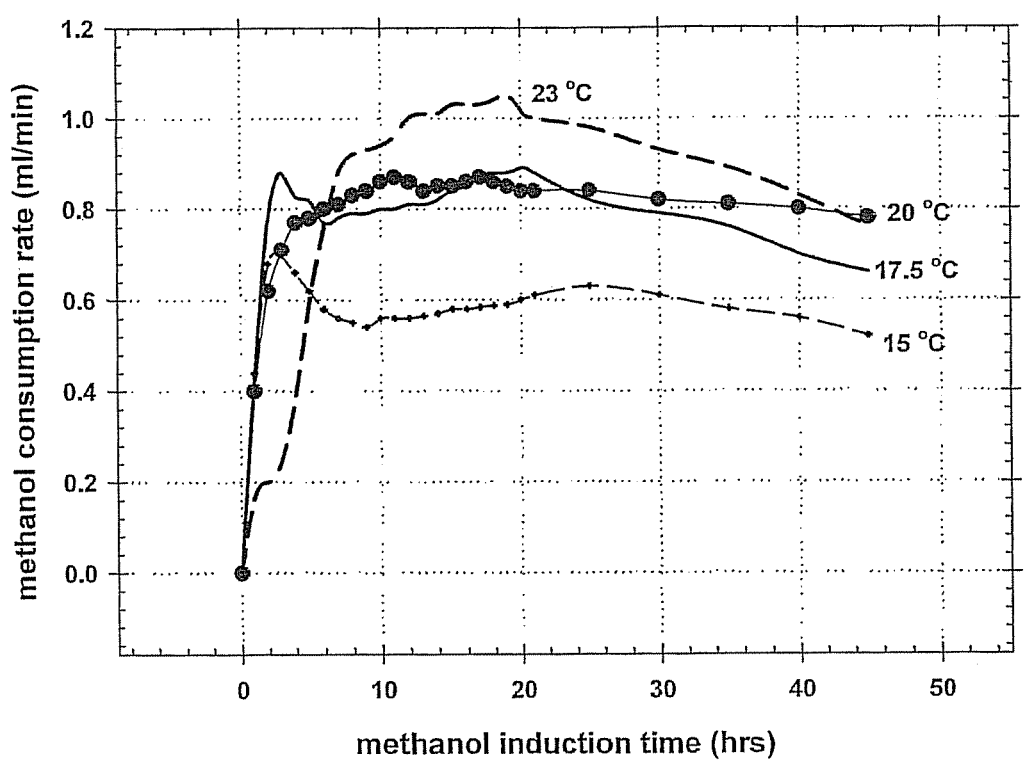

Low temperature can improve the yield of heterologous protein expression in *P. pastoris* either by enhancing protein folding within the ER and/or by reducing medium protease activity (9). At 15° C. methanol consumption at 44 h was reduced by 25%, however cell growth was maintained (FIG. 15C). Immunotoxin production increased by 50% at 44 h (30±0 mg/L, n=3) and almost 100% at 67 h (37±2.9 mg/L, n=3). Most of the increase in immunotoxin secretion occurred between 20-15° C.

The highest expression level was observed at 17.5° C. (FIG. 15A), but the final yield obtained by the 3-step purification procedure of the immunotoxin was the highest at 15° C. (FIG. 15B) and averaged 13.8±1 mg/L (n=3) and 16.0±1 mg/L (n=3) at 44 and 67 h, respectively. The purified immunotoxin produced at 15° C. was fully functional, as confirmed by measuring specific T cell cytotoxicity in protein synthesis assay yielding IC50 values for three individual production runs of 1.2 (±0.1)×10-13 M compared to 2×10-13 M for the average of three runs from shake flask culture.

The amount of degraded immunotoxin bands noted on SDS gels from bioreactor supernatants (all receiving continuous 10 mM PMSF feeding) were reduced from modest levels at 23° C. to undetectable levels at 15° C. (FIG. 23). By using a sensitive assay for serine Ibex-2-like proteases employing a mutant diphtheria toxin (CRM9) substrate, protease activity was undetectable at 67 h at 15° C. although activity was detected at 67 h when PMSF was not infused (FIG. 24). At 15° C. gel patterns and immunotoxin yields were identical whether or not PMSF was infused.

Cell viability of 15° C. bioreactor samples from the methanol-glycerol mixed feed plus yeast extract medium assayed by flow cytometry had a low level of dead cells: 0.7±0.22% (confidence limit 99%) glycerol fed-batch phase; glycerol-methanol mixed feed, 1.2±0.58% (confidence limit 99%) at 22 h, 1.7±0.61% (confidence limit 99%) at 44 h and 1.1±0.51% (confidence limit 99%) at 67 h (the dead cell fraction was determined from one fermentation run). The viable cells showing intracellular esterase activity were present in over 96% of the cells at all time points during methanol induction.

Lowering the induction temperature from 23-25° C. to 15° C. further increased the immunotoxin level to 30 mg/L at 44 h and 37 mg/L at 67 h (FIG. 21F). Low induction temperature was associated with a low and constant level of dead cells during induction (<2.0%) and reduced protease activity toward immunotoxin within the bioreactor even though small amounts of protease activity could be detected by a sensitive assay (FIGS. 23 and 24). These results are consistent with a study utilizing temperature limited (12° C.) fed-batch technique (9). In the temperature limited fed-batch technique, dead cells were reduced from 9% to <1% at 44 h compared to a methanol limited fed-batch process at 30° C. This reduction in dead cells was associated with a marked reduction in degraded product (lipase) and a 2-fold increase in intact product at late time points. These changes were attributed to the avoidance of oxygen deprivation at high cell densities. AOX activity increased more than 2-fold at 67 h in the temperature-limited fed-batch technique Lowering induction temperature can also result in increased immunotoxin secretion by the balancing of immunotoxin input and output through the secretory pathway by reducing the overall protein synthesis rate. In the expression and secretion of heterologous proteins, each protein appears to have an optimal secretion level. Expression beyond the optimal level (overexpression) can reduce secreted protein yields (1, 11, 13, 15). The bivalent immunotoxin also can require a longer processing time for correct folding because of the multi-domain structure of this protein, which has low activity after in vitro refolding following expression in *E. coli* (25). The methanol consumption rate was reduced by only 25% in going from 23° C. to 15° C. and the cell growth rate was unchanged at 44 h.

Example 27

Complex Media for Production of Bivalent Immunotoxin in *Pichia pastoris*

The uses of the complex components in the initial fermentation media were necessary to obtain a reasonable range of the expression level of the bivalent immunotoxin in the fermentor. In the initial fermentation runs, very low production of the bivalent immunotoxin in the fermentor was observed when the standard defined medium was used. Therefore, Soytone Peptone and yeast extract-based medium was developed containing 4% glycerol, 2% yeast extract, 2% Soytone Peptone, 1.34% yeast nitrogen base with ammonium sulfate and without amino acids, 0.43% PTM1 salts solution and 0.01% antifoam 289.

Example 28

Mut+ Versus MutS Phenotype

Different Mut (methanol utilization) phenotype strains derived from *Pichia pastoris* GS115 (Mut+) and KM71 (MutS) were tested to compare the expression level of the bivalent immunotoxin in the fermentor. In the fermentor, the MutS phenotype strain has advantages, such as easy control of induction temperature, no need to supply pure oxygen, and resistance to a high concentration of methanol. Although these two different phenotype strains did not make a difference in the expression level in test tube culture, the expression level of the Mut+ strain in the fermentor was 5~7-fold higher than that of the MutS strain.

Example 29 pH Shifting Procedure Reduces Contaminant Proteins in the Supernatant

There was a great difference between shake flask culture and fermentor culture for the expression of the bivalent immunotoxin. In shake flask culture, it is possible to replace the culture medium with fresh induction medium, resulting in removal of cell membrane fragments, DNA and proteases derived from cell lysis during the growth period and proteins secreted by *Pichia pastoris*. However, those molecules accumulate for the whole period of fermentation and they are often problematic in the purification process.

In order to reduce this kind of problem in the fermentor, a pH shifting procedure was employed. *Pichia pastoris* can normally grow within the range of pH 3~7. *Pichia pastoris* was cultivated at a low pH such as pH 3.5 during the glycerol batch phase and the glycerol-fed batch phase, and induced at pH 7.0 for production of the bivalent immunotoxin. The pH shifting procedure provided the supernatant with the dominant bivalent immunotoxin, because the amount of secreted proteins in *Pichia pastoris* was significantly decreased at low pH even though the expression level of the bivalent immunotoxin was not affected.

Example 30

The Use of Glucose for Tight Control of the AOX1 Promoter

In general, tight gene control is necessary to obtain toxic proteins in host cells. The expression of the bivalent immunotoxin was toxic to *Pichia pastoris*. Since the AOX1 promoter cannot tightly control gene expression in the presence of glycerol as the carbon source, the bivalent immunotoxin was observed before methanol induction on Coomassie stained SDS-polyacrylamide gels. The glycerol-fed batch phase was replaced with a glucose-fed batch phase for tight gene control, because glucose represses AOX1-driven gene expression (Tschopp et al., 1987). However, the replacement of glycerol with glucose in the fed batch phase did not change the final expression level of the bivalent immunotoxin. Glycerol was used during the fed batch phase because glucose took time to dissolve at a high concentration. When combined with the glycerol-fed batch phase, the pH shifting procedure prevented the appearance of the bivalent immunotoxin on Coomassie-stained SDS-polyacrylamide gels during the glycerol-fed batch.

Example 31

Optimal pH for Expression of the Bivalent Immunotoxin

In order to determine optimal pH for the expression of the bivalent immunotoxin, the expression strain JW102 was induced for 24 hours in the range of pH 3.5 to 8.0 in test tube cultures, and the bivalent immunotoxin in the supernatants was compared on a Coomassie-stained SDS-polyacrylamide gel and Western blotting. Sodium citrate buffer (pH 3.5~5.5), bis-tris buffer (pH 6.0~7.0) and tris buffer (pH 7.5~8.0) were used for maintenance of the cultures at the indicated pH.

Simultaneously, colony forming units in the cultures at the end of methanol induction were measured as previously described (Woo et al., 2002). Below pH 6.0, the bivalent immunotoxin was not detectable on Western blots. Although the Western blot shows similar expression levels in the range of pH 6 to 8, the Coomassie-stained SDS-polyacrylamide gel indicates pH 7.0 was the optimum pH level for the expression of the bivalent immunotoxin. *Pichia pastoris* had similar colony forming units in the range of pH 3.5 to 7.0, but the colony forming units were sharply decreased at above pH 7.4. Since pH 7.4 was the upper edge of optimal pH range, the expression level at pH 6.7 was also tested in the fermentor. However, there was no difference in the expression level at pH 6.7 and 7.4.

Example 32

Reproducibility and Cell Viability of Optimized Fermentation Runs

Under the optimized fermentation conditions, the expression level of the bivalent immunotoxin increased to 40 mg/L at 67 hours of methanol induction (FIG. 16). The expression levels in the supernatants at 44 hours and 67 hours of methanol induction, and the final yield obtained by the 3-step purification procedure for the bivalent immunotoxin were reproducible. As shown in Table 4, very similar levels of bivalent immunotoxin were obtained in 3 independent fermentation runs under the optimized conditions. More importantly, the final yields of the purified bivalent immunotoxin were very similar to each other, indicating that produced supernatants had similar quality of the bivalent immunotoxin. Under the optimized fermentation conditions, cell viability during methanol induction phase was maintained at greater than 95% as determined by flow cytometry.

TABLE 4

Reproducibility of optimized fermentation condition[1] and purification[2].

| Run no. | Methanol induction time (hrs) | Expression level (mg/L) | Purified immunotoxin from 1 L supernatant (mg) |
|---------|-------------------------------|-------------------------|------------------------------------------------|
| 1 | 44 | 30 | 16 |
|   | 67 | 40 | 18 |
| 2 | 44 | 30 | 16 |
|   | 67 | 40 | 18 |
| 3 | 44 | 30 | 16 |
|   | 67 | 40 | 18 |

[1]Optimized condition: induction temperature at 15° C.; continuous feeding of 10% yeast extract feeding at 8.95 ml/hr; methanol/glycerol (4:1) mixed feed for methanol induction.
[2]For purification of the bivalent immunotoxin, a 3-step procedure (Woo and Neville, 2003) was used.

Example 33

Relationship Between Induction Time Aid Formation of the Aggregates

Immunotoxin aggregates were accumulated in the supernatant during induction. In order to determine the relationship between induction time and aggregate formation, fractionated samples were taken at 22, 44 and 67 hours of methanol induction by a Superdex 200 gel filtration and then analyzed fractionated samples on SDS-PAGE gels. The 22, 44 and 67 hour samples contained 50.0, 60.0 and 66.7% of dimeric and higher oligomeric forms of the immunotoxin. These aggregate forms of the immunotoxin had only 10% specific toxicity of the monomeric immunotoxin to Jurkat cells.

In addition, the accumulation of immunotoxin aggregates significantly reduced bioactivity of the supernatant. However, bioactivity was recovered by the butyl 650M capturing step developed in a previous study. This result suggested the possibility that some portion of immunotoxin aggregates were reversible.

The use of antifoam agents at a concentration above 0.01% reduced formation of aggregates. These immunotoxin aggregates did not bind well in thiophilic adsorption used as the capture step before developing a 3-step purification procedure. In the initial stages of fermentation optimization, antifoam agents were used at the minimum concentration that could control excessive foaming in the fermentor. However, more than 50% of the bivalent immunotoxin was lost at the first capturing step when antifoam 289 was used at 0.005% in the initial fermentation medium. The use of antifoam 289 at a concentration of more than 0.01% in the initial fermentation medium was crucial to obtain reasonable yields of more than 90% in the first capture step.

Example 34

Protein Quantification by Comparison on SDS-PAGE and Cytotoxicity Assay

The concentration of the immunotoxin was quantified by SDS-PAGE using an immunotoxin standard of known concentration prepared previously (Woo et al., 2002). Samples to be measured were subjected to SDS-PAGE utilizing tris-glycine 4-20% precast gels (Invitrogen) under non-reducing or reducing conditions.

The specific cytotoxicity of the purified anti-human anti-CD3 immunotoxins were performed as described (Neville et al., 1992). Briefly, immunotoxins were applied to Jurkat cells, a human CD3ϵ+ T cell leukemia line, (5×104 cells/well) in 96-well plates in leucine-free RPMI 1640 medium. After 20 hours, a 1 hour pulse of [3H] leucine was given. Cells were collected onto filters with a Skatron harvester.

After addition of scintillant, samples were counted in a Beckman scintillation counter using standard LSC techniques.

Example 35

Butyl 650M Hydrophobic interaction Chromatography (Butyl 650M HIC)

As shown in FIG. 17, Butyl 650M HIC was an efficient capture step for immunotoxin in supernatant. However, glycoproteins were also purified with the immunotoxin during this step. Among these glycoproteins, identified by periodic acid Schiff staining, the glycoprotein species of approximately 45 kDa (arrow in FIG. 17) impeded isolation of the pure immunotoxin. By conventional chromatography such as gel filtration and anion exchange chromatography, these glycoproteins were not separated from the immunotoxin, indicating that these 45 kDa glycoprotein species were present in dimeric form and had similar isoelectric points. Therefore these 45 kDa glycoproteins were very similar to the immunotoxin in size and isoelectric point as well as in hydrophobicity.

Various hydrophobic resins which complied with GMPs (Good Manufacturing Practices) were evaluated. Among these resins, Butyl 650M appeared to have the best binding and eluting profile of the immunotoxin. Other hydrophobic resins may be used in the present invention. Also it was found that 200 mM of sodium sulfate was a suitable concentration for binding of the immunotoxin to the butyl 650M resin.

The fermentor culture normally had approximately 30% of wet cell density at the end of the fermentation run. In large-scale production, the supernatant is obtained by continuous centrifugation requiring a 3-fold dilution of the high cell density culture. The immunotoxin in the diluted sample was processed the same as the immunotoxin in the supernatant which was effectively bound to the Butyl 650M resin at 200 mM sodium sulfate.

Example 36

Poros 50 HQ Anion Exchange Chromatography by Step-Eluting with Sodium Borate Buffer By employing borate anion exchange chromatography, the immunotoxin was successfully separated from the *Pichia pastoris* glycoproteins (FIG. 18). The immunotoxin was bound to anion resin by diluting the sample from the previous step, simplifying the purification procedure. In fractions eluted with 50 mM, 75 mM and 100 mM sodium borate in Buffer B (lane 9, 10, 11 in FIG. 18), most of the immunotoxin was present in monomeric form. These 3 fractions were pooled for the next step.

In order to remove glycoprotein species in the sample obtained from the previous step, sodium borate in anion exchange chromatography was used, because sodium borate increases the negative charge of glycoproteins by binding to the carbohydrate residues of the glycoproteins. The immunotoxin binds to anion exchange resins at pH 8.0 (Woo et al., 2002). Preliminary experiments were designed for optimizing binding conditions of the immunotoxin in the presence of sodium borate. Aliquots of the dialyzed sample against Buffer B were mixed with different volumes of 200 mM sodium borate in Buffer B to obtain the designated concentration of sodium borate. The prepared samples were then loaded onto a Poros 50 HQ anion column (40 ml) equilibrated with Buffer B containing a corresponding concentration of sodium borate. At 100 mM of sodium borate the immunotoxin did not bind to the Poros 50 HQ anion resin, but the majority of glycoproteins still bound. At a concentration of sodium borate below 50 mM, the immunotoxin bound to the Poros 50 HQ anion resin.

Conditions of step elution were further analyzed with sodium borate after binding of the immunotoxin to an anion exchange column. First, the sample dialyzed against Buffer B was bound to the anion column and then eluted in steps of increasing concentration of sodium borate (100, 120, 140, 200 mM) and 1 M NaCl. The bound immunotoxin was mainly eluted at 100 mM sodium borate, but these eluted fractions also contained significant amounts of 45 kDa glycoproteins which were not separable in the next step. The majority of glycoproteins were eluted at 1 M NaCl. After loading the same sample as the first experiment, the bound immunotoxin was eluted in steps of 50, 75 and 100 mM sodium borate and 1 M NaCl. A majority of the bound immunotoxin was eluted at 75 mM sodium borate. However, a protein band corresponding to 21 kDa was included in the fraction eluted with 50 mM sodium borate. After binding to the column, the bound immunotoxin was eluted in steps of 25, 50, 75 and 100 mM sodium borate and 1 M NaCl in Buffer B (FIG. 18). By washing with 25 mM sodium borate buffer, the amount of a protein band corresponding to 21 kDa was reduced.

Example 37

Comparison with Phenylboronate Affinity Chromatography

In order to compare separation profiles, phenylboronate affinity chromatography was performed. The eluant from the butyl 650M HTC capture step was dialyzed against the low ionic strength buffer (10 mM HEPES, 0.25 mM EDTA and 20 mM MgCl2, pH 8.2) for phenylboronate affinity chromatography. The dialysed sample was applied to a 5 ml bed volume column of phenylboronate agarose (Sigma Co.), washed with the same buffer, and then the bound proteins were eluted with either 0-100 M sodium borate gradient or 0-50 mM sorbitol gradient in the same buffer (20 bed volumes). Glycoproteins and the immunotoxin were bound under binding condition of low ionic strength. The glycoproteins and immunotoxin were not separated by phenylboronate affinity chromatography. The glycoproteins and immunotoxin were co-eluted with either 0-100 mM sodium borate gradient or 0-50 mM sorbitol gradient.

Example 38

Q Anion Exchange Chromatography

Q anion exchange chromatography was used for concentration of the diluted sample that was obtained from the Poros 50 HQ anion exchange chromatography. At a concentration of sodium borate below 50 mM the immunotoxin was bound to the anion exchange resin. Accordingly, the pooled sample from the previous step was diluted with 3 sample volumes of TE buffer (20 mM Tris-Cl and 1 mM EDTA, pH 8.0), resulting in less than 20 mM of sodium borate in the diluted sample. As expected, the immunotoxin was effectively bound to the Q anion exchange column. The bound immunotoxin was eluted with 0~400 mM NaCl gradient elution (20 column volumes). The immunotoxin fractions were pooled and then assessed for yield, purity and toxicity of the final preparation by SDS-PAGE and protein synthesis assay.

Example 39

Protein Yield, Repeatability of Purification Procedure, Purity and Function of the Purified Immunotoxin Table 4 summarizes the immunotoxin yields which were obtained in 3 batches of the 3-step purification runs by using the supernatants taken at 44 hours of methanol induction from 3 fermentation runs which were carried out under relatively similar fermentation conditions and had similar expression levels of the immunotoxin. The average yield of this purification batch was 52.8%. By using the 3-step purification procedure, approximately 16 mg of the purified material from 1 liter of supernatant was obtained. The starting supernatants had different levels of immunotoxin aggregates and monomeric immunotoxin depending on the induction time during fermentation run. Among these immunotoxin aggregates, some portions could be reversible to monomeric form of the immunotoxin during the Butyl 650M HIC step. Fractionation of supernatant by gel filtration and subsequent SDS-PAGE analysis showed that the supernatants contained more than 50% of the immunotoxin aggregates. However, the final yield of the immunotoxin after the 3-step purification procedure was 52.8%, indicating that a portion of the aggregates could be dissociated into monomeric immunotoxin during purification.

A comparison of the purification procedure applied to 3 separate fermentation runs that contained similar amounts of supernatant immunotoxin demonstrates good repeatability of the procedure with respect to yields (Table 5).

The purity of the purified immunotoxin was assessed by analytical gel filtration. The immunotoxin in the final preparation displayed a single peak corresponding to the monomeric form of the immunotoxin (panel A in FIG. 19). The analyses of purity of the final preparations confirmed that the 3-step purification yielded an immunotoxin with ~98.0% purity (panel B in FIG. 19).

To investigate the effects of the 3-step purification procedure on immunotoxin bioactivity, a protein synthesis assay for the specific T cell toxicity of the final preparation was performed. The estimated concentration of the immunotoxin in the final preparation coincided with concentration of the immunotoxin standard.

TABLE 5

Comparison of immunotoxin purification from *Pichia pastoris* fermentor cultures*.

| Batch no. | step | IT conc (ug/ml) | volume (ml) | total IT (mg) | yield (%) | acc. yield (%) |
|---|---|---|---|---|---|---|
| 1 | Supernatant | 30.0 | 1000 | 30.0 | 100.0 | 100.0 |
|   | Butyl 650M HIC | 45.0 | 585 | 26.3 | 87.8 | 87.8 |
|   | Poros 50 HQ borate AEX | 15.0 | 1200 | 18.0 | 67.0 | 60.0 |
|   | Q AEX | 400.0 | 40 | 16.0 | 88.9 | 53.3 |
| 2 | Supernatant | 30.0 | 1000 | 30.0 | 100.0 | 100.0 |
|   | Butyl 650M HIC | 40.0 | 585 | 23.4 | 78.0 | 78.0 |
|   | Poros 50 HQ borate AEX | 15.0 | 1200 | 17.5 | 74.6 | 58.2 |
|   | Q AEX | 400.0 | 40 | 16.0 | 91.6 | 53.3 |
| 3 | Supernatant | 30.0 | 1000 | 30.0 | 100.0 | 100.0 |
|   | Butyl 650M HIC | 40.0 | 585 | 23.4 | 78.0 | 78.0 |
|   | Poros 50 HQ borate AEX | 15.0 | 1200 | 18.0 | 67.0 | 60.0 |
|   | Q AEX | 450.0 | 35 | 15.8 | 87.5 | 52.5 |

*IT, immunotoxin; acc., accumulated; HIC, hydrophobic interaction chromatography; AEX, anion exchange chromatography. Supernatants were obtained from 3 fermentation runs at 44 hours of methanol induction.

Example 40

Summary

Glycerol feeding decreased immunotoxin proteolysis and enhanced immunotoxin production while yeast extract feeding primarily enhanced methanol utilization and cell growth. Glycerol feeding and yeast extract feeding acted synergistically to increase immunotoxin production and this synergy was enhanced at 15° C.

This study demonstrates a synergy between carbon source supplementation with glycerol and continuous yeast extract feeding that attenuates the toxic effects of the immunotoxin and increases production, especially at 15° C. This robust process has a yield of 37 mg/L, 7-fold greater than that previously reported in the toxin-resistant CHO cell expression system (25).

Example 41

The final method uses the toxin resistant EF-2 mutant, limited methanol feeding during induction of 0.5 to 0.75 ml/min (per 10 L initial medium) without an additional carbon source, extension of induction time to 163 h, a temperature of 15° C., a continuous infusion of yeast extract, limitation of agitation speed to 400 RPM, addition of antifoam agent up to 0.07%, and supplementation of oxygen when DO levels fall below 40%. Under these conditions PMSF and Casamino acids are not required. Additionally, reducing shearing force by lowering agitation speed and adding anti-foam reagent dramatically reduced immunotoxin aggregation. As a result, purification yield was improved from 64 to 76%. Under this optimized methodology, immunotoxin secretion level was 120 mg/L at 163 hr of methanol induction. Table 6 summarizes how much immunotoxin secretion and purification yield were improved by solving the major problems. Gene optimization enhanced IT secretion from non-detectable level to 10 mg/L. By using DT-resistant strain and employing low temperature, we improved immunotoxin secretion up to 35 mg/L. Furthermore, employing limited methanol feeding improved immunotoxin secretion as well as purification yield. Finally, extension of induction time and addition of anti-foam reagent dramatically increased immunotoxin secretion and purification yield. The anti-foam reagent is KFOTM 673 which was purchased from Kabo Chemical, Inc. (Cheyennne, Wyo. 82007, USA). This methodology can be useful for the production of other recombinant immunotoxins and other toxic proteins in toxin-sensitive *P. pastoris*.

TABLE 6

Increase in immunotoxin secretion and purification yield by solving major problems

| solutions | IT secretion level | Purification yield |
|---|---|---|
| Gene optimization | 10.0 mg/L | n.a. |
| Use of DT-resistant strain & low temperature | 35.0 mg/L | 14.5 mg/L (41.4%) |
| Limited methanol feeding | 50.0 mg/L | 32.0 mg/L (64.0%) |
| Extended induction time & addition of anti-foam reagent | 120.0 mg/L | 90.8 mg/L (75.7%) |

Throughout this application various publications are referenced. Full citations for these publications are as follow. Such publications mentioned are hereby incorporated in their entirety by reference in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Arata, Y., T. Nishi, S. Kawasaki-Nishi, E. Shao, S. Wilkens, and M. Forgac. 2002. Structure, subunit function and regulation of the coated vesicle and yeast vacuolar (H(+))-ATPases. Biochim. Biophys. Acta 1555:71-4.

Bannister, S. J., and K. D. Wittrup. 2000. Glutathione excretion in response to heterologous protein secretion in *Saccharomyces cerevisiae*. Biotechnol. Bioeng. 68:389-95.

Bennett, M. J., and D. Eisenberg. 1994. Refined structure of monomeric diphtheria toxin at 2.3A resolution. Protein Science 3:1464-1475.

Boeseken, J. 1949. The use of boric acid for the determination of the configuration of carbohydrates. Adv. Carbohydr. Chem. 4:189-210.

Bouriotis, V., Scott, J., Galloway, A., Bellingham, A. J., and Dean, P. D. 1981. Measurement of glycosylated haemoglobins using affinity chromatography. Diabetologia 21:579-580.

Cereghino, G. P., Cereghino, J. L., Ilgen, C. and Cregg, J. M. 2002. Production of recombinant proteins in fermentor cultures of the yeast *Pichia pastoris*. Curr. Opin. Biotechnol. 13:329-332.

Cereghino, G. P., Cereghino, Sunga, A. J., Johnson, M. A., Lim, M., Gleeson, M. A. G. and Cregg, J. M. (2001) New selectable marker/auxotrophic host strain combinations for molecular genetic manipulation of *Pichia pastoris*. Gene 263, 159-169.

Che, F. Y., J. F. Song, X. X. Shao, K. Y. Wang and Q. C. Xia. 1999. Comparative study on the distribution of ovalbumin glycoforms by capillary electrophoresis. J. Chromatogr. A 849:599-608.

Chen, J. Y. C., Bodley, J. W. and Livingston, D. W. (1985) Diphtheria toxin-resistant mutants of *Saccharomyces cerevisiae*. Mol. Cell. Biol. 5, 3357-3360.

Chen, S. R., D. D. Dunigan, and M. B. Dickman. 2003. Bcl-2 family members inhibit oxidative stress-induced programmed cell death in *Saccharomyces cerevisiae*. Free Radic. Biol. Med. 34:1315-1325.

Collier, J. (1975) Diphtheria toxin: mode of action and structure. Bact. Rev. 39, 54-85.

Conover, W. J. 1999. Some tests based on the binomial distribution, p. 123-178. In B. Wiley (ed.), Practical nonparametric statistics, 3rd ed. John Wiley and Sons, Inc., New York, N.Y.

Couderc, R., and J. Baratti. 1980. Oxidation of methanol by the yeast, *Pichia pastoris*. Purification and properties of the alcohol oxidase. Agric. Biol. Chem. 44:2279-2289.

Davis, C. A., Grate, L., Spingola, M. and Ares Jr., M. (2000) Test of intron predictions reveals novel splice sites, alternatively spliced mRNAs and new introns in meiotically regulated genes of yeast. Nucleic Acids Research 28, 1700-1706.

Desai, U. R., H. Wang, S. A. Ampofo and R. J. Linhardt. 1993. Oligosaccharide composition of heparin and low-molecular-weight heparins by capillary electrophoresis. Anal. Biochem. 213:120-127.

Döring, F., Klapper, M., Theis, S, and Daniel, H. (1998) Use of the glyceraldehyde-3-phosphate dehydrogenase promoter for production of functional mammalian membrane transport proteins in the yeast *Pichia pastoris*. Biochem. Biophys. Res. Commun. 250, 531-535.

Foley, B. T., Moehring, J. M., and Moehring, T. J. (1992) A mutation in codon 717 of the Cho-K1 elongation factor 2 gene prevents the first step in the biosynthesis of diphthamide. Somat. Cell Mol. Genet. 18, 227-231

Frankel, A. E., D. M. Neville, T. A. Bugge, R. J. Kreitman, and S. H. Leppla. 2003. Immunotoxin therapy of hematologic malignancies. Semin. Oncol. 30:545-557.

Gellissen, G. (2000) Heterologous protein production in methylotrophic yeasts.

Hardy, E., E. Martinez, D. Diago, R. Diaz, D. Gonzalez, and L. Herrera. 2000. Large-scale production of recombinant hepatitis B surface antigen from *Pichia pastoris*. J. Biotechnol. 77:157-67.

Houchins, J. P. (2000) Immunotoxin-induced apoptosis. Stem Cell 18, 384-385.

Hu, V. W., and R. K. Holmes. 1987. Single mutation in the A domain of diphtheria toxin results in a protein with altered membrane insertion behavior. Biochim Biophys Acta 902:24-30.

Jahic, M., F. Wallberg, M. Bollok, P. Garcia, and S. O. Enfors. 2003. Temperature limited fed-batch technique for control of proteolysis in *Pichia pastoris* bioreactor cultures. Microb. Cell Fact. 2:6.

Jahic, M., J. C. Rotticci-Mulder, M. Martinelle, K. Hult, and S. O. Enfors. 2002. Modeling of growth and energy metabolism of *Pichia pastoris* producing a fusion protein. Bioprocess Biosyst. Eng. 24:385-393.

Kimata, Y. and Kohno, K. (1994) Elongation factor 2 mutants deficient in diphthamide formation show temperature-sensitive cell growth. J. Biol. Chem. 269, 13497-13501.

Kimata, Y., Harashima, S, and Kohno, K. (1993) Expression of non-ADP-ribosylatable, Diphtheria toxin-resistant elongation factor 2 in *Saccharomyces cerevisiae*. Biochem. Biophys. Res. Commun. 191, 1145-1131.

Kohno, K. and Uchida, T. (1987) Highly frequent single amino acid substitution in mammalian elongation factor 2 (EF-2) results in expression of resistance to EF-2-ADPribosylating Toxins. J. Biol. Chem. 262, 12298-12305.

Kohno, K., Uchida, T., Ohkubo, H., Nakanishi, S., Nakanishi, T., Fukui, T., Ohtsuka, E., Ikehara, M. and Okada, Y. (1986) Amino Acid Sequence of Mammalian Elongation Factor 2 Deduced from the cDNA Sequence: Homology with GTP-Binding Proteins. Proc. Natl. Acad. Sci. U.S.A. 83, 4978-4982.

Li, Z., F. Xiong, Q. Lin, M. d'Anjou, A. J. Daugulis, D. S. Yang, and C. L. Hew. 2001. Low-temperature increases the yield of biologically active herring antifreeze protein in *Pichia pastoris*. Protein Expr. Purif. 21:438-45.

Liebman, J. M., D. LaSala, W. Wang, and P. M. Steed. 1999. When less is more: enhanced baculovirus production of recombinant proteins at very low multiplicities of infection. Biotechniques 26:36-8, 40, 42.

Liu, Y. Y., Gordienko, I., Mathias, A., Ma, S., Thompson, J., Woo, J. H., and Neville, D. M., Jr. (2000) Expression of an anti-CD3 single-chain immunotoxin with a truncated diphtheria toxin in a mutant CFIO cell line. Protein Expr. Purif. 19, 304-11.

Liu, Y. Y., J. H. Woo, and D. M. Neville. 2003. Targeted introduction of a diphtheria toxin resistant mutation into the chromosomal EF-2 locus of *Pichia pastoris* and expression of immunotoxin in the EF-2 mutants. Protein Expr. Purif., in press.

Liu, Y. Y., J. H. Woo, and D. M. Neville. 2003. Targeted introduction of a diphtheria toxin resistant mutation into the chromosomal EF-2 locus of *Pichia pastoris* and expression of immunotoxin in the EF-2 mutants. Protein Expr. Purif. 30:262-274.

Mattheakis, L. C., Shen, W. H. and Collier, R. J. (1992) DPG5, a Methyltransferase gene required for Diphthamide biosynthesis in *Saccharomyces cerevisiae*. Mol. Cell. Biol. 12 4026-4037.

Mita K, Morimyo M, Ito K, Sugaya K, Ebihara K, Hongo E, Higashi T, Hirayama Y, Nakamura Y. (1997) Comprehensive cloning of *Schizosaccharomyces pombe* genes encoding translation elongation factors. Gene 187, 259-266.

Myohanen, T. A., V. Bouriotis and P. D. Dean. 1981. Affinity chromatography of yeast alpha-glucosidase using ligand-mediated chromatography on immobilized phenylboronic acids. Biochem. J. 197:683-688.

Narasimhan, S., N. Harpaz, G. Longmore, J. P. Carver, A. A. Grey and H. Schachter. 1980. Control of glycoprotein synthesis. The purification by preparative high voltage paper electrophoresis in borate of glycopeptides containing high mannose and complex oligosaccharide chains linked to asparagine. J. Biol. Chem. 255:4876-4884.

Neville, D. M., J. Scharff, and K. Srinivasachar. 1992. In vivo T-cell ablation by a holo-immunotoxin directed at human CD3. Proc. Natl. Acad. Sci. USA 89:2585-2589.

Nokelainen, M., H. Tu, A. Vuorela, H. Notbohm, K. I. Kivirikko, and J. Myllyharju. 2001. High-level production of human type I collagen in the yeast Pichia pastoris. Yeast 18:797-806.

Nomoto, H. and Y. Inoue. 1983. A novel glycoasparagine isolated from an ovalbumin glycopeptide fraction (GP-IV). Anion-exchange borate chromatography and structural analysis of GP-IV glycoasparagines. Eur. J. Biochem. 135: 243-250.

Nomoto, H., T. Endo and Y. Inoue. 1982. Preparation and characterisation of fragment glycoasparagines from ovalbumin glycopeptides: reference compounds for structural and biochemical studies of the oligo-mannose and hybrid types of carbohydrate chains of glycoproteins. Carbohydr. Res. 107:91-101.

Ormerod, M. G. 2000. Further applications to cell biology, p. 249-258. In M. G. Ormerod (ed.), Flow cytometry, A practical approach, 3rd ed. Oxford University Press, New York.

Otsuka, H., E. Uchimura, H. Koshino, T. Okano and K. Kataoka. 2003. Anomalous Binding Profile of Phenylboronic Acid with N-Acetylneuraminic Acid (Neu5Ac) in Aqueous Solution with Varying pH. J. Am. Chem. Soc. 125:3493-3502.

Paiva, P. M., A. F. Souza, M. L. Oliva, J. F. Kennedy, M. S. Cavalcanti, L. C. Coelho and C. A. Sampaio. 2003. Isolation of a trypsin inhibitor from Echinodorus paniculatus seeds by affinity chromatography on immobilized Cratylia mollis isolectins. Bioresour. Technol. 88:75-79.

Pendse, G. J., S. Karkare, and J. E. Bailey. 1992. Effect of cloned gene dosage on cell growth and hepatitis B surface antigen synthesis and secretion in recombinant CHO cells. Biotechnol. Bioeng. 40:119-129.

Perentesis, J. P., Phan, L. D., Gleason, W. B., LaPorte, D. C., Livingston, D. M. and Bodley, J. W. (1992) Saccharomyces cerevisiae Elongation Factor 2: genetic cloning, characterization of expression, and G-domain modeling. J. Biol. Chem. 267, 1190-1197.

Phan, L. D., Perentesis, J. P. and Bodley, J. W. (1993) Saccharomyces cerevisiae Elongation Factor 2: mutagenesis of the histidine precursor of diphthamide yields a functional protein that is resistant to diphtheria toxin. J. Biol. Chem. 268, 8865-8868.

Potter, K. J., W. Zhang, L. A. Smith, and M. M. Meagher. 2000. Production and purification of the heavy chain fragment C of botulinum neurotoxin, serotype A, expressed in the methylotrophic yeast Pichia pastoris. Protein Expr. Purif. 19:393-402.

Ratts, R., H. Zeng, E. A. Berg, C. Blue, M. E. McComb, C. E. Costello, J. C. VanderSpek, and J. R. Murphy. 2003. The cytosolic entry of diphtheria toxin catalytic domain requires a host cell cytosolic translocation factor complex. J Cell Biol 160:1139-1150.

Rothman, R. J. and L. Warren. 1988. Analysis of IgG glycopeptides by alkaline borate gel filtration chromatography. Biochim. Biophys. Acta 955:143-153.

Rymond, B. C., and Rosbash, M. (1992). Yeast pre-mRNA splicing. In The Molecular and Cellular Biology of the Yeast *Saccharomyces*: Gene Expression. E. W. Jones, J. R. Pringle, and J. R. Broach, eds. (Cold Spring Harbor, N.Y.: Cold Spring Harbor Laboratory Press), pp. 143-192.

Sambrook, J., Fritsch. E. F. and Maniatis, T. (1989) Molecular Cloning, A Laboratory Manual 2nd edition. (Cold Spring Harbor, N.Y.: Cold Spring Harbor Laboratory Press) pp 8.21-8.35.

Schroder, M., J. S. Chang, and R. J. Kaufman. 2000. The unfolded protein response represses nitrogen-starvation induced developmental differentiation in yeast. Genes Dev. 14:2962-2975.

Scocca, J. R. 1986. Identification of N-acetylhexosamines produced by enzymes of the N-acetylneuraminic acid metabolic pathway by borate complex anion-exchange chromatography of the corresponding N-acetylhexosaminitols. Anal. Biochem. 156:61-66.

Thompson, J., H. Hu, J. Scharff, and D. M. Neville. 1995. An anti-CD3 single-chain immunotoxin with a truncated diphtheria toxin avoids inhibition by pre-existing antibodies in human blood. J. Biol. Chem. 270:28037-28041.

Thompson, J., Stavrou, S., Weetall, M., Hexham, J. M., Digan, M. E., Wang, Z., Woo, J. H., Yu, Y., Mathias, A., Liu, Y. Y., Ma, S., Gordienko, I., Lake, P. and D. M. Neville, Jr. 2001. Improved binding of a bivalent single-chain immunotoxin results in increased efficacy for in vivo T-cell depletion. Protein Eng. 14:1035-1041.

Thorburn, J., A. E. Frankel, and A. Thorburn. 2003. Apoptosis by leukemia cell-targeted diphtheria toxin occurs via receptor-independent activation of Fas-associated death domain protein. Clin. Cancer Res. 9:861-865.

Tschopp, J. F., P. F. Brust, J. M. Cregg, C. A. Stillman, and T. R. Gingeras. 1987. Expression of the lacZ gene from two methanol-regulated promoters in *Pichia pastoris*. Nucleic Acids Res. 15:3859-76.

Valkonen, M., M. Penttila, and M. Saloheimo. 2003. Effects of inactivation and constitutive expression of the unfolded-protein response pathway on protein production in the yeast *Saccharomyces cerevisiae*. Appl. Environ. Microbiol. 69:2065-2072.

Veenhuis, M., J. P. Van Dijken, and W. Harder. 1983. The significance of peroxisomes in the metabolism of one-carbon compounds in yeasts. Adv. Microb. Physiol. 24:1-82.

Wang, Y., Z. H. Liang, Y. S. Zhang, S. Y. Yao, Y. G. Xu, Y. H. Tang, S. Q. Zhu, D. F. Cui, and Y. M. Feng. 2001. Human insulin from a precursor overexpressed in the methylotrophic yeast *Pichia pastoris* and a simple procedure for purifying the expression product. Biotechnol. Bioeng. 73:74-9.

Weigel, H. 1963. Paper electrophoresis of carbohydrates. Adv. Carbohyd. Chem. 18:61-97.

Weith, H. L., J. L. Wiebers and P. T. Gilham. 1970. Synthesis of cellulose derivatives containing the dihydroxyboryl group and a study of their capacity to form specific complexes with sugars and nucleic acid components. Biochemistry 9:4396-4401.

Werten, M. W., T. J. van den Bosch, R. D. Wind, H. Mooibroek, and F. A. de Wolf. 1999. High-yield secretion of recombinant gelatins by *Pichia pastoris*. Yeast 15:1087-96.

Willer, M., A. J. Jermy, G. J. Steel, H. J. Garside, S. Carter, and C. J. Stirling. 2003. An in vitro assay using overexpressed yeast SRP demonstrates that cotranslational translocation is dependent upon the J-domain of Sec63p. Biochemistry 42:7171-7177.

Williams, G. T., A. P. Johnstone, V. Bouriotis and P. D. Dean. 1981. Affinity chromatography of membrane proteins on dihydroxyboryl-matrix gel. Biochem. Soc. Trans. 9:137-139.

Woo, J. H., and D. M. Neville. 2003. Separation of bivalent anti-T cell immunotoxin from *P. pastoris* glycoproteins by borate anion exchange. BioTechniques 35:392-398.

Woo, J. H., Y. Y. Liu, A. Mathias, S. Stavrou, Z. Wang, J. Thompson, and D. M. Neville. 2002. Gene optimization is necessary to express a bivalent anti-human anti-T cell immunotoxin in to *Pichia pastoris*. Protein Expr. Purif. 25:270-82.

Woo, J. H., Y. Y. Liu, and D. M. Neville. 2004. Increasing secretion of a bivalent anti-T cell immunotoxin by *Pichia pastoris*. Appl. Environ. Microbiol. 70(6):3370-3376.

Zanette, D., A. Soffientihi, C. Sottani and E. Sarubbi. 2003. Evaluation of phenylboronate agarose for industrial-scale purification of erythropoietin from mammalian cell cultures. J. Biotechnol. 101:275-287.

Zhang, W., K. J. Hywood Potter, B. A. Plantz, V. L. Schlegel, L. A. Smith, and M. M. Meagher. 2003. *Pichia pastoris* fermentation with mixed-feeds of glycerol and methanol: growth kinetics and production improvement. J. Ind. Microbiol. Biotechnol. 30:210-215.

What is claimed is:

1. A method of purifying a non-glycosylated immunotoxin expressed in *Pichia pastoris* comprising
   a) loading a solution containing the non-glycosylated immunotoxin onto a hydrophobic interaction column;
   b) obtaining a first eluent comprising the non-glycosylated immunotoxin from the hydrophobic interaction column;
   c) loading the non-glycosylated immunotoxin containing eluent from step (b) onto a first anion exchange column;
   d) obtaining a second eluent comprising the non-glycosylated immunotoxin from the first anion exchange column by eluting the non-glycosylated immunotoxin from the first anion exchange column with a sodium borate solution, wherein the concentration of the sodium borate solution is between 50 mM and 200 mM;
   e) diluting the concentration of sodium borate in the second eluent from step (d) to 50 mM or less;
   f) concentrating the diluted second eluent from step (e) over a second anion exchange column; and
   g) obtaining the purified non-glycosylated immunotoxin from the second anion exchange column.

2. The method of claim 1, wherein the immunotoxin is a fusion protein.

3. The method of claim 1, wherein the immunotoxin comprises a diphtheria toxin moiety.

4. The method of claim 3, wherein the diphtheria toxin moiety is truncated.

5. The method of claim 4, further comprising a CD3 antibody moiety.

6. The method of claim 5, wherein the non-glycosylated immunotoxin comprises A-dmDT390-bisFv(G4S).

7. The method of claim 1, further comprising washing the first anion exchange column with about 25 mM sodium borate solution prior to eluting with the sodium borate solution.

8. The method of claim 1, wherein the concentration of the sodium borate solution in step (d) is between about 50 mM and about 100 mM.

9. The method of claim 8, wherein the concentration of the sodium borate solution in step (d) is between about 75 mM and about 100 mM.

10. The method of claim 1, wherein the concentration of sodium borate in step (e) is about 20 mM.

* * * * *

SEQUENCE LISTING

```
<160> NUMBER OF SEQ ID NOS: 35

<210> SEQ ID NO 1
<211> LENGTH: 22
<212> TYPE: PRT
<213> ORGANISM: H. sapiens

<400> SEQUENCE: 1

Asp Val Thr Leu His Ala Asp Ala Ile His Arg Gly Gly Gly Gln Ile
1               5                   10                  15

Ile Pro Thr Ala Arg Arg
            20

<210> SEQ ID NO 2
<211> LENGTH: 22
<212> TYPE: PRT
<213> ORGANISM: M. musculus

<400> SEQUENCE: 2

Asp Val Thr Leu His Ala Asp Ala Ile His Arg Gly Gly Gly Gln Ile
1               5                   10                  15

Ile Pro Thr Ala Arg Arg
            20

<210> SEQ ID NO 3
<211> LENGTH: 22
<212> TYPE: PRT
<213> ORGANISM: R. norvegicus

<400> SEQUENCE: 3

Asp Val Thr Leu His Ala Asp Ala Ile His Arg Gly Gly Gly Gln Ile
1               5                   10                  15

Ile Pro Thr Ala Arg Arg
            20

<210> SEQ ID NO 4
<211> LENGTH: 22
<212> TYPE: PRT
<213> ORGANISM: C. griseus

<400> SEQUENCE: 4

Asp Val Thr Leu His Ala Asp Ala Ile His Arg Gly Gly Gly Gln Ile
1               5                   10                  15

Ile Pro Thr Ala Arg Arg
            20

<210> SEQ ID NO 5
<211> LENGTH: 22
<212> TYPE: PRT
<213> ORGANISM: D. melanogaster
```

```
<400> SEQUENCE: 5

Asp Val Thr Leu His Ala Asp Ala Ile His Arg Gly Gly Gly Gln Ile
 1               5                  10                  15

Ile Pro Thr Thr Arg Arg
            20

<210> SEQ ID NO 6
<211> LENGTH: 22
<212> TYPE: PRT
<213> ORGANISM: C. elegans

<400> SEQUENCE: 6

Asp Val Thr Leu His Ala Asp Ala Ile His Arg Gly Gly Gly Gln Ile
 1               5                  10                  15

Ile Pro Thr Ala Arg Arg
            20

<210> SEQ ID NO 7
<211> LENGTH: 22
<212> TYPE: PRT
<213> ORGANISM: S. pombe

<400> SEQUENCE: 7

Asp Val Val Leu His Ala Asp Ala Ile His Arg Gly Gly Gly Gln Ile
 1               5                  10                  15

Ile Pro Thr Ala Arg Arg
            20

<210> SEQ ID NO 8
<211> LENGTH: 22
<212> TYPE: PRT
<213> ORGANISM: P. pastoris

<400> SEQUENCE: 8

Asp Val Thr Leu His Ala Asp Ala Ile His Arg Gly Gly Gly Gln Val
 1               5                  10                  15

Ile Pro Thr Met Lys Arg
            20

<210> SEQ ID NO 9
<211> LENGTH: 22
<212> TYPE: PRT
<213> ORGANISM: S. cerevisiae

<400> SEQUENCE: 9

Asp Val Thr Leu His Ala Asp Ala Ile His Arg Gly Gly Gly Gln Ile
 1               5                  10                  15

Ile Pro Thr Met Arg Arg
            20

<210> SEQ ID NO 10
<211> LENGTH: 66
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10
gatgttaccc tgcacgccga tgctatccac cgccgcggag acaagtcat tccaaccatg    60 aagaga                                                              66
```

<210> SEQ ID NO 11
<211> LENGTH: 223
<212> TYPE: DNA
<213> ORGANISM: Artificial Sequence
<220> FEATURE:
<223> OTHER INFORMATION: Description of Artificial Sequence; note = synthetic construct

<400> SEQUENCE: 11

| | |
|---|---|
| actttgaagt tcttaattt gttcctcgta gaaagaacgc atagataatt caaaatggca | 60 |
| aaatgggtat gtgtttttt atagttcatg tgccgaacaa ctaccgtttt aacttcactg | 120 |
| tcgatcagat gcgatcctt atggacaagg tgtccaacgt ccgtaacatg tcggttattg | 180 |
| cccacgttga tcacggtaag tccactttaa ctgactccct ggt | 223 |

<210> SEQ ID NO 12
<211> LENGTH: 250
<212> TYPE: DNA
<213> ORGANISM: Artificial Sequence
<220> FEATURE:
<223> OTHER INFORMATION: Description of Artificial Sequence; note = synthetic construct

<400> SEQUENCE: 12

| | |
|---|---|
| actttgaagt tcttaattt gttcctcgta gaaagaacgc atagataatt caaaatgggt | 60 |
| atgtgttttt ttatagttca tgtgccgaac aactaccgtt tcaagatggg agccagccac | 120 |
| taacatctcc tctagttaac ttcactgtcg atcagatgcg atcccttatg gacaaggtga | 180 |
| ccaacgtccg taacatgtcg gttattgccc acgttgatca cggtaagtcc actttaactg | 240 |
| actccctggt | 250 |

<210> SEQ ID NO 13
<211> LENGTH: 2601
<212> TYPE: DNA
<213> ORGANISM: Artificial Sequence
<220> FEATURE:
<223> OTHER INFORMATION: Description of Artificial Sequence; note = synthetic construct

<400> SEQUENCE: 13

| | |
|---|---|
| atggttaact tcactgtcga tcagatgcga tcccttatgg acaaggtgac caacgtccgt | 60 |
| aacatgtcgg ttattgccca cgttgatcac ggtaagtcca ctttaactga ctccctggtg | 120 |
| caacgtgccg gtattatttc tgctgccaag gctggtgagg cccgtttcac tgatactaga | 180 |
| aaggacgagc aagagagagg tatcaccatc aagtctaccg ccatttctt gtactctgag | 240 |
| atgggtgacg acgatgtcaa ggagatcaag cagaagactg aagtaacag tttccttatc | 300 |
| aacttaattg actccccagg tcacgttgac ttctcttctg aggtcactgc tgctctgcgt | 360 |
| gttactgacg gtgctttggt cgtcgttgac tgtgttgaag gtgtctgtgt tcaaactgag | 420 |
| accgttttgc gtcaagcttt gggtgaaaga atcaagccag ttgttgtcat taacaaggtc | 480 |
| gaccgtgctc ttttggagtt gcaagttacc aaggaggacc tgtaccagtc tttcgctaga | 540 |
| accgtcgagt ccgtaaacgt cgttatcgct acttacactg acaagaccat ggtgacaac | 600 |
| caagtctacc cagaacaggg taccgtcgct ttcggttcag gtctgcacgg atgggctttc | 660 |
| accgttagac agttcgccac tagatactcc aagaagttcg gtgttgacag aatcaagatg | 720 |
| atggagcgtc tgtggggaga ctcttacttc aacccaaaga ccaagaaatg gaccaacaag | 780 |
| gacaaggacg ccgctggaaa gcctttggag cgtgccttca catgttcgt tttggaccct | 840 |

```
atcttccgtc tgtttgctgc catcatgaac ttcaagaagg atgaaattcc agttctgttg    900
gagaaattgg agatcaacct gaagcgtgag gagaaggagt tggagggtaa ggctcttttg    960
aaggttgtca tgagaaagtt cttgccagct gccgacgctt tgttggagat gattgttctt   1020
cacctgccat ctccagtcac cgctcaagct tacagagccg agactttgta cgaaggtcca   1080
tctgatgacc aattctgcat tggtatcaga gagtgtgacc ctaaggctga gctgatggtt   1140
tacatttcca agatggtgcc aacctccgac aaaggtagat ctacgccctt cggtcgtgtt   1200
ttctccggta ctgttaagtc cggtcaaaag gtcagaatcc aaggtcctaa ctacgttcca   1260
ggtaagaagg aggacttgtt catcaaggct gttcaaagaa ctgttttgat gatgggaaga   1320
accgtcgagc ctattgacga tgtcccagct ggtaacattc tgggtattgt gggtatcgac   1380
cagttcttgc tgaagtctgg tactcttact accaacgaag ccgctcacaa catgaaggtg   1440
atgaaattct ctgtctctcc agttgtgcaa gttgccgttg aggtcaagaa cgctaatgat   1500
ctgcccaagt tggttgaggg tctgaagcgt tgtccaagt ctgacccatg tgttttaacc    1560
tacatctccg agtctggtga gcacattgtt gctggtactg gtgagctgca cttggaaatc   1620
tgtttgcaag atctgcaaga cgaccacgct ggtgtccctc tgaagatttc tcctccagtt   1680
gttacctacc gtgagactgt cactaacgaa tcttccatga ctgccctgtc aagtctcag    1740
aacaagcata acagaattta cctgaaggct caaccaattg acgaggaatt gtctttggct   1800
atcgaagaag gtaaggttca cccaagagac gactttaaag ccagagccag aatcatggct   1860
gatgaatacg gttgggacgt cactgatgcc agaaagatct ggtgtttcgg tccagacggt   1920
actggtgcca acttagttgt tgaccagtct aaggctgtcc aatacttgca cgagatcaag   1980
gactctgttg ttgccggttt ccaattggct accaaggaag gtccaatttt gggagaaaac   2040
atgagatccg tcagagtcaa catcttggat gttaccctgc acgccgatgc tatccacaga   2100
ggtggaggac aagtcattcc aaccatgaag agagttacct acgccgcctt cctgttggct   2160
gagccagcta tccaggagcc tatcttcttg gtggagatcc aatgtccaga gaatgccatt   2220
ggtggtatct actctgtttt gaacaagaag agaggtcaag ttatctctga ggaacaaaga   2280
ccaggtaccc cattgttcac tgtcaaagct tacttgccag ttaacgagtc attcggtttc   2340
accggtgaac tgagacaagc taccgctggt caagctttcc cacagatggt gttcgaccac   2400
tgggccaaca tgaatggtaa cccattggac ccagcctcca aggtcggtga gattgttctt   2460
gctgccagaa agagacaggg tatgaaggag aacgttcctg ttatgaaga gtactacgac    2520
aagttgtaag cttaatgttt cattaactta tttgtgtcgt tcgtatgtct atttacgtac   2580
ttaattcagt gtattgttgt t                                              2601
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence; note = synthetic construct

<400> SEQUENCE: 14

Ala His Val Asp His Gly Lys Ser Thr
 1               5

<210> SEQ ID NO 15
<211> LENGTH: 13
<212> TYPE: PRT

<213> ORGANISM: Artificial Sequence
<220> FEATURE:
<223> OTHER INFORMATION: Description of Artificial Sequence; note = synthetic construct

<400> SEQUENCE: 15

Asp Glu Gln Glu Arg Gly Ile Thr Ile Lys Ser Thr Ala
1               5                   10

<210> SEQ ID NO 16
<211> LENGTH: 896
<212> TYPE: PRT
<213> ORGANISM: Artificial Sequence
<220> FEATURE:
<223> OTHER INFORMATION: Description of Artificial Sequence; note = synthetic construct

<400> SEQUENCE: 16

Ala Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly

-continued

```
            305                 310                 315                 320
        Ala Val His His Asn Thr Glu Glu Ile Val Ala Gln Ser Ile Ala Leu
                            325                 330                 335

Ser Ser Leu Met Val Ala Gln Ala Ile Pro Leu Val Gly Glu Leu Val
                            340                 345                 350

Asp Ile Gly Phe Ala Ala Tyr Asn Phe Val Glu Ser Ile Ile Asn Leu
                            355                 360                 365

Phe Gln Val Val His Asn Ser Tyr Asn Arg Pro Ala Tyr Ser Pro Gly
                370                 375                 380

His Lys Thr Gln Pro Phe Leu Pro Trp Asp Ile Gln Met Thr Gln Thr
        385                 390                 395                 400

Thr Ser Ser Leu Ser Ala Ser Leu Gly Asp Arg Val Thr Ile Ser Cys
                            405                 410                 415

Arg Ala Ser Gln Asp Ile Arg Asn Tyr Leu Asn Trp Tyr Gln Gln Lys
                            420                 425                 430

Pro Asp Gly Thr Val Lys Leu Leu Ile Tyr Tyr Thr Ser Arg Leu His
                    435                 440                 445

Ser Gly Val Pro Ser Lys Phe Ser Gly Ser Gly Ser Gly Thr Asp Tyr
                450                 455                 460

Ser Leu Thr Ile Ser Asn Leu Glu Gln Glu Asp Ile Ala Thr Tyr Phe
        465                 470                 475                 480

Cys Gln Gln Gly Asn Thr Leu Pro Trp Thr Phe Ala Gly Gly Thr Lys
                            485                 490                 495

Leu Glu Ile Lys Gly Gly Gly Ser Gly Gly Gly Ser Gly Gly
                        500                 505                 510

Gly Gly Ser Glu Val Gln Leu Gln Gln Ser Gly Pro Glu Leu Val Lys
                    515                 520                 525

Pro Gly Ala Ser Met Lys Ile Ser Cys Lys Ala Ser Gly Tyr Ser Phe
                530                 535                 540

Thr Gly Tyr Thr Met Asn Trp Val Lys Gln Ser His Gly Lys Asn Leu
        545                 550                 555                 560

Glu Trp Met Gly Leu Ile Asn Pro Tyr Lys Gly Val Ser Thr Tyr Asn
                            565                 570                 575

Gln Lys Phe Lys Asp Lys Ala Thr Leu Thr Val Asp Lys Ser Ser Ser
                            580                 585                 590

Thr Ala Tyr Met Glu Leu Leu Ser Leu Thr Ser Glu Asp Ser Ala Val
                    595                 600                 605

Tyr Tyr Cys Ala Arg Ser Gly Tyr Tyr Gly Asp Ser Asp Trp Tyr Phe
                610                 615                 620

Asp Val Trp Gly Ala Gly Thr Thr Val Thr Val Ser Ser Gly Gly Gly
        625                 630                 635                 640

Gly Ser Gly Gly Gly Gly Ser Gly Gly Gly Gly Ser Asp Ile Gln Met
                            645                 650                 655

Thr Gln Thr Thr Ser Ser Leu Ser Ala Ser Leu Gly Asp Arg Val Thr
                            660                 665                 670

Ile Ser Cys Arg Ala Ser Gln Asp Ile Arg Asn Tyr Leu Asn Trp Tyr
                    675                 680                 685

Gln Gln Lys Pro Asp Gly Thr Val Lys Leu Leu Ile Tyr Tyr Thr Ser
                690                 695                 700

Arg Leu His Ser Gly Val Pro Ser Lys Phe Ser Gly Ser Gly Ser Gly
        705                 710                 715                 720

Thr Asp Tyr Ser Leu Thr Ile Ser Asn Leu Glu Gln Glu Asp Ile Ala
                            725                 730                 735
```

```
Thr Tyr Phe Cys Gln Gln Gly Asn Thr Leu Pro Trp Thr Phe Ala Gly
            740                 745                 750

Gly Thr Lys Leu Glu Ile Lys Gly Gly Gly Ser Gly Gly Gly
        755                 760                 765

Ser Gly Gly Gly Gly Ser Glu Val Gln Leu Gln Gln Ser Gly Pro Glu
770                 775                 780

Leu Val Lys Pro Gly Ala Ser Met Lys Ile Ser Cys Lys Ala Ser Gly
785                 790                 795                 800

Tyr Ser Phe Thr Gly Tyr Thr Met Asn Trp Val Lys Gln Ser His Gly
            805                 810                 815

Lys Asn Leu Glu Trp Met Gly Leu Ile Asn Pro Tyr Lys Gly Val Ser
        820                 825                 830

Thr Tyr Asn Gln Lys Phe Lys Asp Lys Ala Thr Leu Thr Val Asp Lys
            835                 840                 845

Ser Ser Ser Thr Ala Tyr Met Glu Leu Leu Ser Leu Thr Ser Glu Asp
        850                 855                 860

Ser Ala Val Tyr Tyr Cys Ala Arg Ser Gly Tyr Tyr Gly Asp Ser Asp
865                 870                 875                 880

Trp Tyr Phe Asp Val Trp Gly Gln Gly Thr Thr Leu Thr Val Phe Ser
            885                 890                 895

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 15
<223> OTHER INFORMATION: S = G or C

<400> SEQUENCE: 17
ggggsggggs ggggs                                                      15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 4,8,12,16
<223> OTHER INFORMATION: s = g or c

<400> SEQUENCE: 18
gggsgggsgg gsgggs                                                     16

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
```

```
<222> LOCATION: 3
<223> OTHER INFORMATION: Xaa = s or t

<400> SEQUENCE: 19

Asn Xaa Xaa
  1

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 20
ttggttattg accaaactaa ggctgtccaa                                      30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 21
acctctcttc ttgtttaaga cggagtagat                                      30

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 22
cttgcttttg cggccgcttt tttttttttt tttttttt                             39

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 23
gataagaatg cggccgccat ttcttggtct ttgggttgaa g                         41

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 24
gataagaatg cggccgccaa cttagttgtt gaccagtcta ag                        42

<210> SEQ ID NO 25
<211> LENGTH: 36
<212> TYPE: DNA
<213> ORGANISM: Artificial Sequence
<220> FEATURE:
```

```
<223> OTHER INFORMATION: Description of Artificial Sequence; note =
      synthetic construct

<400> SEQUENCE: 25
atagctagca ctttgaagtt cttaattttg ttcctc                                    36

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 26
ataagaatgc ggccgcaagt taatgaaaca ttaagcttac aac                            43

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 27
gaatgacttg tcctccacc                                                       19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 28
gaatgacttg tcctccgcgg                                                      20

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 29
caactagcta gcgctcacaa catgaaggtc atgaaattc                                 39

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30
agaaccgtcg agcctattga cgat                                                 24

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence; note =
``` synthetic construct

<400> SEQUENCE: 31
ccctgcacgc cgatgctatc cacagaagag gaggacaagt cattccaacc atgaag    56

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 32
gccgatgcta tccacagaag a    21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 33
gccgatgcta tccaccgccg c    21

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 34
tctcttcttg ttcaaaacag agtagatacc    30

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc feature
<222> LOCATION: 7, 15
<223> OTHER INFORMATION: n = g, a, c or t(u)

<400> SEQUENCE: 35
gtatgtncac taacntag    18